Figure 1A:
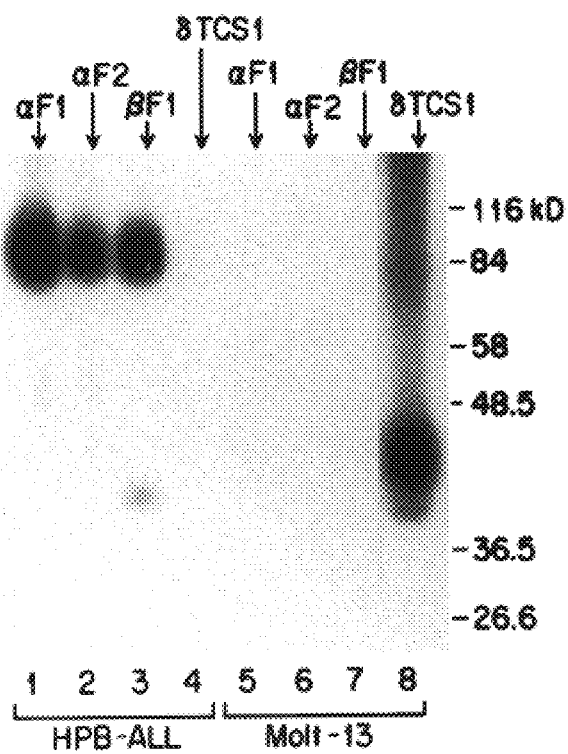

United States Patent [19]
Skibbens et al.

[11] Patent Number: 6,048,526
[45] Date of Patent: Apr. 11, 2000

[54] MONOCLONAL ANTIBODIES REACTIVE WITH DEFINED REGIONS OF THE T CELL ANTIGEN RECEPTOR

[75] Inventors: Robert V. Skibbens, Chapel Hill, N.C.; Larry D. Henry, Brookline, Mass.; Charles W. Rittershaus, Malden, Mass.; Wei-Tao Tian, Allston, Mass.; Stephen H. Ip, Sudbury, Mass.; Patrick C. Kung, Lexington, Mass.; Mary Ellen Snider, Ledyard, Conn.; Jone-Long Ko; Nancy L. Wood, both of Cambridge, Mass.

[73] Assignee: Astra AB

[21] Appl. No.: 08/083,408

[22] Filed: Jun. 25, 1993

Related U.S. Application Data

[60] Division of application No. 07/449,692, Dec. 11, 1989, Pat. No. 5,223,426, which is a continuation-in-part of application No. 07/343,189, Apr. 25, 1989, abandoned, which is a continuation-in-part of application No. 07/284,511, Dec. 15, 1988, abandoned.

[51] Int. Cl.$^7$ .......................... A61K 39/395; C12P 21/08
[52] U.S. Cl. .................................. 424/144.1; 530/388.75
[58] Field of Search .............................. 424/144.1, 144.4; 530/388.22, 388.75; 435/240.27, 172.3, 70.21, 7.1, 7.2

[56] References Cited

U.S. PATENT DOCUMENTS

| | | |
|---|---|---|
| 4,550,086 | 10/1985 | Reinherz et al. . |
| 4,634,586 | 1/1987 | Goodwin et al. ........................ 424/1.1 |
| 4,845,026 | 7/1989 | Kung et al. . |
| 4,886,743 | 12/1989 | Hood et al. . |
| 4,923,799 | 5/1990 | Mak et al. . |

FOREIGN PATENT DOCUMENTS

| | | |
|---|---|---|
| 0180878 A2 | 10/1985 | European Pat. Off. . |
| 180171 A2 | 10/1985 | European Pat. Off. . |
| 0200350 A2 | 3/1986 | European Pat. Off. . |
| 0289252 A2 | 11/1988 | European Pat. Off. . |
| 0340109 A2 | 4/1989 | European Pat. Off. . |
| 0250333 A1 | 10/1987 | Germany . |
| 61-254529 | 11/1986 | Japan . |
| 63-030500 | 2/1988 | Japan . |
| 2197323 | 5/1988 | United Kingdom . |
| WO 84/02848 | 8/1984 | WIPO . |
| WO 88/00209 | 1/1988 | WIPO . |
| WO 89/02899 | 4/1989 | WIPO . |
| WO 89/05309 | 6/1989 | WIPO . |
| WO/92 12996 | 8/1992 | WIPO . |

OTHER PUBLICATIONS

Maecker and Levy (1989), J. Immunol. 142:1395–1404.
Posnett et al. (1986), Proc. Nat'l Acad. Sci. USA 83:7888–7892.
Boylston et al. (1986) J. Immunol. 137:741–744.
Bigler and Chiorazzi, (1987) in the Molecular Basis of B–Cell Differentiation and Function, Ferrerini and Pernis, eds., Plenum Press, pp. 123–130.
Bigler et al. (1985), J. Exp. Med. 161: 1450–1463.
Bigler et al. (1983), J. Exp. Med. 158: 1000–1005.
Fabbi et al. (1985), Eur. J. Immunol. 15: 821–827.
Spits et al. (1985), J. Immunol. 135: 1922–1928.
Samelson et al. (1983), Proc. Nat'l Acad. Sci. U.S.A. 80: 6972–6976.
Reinherz et al. (1984), Immunol. Rev. 81: 95–129.
Meuer et al. (1983), J. Exp. Med. 157: 705–719.
McIntyre and Allison (1983), Cell 34: 739–746.
Marchalonis (1987), Antigen–Specific T–Cell Receptors and Factors, Vols. I and II, Marchalonis (Ed.), CRC Press, Boca Raton, Florida, Table of Contents and pp. 18–21.
Brenner et al. (1984), J. Exp. Med. 160: 541–551.
Tian et al. (1989) FASEB J., 3: A486 (and poster).
Borst et al. (1987), J. Immunol. 139: 1952–1959.
Brenner et al. (1987), J. Immunol. 138: 1502–1509.
Maecker et al. (1987), J. Immunol. Methods 98: 219–226.
Picker et al. (1987), Am. J. Pathol. 129: 434–440.
Ng et al. (1988), Am. J. Pathol. 132: 365–371.
Moller et al. (1988), J. Clin. Invest. 82: 1183–1191.
Tillinghast et al. (1986), Science 233: 879–883.
Waldmann et al. (1985), New Eng. J. Med. 313: 776–783.
Schluter et al. (1986), Proc. Nat'l. Acad. Sci. U.S.A. 83: 1872–1876.
Kappler et al. (1989), Science 244: 811–813.
Brennan et al. (1988), J. Autoimmun. 1: 319–326.
Grossi et al. (1989), Proc. Nat'l. Acad. Sci. U.S.A. 86: 1619–1623.
Wu et al. (1988), J. Immunol. 141: 1476–1479.
Augustin et al. (1989), Nature 340: 239–241.
Ferrini et al. (1987), J. Exp. Med. 166: 277–282.
Brenner et al. (1986) Nature 322: 145–149.
Compana et al. (1989), J. Immunol. 142: 57–66.
Janson et al. (1989a), Cancer Immunol. Immunother. 28: 225–232.

(List continued on next page.)

*Primary Examiner*—Marianne P. Allen
*Attorney, Agent, or Firm*—Banner & Witcoff, Ltd.; Kathleen M. Williams

[57] ABSTRACT

The present invention relates to monoclonal antibodies which recognize defined regions of the T-cell receptor (TCR). In a specific embodiment, the invention provides monoclonal antibodies which are reactive with a constant region of the alpha chain of the TCR. In particular embodiments, the invention relates to two monoclonal antibodies, termed αF1 and αF2, which react with two different epitopes on the framework region of the α monomer of the TCR molecule. In another specific embodiment, the invention is directed to monoclonal antibodies reactive with a variable region of the beta chain of the TCR. In particular, the invention provides two monoclonal antibodies, termed W112 and 2D1, which react with β chain variable regions Vβ5.3 and Vβ8.1, respectively. In another specific embodiment, the invention is directed to monoclonal antibodies reactive with a variable region of the delta chain of the TCR. In particular, the invention provides monoclonal antibody δTCS1, isotype IgG2a. The monoclonal antibodies of the invention have value in diagnosis and therapy and are useful tools for study of the immune system.

29 Claims, 26 Drawing Sheets

FOREIGN PATENT DOCUMENTS

Janson et al. (1989b), in Human Tumor Antigens and Specific Tumor Therapy, Alan R. Liss, Inc. pp. 277–286.

Wraith et al. (1989), Cell 57: 709–715.

Howell et al. (1989), Science 246: 668–670.

Ashwell et al. (1987), Science 237: 61–64.

Urban et al. (1988), Cell 54: 577–592.

Acha–Orbea et al. (1988), Cell 54: 263–273.

Vacchio and Hodes (1989), J. Exp. Med. 170: 1335–1346.

Webb and Sprent (1987), J. Exp. Med. 165: 584–589.

Janson et al. (1987), Scand. J. Immunol. 26: 237–246.

Behlke et al. (1987), J. Exp. Med. 165: 257–262.

Fowlkes et al. (1987) Nature 329: 251–254.

Payne et al. (1988) Proc. Nat'l Acad. Sci. U.S.A. 85: 7695–7698.

Staerz et al. (1985), J. Immunol. 134: 3994–4000.

Haskins et al. (1984), J. Exp. Med. 160: 452–471.

Chan and Takei (1986), J. Immunol. 136: 1346–1355.

Guy et al. (1989), Science 244: 1477–1480.

Sim et al. (1984) Nature 312: 771–775.

Saito et al. (1984) Nature 309: 757–762.

Minami et al. (1987) J. Biol. Chem 262: 13342–13347.

Acuto et al. (1983) Cell 34: 717–726.

Kappler et al. (1983) Cell 35:295–302.

Traunecker et al. (1986) Eur. J. Immunol. 16:851–854.

et al. Clinical and Experimental Rheumatology 15:475–479, 1997.

Diu et al., "Fine specificity of monoclonal antibodies directed at human T cell receptor variable regions: comparison with oligonucleotide–driven amplification for evaluation of Vβ expression," *Eur. J. Immunology*, 23(7):1422–1429 (1993).

Haqqi et al., "R III S/J (H–2r). An Inbred Mouse Strain with a Massive Deletion of T Cell Receptor Vβ Genes," *J. Experimental Medicine*, 169(6):1903–1909 (1989).

Inamitsu, "Immunological function of HLA–DQw6 molecules expressed in DQw6 transgenic C57BL/6 mice," *Fukuoka Igaku Zasshi*, 82(2):59–70 (1991).

Pontzer et al., "T cell antigen receptor binding sites for the microbial superantigen staphylococcal enterotoxin A," *Proc. Nat'l Acad. Sci. USA*, 89(16):7727–7731 (1992).

Pullen et al., "The T–cell repertoire is heavily influenced by tolerance to polymorphic self–antigens," *Nature*, 335(6193):796–801 (1988).

Viney et al., "Generation of Monoclonal Antibodies Against a Human T Cell Receptor β Chain Expressed in Transgenic Mice," *Hybridoma*, 11(6):701–713 (1992).

Houghton et al., Seminars in Oncology 13: 165–179 1986.

Casali et al. Science 234:476–479, 1986.

Harris et al. Tibtech 11:42–44, 1993.

Tian et al., Faseb J. 3(3):A486, 1989.

Lipoldova et al., Immunogenetics 30:162–168, 1989.

Concannon et al., PNAS USA 83:6598–6602, 1986.

Kimura et al., J Exp Med. 164:739–750, 1986.

Toyonaga et al. Ann Rev Immunol. 5:585–620, 1987.

Chan et al., Cancer 62:2118–2124, 1988.

Goding,"Monoclonal Antibodies: Principles and Practice", Academic Press, 1986, pp. 125–133.

Boylston et al., J. Immunol. 137:741–4, 1986.

Borgato et al. Clinical and Experimenal Rheumatology 15:475–479.

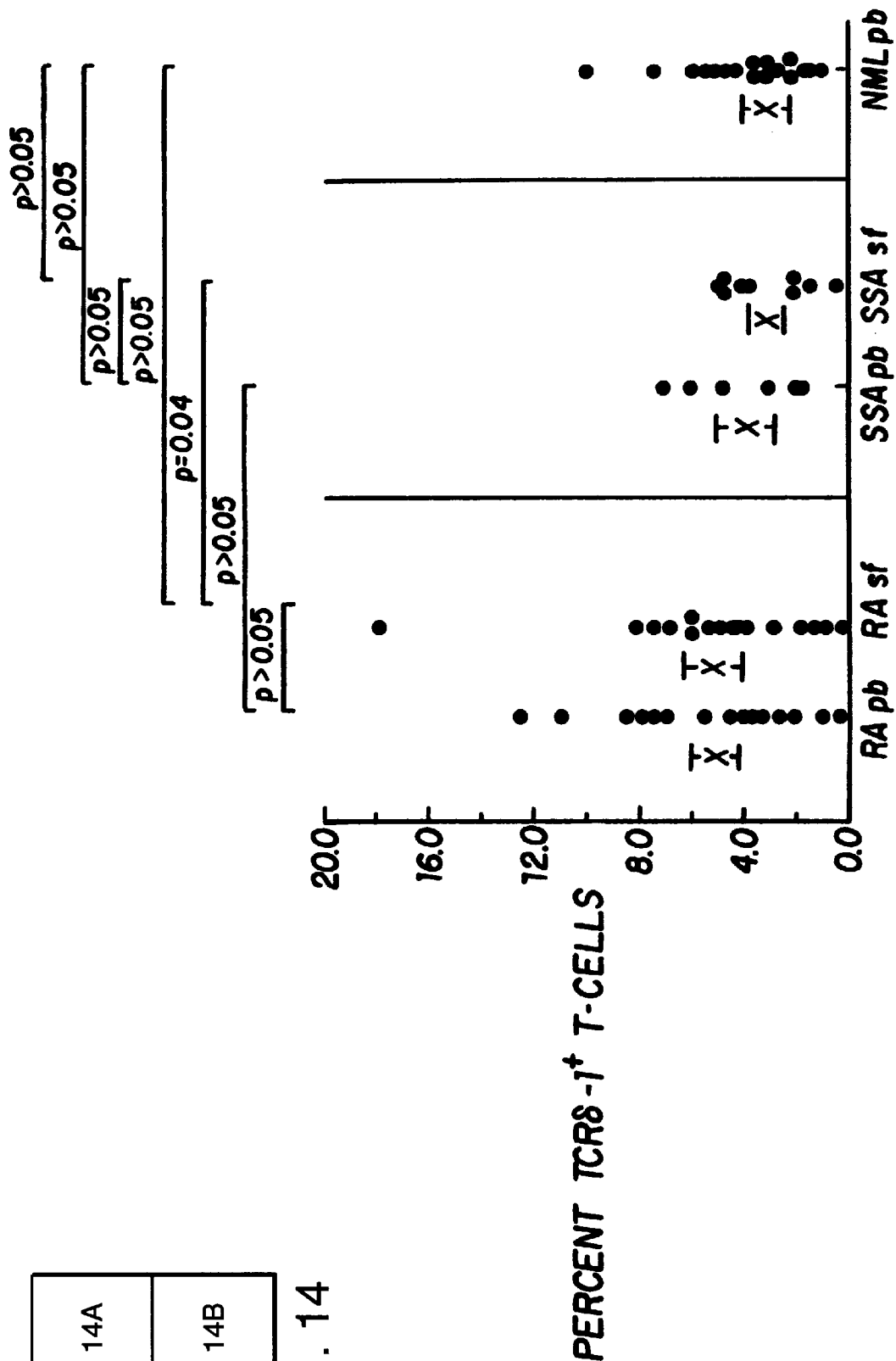

MONOCLONAL ANTIBODIES REACTIVE WITH DEFINED REGIONS OF THE T CELL ANTIGEN RECEPTOR

This application is a division of application Ser. No. 07/449,692, now U.S. Pat. No. 5,223,426 filed Dec. 11, 1989, which is a continuation-in-part of U.S. patent application Ser. No. 07/343,189 filed Apr. 25, 1989, abandoned which is a continuation-in-part of application Ser. No. 07/284,511 filed Dec. 15, 1988, now abandoned each of which is incorporated by reference herein in its entirety.

TABLE OF CONTENTS

1. Introduction
2. Background of the Invention
   2.1. The T Cell Antigen Receptor
   2.2. T Cell Antigen Receptor Genes
   2.3. Antibodies To the T Cell Antigen Receptor
   2.4. Rheumatoid Arthritis
   2.5. Role of T Cells in Rheumatoid Arthritis
   2.6 γδ Positive T Cells
3. Summary of the Invention
   3.1. Abbreviations and Definitions
4. Description of the Figures
5. Detailed Description of the Invention
   5.1. Generation of Monoclonal Antibodies Reactive With Defined Regions of the T Cell Antigen Receptor
   5.2. Fragments and Derivatives of Monoclonal Antibodies Reactive With Defined Regions of the T Cell Antigen Receptor
   5.3. Immunoassays
   5.4. Diagnosis and Therapy
      5.4.1. Diagnosis
      5.4.2. Therapy
      5.4.3. Therapeutic Compositions; Kits
   5.5. Monoclonal Antibodies Reactive With the Constant Regions of the T Cell Antigen Receptor Alpha Polypeptide
      5.5.1. Binding Specificities of αF1 and αF2
      5.5.2. Immunohistological Analysis Using αF1 and αF2
      5.5.3. Uses of αF1 and αF2
   5.6. Monoclonal Antibodies Reactive With the Variable Region of the T Cell Antigen Receptor Beta Polypeptide
      5.6.1. Binding Specificities of W112 and 2D1
      5.6.2. Uses of W112 and 2D1
6. Example: The Generation of Two Monoclonal Antibodies, αF1 and αF2, Directed Against Two Different Epitopes on the Human αTCR Constant Region
   6.1. Materials and Methods
      6.1.1. Cell Lines
      6.1.2. Monoclonal Antibodies
      6.1.3. T-Cell Lysates and αβ TCR Protein
      6.1.4. ELISA Method for Screening mAb
      6.1.5. Assay for TCR Peptide Binding
      6.1.6. Immunoprecipitation and SDS-PAGE
      6.1.7. Immunohistological Tissue Section Analysis
      6.1.8. In vitro Translation
   6.2. Results
      6.2.1. Isolation of Framework mAb
      6.2.2. Reactivity of mAb αF1 and αF2
      6.2.3. Specificity of αF1 and αF2 mAb
      6.2.4. Immunoprecipitation of in vitro Synthesized α Chain TCR By αF1 and αF2
   6.3. Discussion
7. Example: Monoclonal Antibodies to the Variable Regions of Human T Cell Antigen Receptor
   7.1. Results
      7.1.1. Generation of W112 and 2D1 Monoclonal Antibodies
      7.1.2. Specificity of W112 and 2D1
      7.1.3. Fluorescence Activated Cell sorting using W112 and 2D1
   7.2 Discussion
8. Example: Elevation of a γδ T-Cell Subset in Peripheral Blood and Synovial Fluid of Patients With Rheumatoid Arthritis
   8.1. Materials and Methods
      8.1.1. Patient Selection
      8.1.2. Clinical Evaluation
      8.1.3. Preparation of Mononuclear Cells From Peripheral Blood
      8.1.4. Immunofluorescence Staining of Cell Surface Markers
   8.2. Results
   8.3. Discussion
9. Example: Novel Autoreactive Cytotoxic Activity Against Synoviocytes by Rheumatoid Arthritis Derived T Cell Lines and Clones
   9.1. Materials and Methods
      9.1.1. Patient Samples
      9.1.2. Sample Processing and Cell Lines
      9.1.3. Synovial Tissue-Derived T Cell Lines
      9.1.4. Peripheral Blood Derived T Cell Lines
      9.1.5. B Cell Lines
      9.1.6. Peripheral Blood Macrophages
      9.1.7. Synoviocytes
      9.1.8. Cell Surface Phenotyping
      9.1.9. Cytotoxicity Assay
      9.1.10. In Situ Immunohistochemistry
      9.1.11. Suppressor Factor Assay
   9.2. Results
      9.2.1. Cell Surface Phenotype of Synovial Tissue-Derived and Peripheral Blood-Derived T Cells
         9.2.1.1. δTCS1 Cell Surface Phenotype
         9.2.1.2. CD4, CD8, 4B3, 4H4, 2H4 Cell Surface Phenotypes
      9.2.2. In Situ Immunohistochemistry
      9.2.3. Functional Activity of Synovial Tissue Derived T cells
         9.2.3.1. Cytotoxic Activity
         9.2.3.2. Cytotoxic Activity of a γδ Positive ST Cell Line; Effect of δTCS1 Monoclonal Antibody
         9.2.3.3. Suppressor Activity of γδ Positive ST Cell Lines
      9.2.4. Blocking of the Cytotoxicity Reaction By δTCS1
      9.2.5. Depletion Assay Using δTCS1
   9.3. Discussion
10. Example: δTCS1, a Monoclonal Antibody Reactive With the Vδ1 Region of Human T Cell Antigen Receptor, is Useful in the Treatment of Rheumatoid Arthritis
    10.1. Preclinical Data
       10.1.1. Peripheral Blood Study in RA and Felty's Patients 10.1.2. Longitudinal Studies
10.1.3. Synovial Fluid and Synovium Tissue Study
10.1.4. Activity of γδ+ T Cells in Rheumatoid Arthritis
10.1.5. αβ T Cell Analysis in Arthritis
10.1.6. Toxicology of δTCS1 Monoclonal Antibody
10.1.7. Pharmakinetics of δTCS1 Monoclonal Antibody
10.1.8. Physical Biochemical Properties of δTCS1 Monoclonal Antibody
10.2. Clinical Plan for Elimination Protocol
10.2.1. Indication
10.2.2. Patient Admission Criteria to the Study
10.2.3. Clinical Endpoint
10.2.4. Calculation of Drug Dose
10.2.5. Regimen
10.3. Summary
11. Example: Monoclonal Antibodies Reactive With the Variable Regions of α, β Human T Cell Antigen Receptor are Useful in the Treatment of Rheumatoid Arthritis
11.1. Materials and Methods
11.1.1. Samples
11.1.2. T Cell Receptor Variable Region Gene Probes
11.1.3. RNA Preparations:
11.1.4. T Cell Antigen Receptor Usage Analysis:
    11.1.4.1. cDNA Synthesis
    11.1.4.2. Polymerase Chain Reaction (PCR) Amplification
    11.1.4.3. DNA Slot Blot Analysis
11.2. Results
11.3. Summary
11.4. Discussion: Treatment of Rheumatoid Arthritis Patients with TCR α, β, Specific Reagents
12. Deposit of Hybridomas

1. INTRODUCTION

The present invention is directed to monoclonal antibodies, which recognize defined regions of the T cell antigen receptor. The monoclonal antibodies of the invention have value in diagnosis and therapy and are useful tools for study of the immune system.

2. BACKGROUND OF THE INVENTION

2.1. The T Cell Antigen Receptor

T lymphocytes interact with antigens through the T cell antigen receptor (TCR) complex. The TCR is a clone-specific heterodimer on T cells, which recognizes its target antigen in association with a major histocompatiblity antigen. The TCR has been shown to be noncovalently associated with the CD3 complex. TCR is highly polymorphic between T cells of different specificities. Approximately 90 percent of peripheral blood T cells express a TCR consisting of an α polypeptide and a β polypeptide. A small percentage of T cells have been shown to express a TCR consisting of a γ polypeptide and a δ polypeptide. (Regarding TCR molecules, see Davis and Bjorkman, 1988, Nature 334:395–402; Marrack and Kappler, 1986, Sci. Amer. 254: 36; Meuer et al., 1984, Ann. Rev. Immunol. 2:23–50; Brenner et al., 1986, Nature 322:145–159; Krangel et al., 1987, Science 237:1051–1055; Hata et al., 1987, Science 238:678–682; Hochstenbach et al., 1988, J. Exp. Med. 168:761–776). The chains of the T cell antigen receptor of a T cell clone are each composed of a unique combination of domains designated variable (V), [diversity (D),] joining (J), and constant (C) (Siu et al., 1984, Cell 37:393; Yanagi et al., 1985, Proc. Natl. Acad. Sci. U.S.A. 82:3430). Hypervariable regions have been identified (Patten et al., 1984, Nature 312:40; Becker et al., 1985, Nature 317:430). In each T cell clone, the combination of V, D and J domains of both the alpha and the beta chains or of both the delta and gamma chains participates in antigen recognition in a manner which is uniquely characteristic of that T cell clone and defines a unique binding site, also known as the idiotype of the T cell clone. In contrast, the C domain does not participate in antigen binding.

2.2. T Cell Antigen Receptor Genes

TCR genes, like immunoglobulin genes, consist of regions which rearrange during T cell ontogeny (Chien et al., 1984, Nature 312:31–35; Hedrick et al., 1984, Nature 308:149–153; Yanagi et al., 1984, Nature 308:145–149). In genomic DNA, each TCR gene has V, J, and C regions; TCR β and δ polypeptides also have D regions. The V (variable), D (diversity), J (junctional) and C (constant) regions are separated from one another by spacer regions in the DNA. There are usually many variable region segments and somewhat fewer diversity, junctional, and constant region segments. As a lymphocyte matures, these various segments are spliced together to create a continuous gene sequence consisting of one V, (D), J, and C region. TCR diversity, and thereby T cell specificity, is derived from several sources (Barth et al., 1985, Nature 316:517–523; Fink et al., 1986, Nature 321:219–225): a multiplicity of germline gene segments (Chien et al., 1984, Nature 309:322–326; Malissen et al., 1984, Cell 37:1101–1110; Gascoigne et al., 1984, Nature 310:387–391; Kavaler et al., 1984, Nature 310: 421–423; Siu et al., 1984, Nature 311:344–349; Patten et al., 1984, Nature 312:40–46), combinatorial diversity through the assembly of different V, D, J, and C segments (Siu et al., 1984, Cell 37:393–401; Goverman et al., 1985, Cell 40:859–867), and junctional flexibility, N-region diversity and the use of either multiple D regions or any of the three translational reading frames for Dβ segments. TCR diversity does not appear to arise from the somatic hypermutation mechanism observed for immunoglobulins (Barth et al., supra). As a result of these mechanisms, TCRs are generated which differ in their amino-terminal, or N-terminal, domains (called variable, or V regions, constructed from combinations of V, D, and J gene segments) but are the same elsewhere, including their carboxy-terminal, or C-terminal, domains (called constant regions). Accordingly, an almost limitless repertoire of TCR is established.

The Vβ gene of the TCR appears to resemble most closely the immunoglobulin V gene in that it has three gene segments, Vβ, Dβ, and Jβ, which rearrange to form a contiguous Vβ gene (Siu et al., 1984, Cell 37:393–401). The β locus has been well characterized in mice, where it spans 700–800 kilobases of DNA and is comprised of two nearly identical C regions tandemly arranged with one D element and a cluster of 5–6 J elements 5' to each (Kronenberg et al., 1986, Ann. Rev. Immunol. 3:537–560). Approximately twenty to thirty Vβ regions are located upstream (5') to the D, J, and C elements (Behlke et al., 1985, Science 229:566–570) although Vβ genes may also be located 3' to the murine Cβ genes (Malissen et al., 1986, Nature 319:28). Study of the structure and diversity of the human TCR β-chain variable region genes has led to the grouping of genes into distinct Vβ subfamilies (Tillinghast et al., 1986, Science 233:879–883; Concannon et al., 1986, Proc. Natl. Acad. Sci. U.S.A. 83:6598–6602; Borst et al., 1987, J. Immunol. 139:1952–1959).

The γTCR gene was identified, first in mice (Saito et al., 1984, Nature 309:757–762; Kranz et al., 1985, Nature 313:762–755; Hayday et al., 1985, Cell 40:259–269) and then in humans (Lefranc et al., 1985, Nature 316:464–466; Murre et al., 1985, Nature 316:549–552). The human γTCR locus appears to consist of between five and ten variable, five joining, and two constant region genes (Dialynas et al., 1986, Proc. Natl. Acad. Sci. U.S.A. 83:2619).

The TCR α and δ locus are next to one another on human chromosome 14. Many TCR δ coding segments are located entirely within the α gene locus (Satyanarayana et al., 1988, Proc. Natl. Acad. Sci. U.S.A. 85:8166–8170 Chien et al., 1987, Nature 330:722–727; Elliot et al., 1988, Nature 331:627–631). It is estimated that there are a minimum of 45–50 Vα regions (Becker et al., Nature 317:430–434) whereas there are only approximately 10 Vδ regions (Chien et al., 1987, supra). In peripheral blood, two predominant Vδ genes appear to be expressed, namely, Vδ1 and Vδ2, identifiable by monoclonal antibodies, δTCS1 and BB3, respectively. Nucleic acid sequences of TCR a genes have been reported (Sim et al., 1984, Nature 312:771–775; Yanagi et al., 1985, Proc. Natl. Acad. Sci. U.S.A. 82:3430–3434; Berkout et al., 1988, Nucl. Acids Res. 16:5208).

2.3. Antibodies to the T Cell Antigen Receptor

Clonotypic antibodies react only with a particular clone of T cells. Acuto et al. produced clonotypic monoclonal antibodies against a human thymocyte cell line, and thereby identified the TCR in relatively undifferentiated T3+ cells (1983, Cell 34:717–726). Meuer et al. showed that anti-TCR clonotypic monoclonal antibodies coupled to sepharose beads could induce production of interleukin-2 (1984, Proc. Natl. Acad. Sci. 81:1509–1513). Anti-TCR clonotypic antibody directed toward the CT8 cell line could only block cytotoxic effector cell function of that T cell line (Meuer et al., 1984, Ann. Rev. Immunol. 2:23–50). Antibodies which recognize TCR from many T cell lines recognize shared epitopes, or framework regions, of TCR peptides. Brenner et al. found that different cloned T cell lines shared antigenic determinants, none of which appeared to be accessible at the cell surface (1984, J. Exp. Med. 160:541–551). β-Framework-1 (βF1) monoclonal antibody reacts with a "hidden determinant" on the surface of viable T cells, and recognizes the TCR β polypeptide in Western blots (Brenner et al., 1987, J. Immunol. 138:1502–1509). Another framework antibody, WT31, originally thought to be a framework reagent is useful in cell binding, but is inefficient in immunoprecipitation studies (Spits et al., 1985, J. Immunol. 135:1922–1928). WT31 now appears to recognize a CD3 determinant.

2.4. Rheumatoid Arthritis

Rheumatoid arthritis (RA), a chronic, recurrent, inflammatory disease primarily involving joints, affects 1–3% of North Americans, with a female to male ratio of 3:1. Severe RA patients tend to exhibit extra-articular manifestations including vasculitis, muscle atrophy, subcutaneous nodules, lymphadenopathy, splenomegaly and leukopenia. Spontaneous remission may occur; other patients have brief episodes of acute arthritis with longer periods of low-grade activity; still others progress to severe deformity of joints. In some patients with rheumatoid arthritis, particularly those with long-standing disease, a constellation of symptoms called "Felty's syndrome" develops, in which the typical arthropathy is accompanied by splenomegaly and neutropenia. It is estimated that about 15% of RA patients (severe RA and Felty's syndrome) become completely incapacitated ("primer on the Rheumatic Diseases, 8th edition, 1983, Rodman, G. P. & Schumacher, H. R., Eds., Zvaifler, N. J., Assoc. Ed., Arthritis Foundations, Atlanta, Ga.).

The antigenic stimulus initiating the immune response and consequent inflammation is unknown. Certain HLA types (DR4, Dw4, Dw14 and DR1) have an increased prevalence of RA, perhaps leading to a genetic susceptibility to an unidentified factor which initiates the disease process. The association with DR4 is highest for Felty's Disease and severe RA (Westedt, M. L., et al., Annals of Rheumatic Diseases, 1986, 45, 534–538). Relationships between Epstein Barr virus and RA have been suggested. Synovial lymphocytes produce IgG that is recognized as foreign and stimulates a local immune response with production of anti-IgG-antibodies (rheumatoid factors). Immune complexes are formed by activation of the complement system which results in inflammation including activation of lysozyme and other enzymes. Helper T cell infiltration of the synovium and liberation of lymphokines such as IL6 lead to further accumulation of macrophages and slowly progressing joint destruction (erosions).

The approach to drug treatment in rheumatoid arthritis has been described as a pyramid ("Primer on the Rheumatic Diseases", supra). First line agents include aspirin and NSAIDS (non-steroidal anti-inflammatory drugs). When these agents fail, gold salts, penicillamine, methotrexate, or antimalarials, known as conventional second line drugs, are considered. Finally, steroids or cytotoxics are tried in patients with serious active disease that is refractory to first and second line treatment. Cyclosporine is now suggested to have a role in the treatment of patients whose disease is unresponsive to aspirin, NSAIDS, gold or penicillamine. However, the current experimental drugs to treat severe RA patients may prove too toxic even if they are effective.

Numerous efforts have been directed to developing safer and more efficacious immunotherapy to replace these toxic drugs. Severe RA patients who were treated with total lymphoid irradiation or thoracic duct drainage experienced significant improvement of disease symptoms. These procedures are not suitable for routine application. Due to these encouraging findings, however, and to the demonstration of the presence of T cells in the synovial infiltrate, it is possible to design new immunotherapies to specifically eliminate T cells. Most of these new experimental immunotherapies are targeted toward all or the bulk of T cells, and thus may produce significant side effects. A better approach for selective immunotherapy may be to eliminate only the small proportion of T cells that are involved in RA.

2.5. Role of T Cells in Rheumatoid Arthritis

Evidence has accumulated supporting a role for T-cells in the pathogenesis of rheumatoid arthritis (RA). The synovial tissue and surrounding synovial fluid of patients with rheumatoid arthritis (RA) are infiltrated with large numbers of cells. Activated and resting T cells can mediate tissue damage by a variety of mechanisms including the direct cytotoxicity of target cells expressing specific antigen in combination with the appropriate HLA restricting elements. The strong association of certain HLA products with RA has led researchers to implicate T cells in the autoimmune destruction of RA patient joints. In fact, HLA DR4, Dw4 and Dw14 gene products are among the major class II molecules that contribute significantly to disease susceptibility in RA patients (Nepom, B., et al., 1987, Abstracts of Amer. Rheumatism Assoc., p. S25; Todd, J. A., et al., 1988, Science 240:1003–1009), and they are capable of restricting antigen recognition of CD4+ T cells, primarily. Other autoimmune diseases also show a high correlation between disease susceptibility and HLA expression (Table 1).

This genetic basis of disease risk has resulted in phenotypic analysis of the T cells found within diseased joints. Previously, comparisons of T cells from RA joints and RA peripheral blood (PB) demonstrated significant differences in CD4 or CD8 phenotype, therefore implying a selection of T cells involved in disease activity. Most studies agree that synovial tissue-infiltrated T cells were mostly CD4+ helper-inducer (4B4+) cells (Duke, O., et al., 1987, Arth. Rheum., 30, 849) while the PB usually contained a mixture of CD4+ and CD8+ cells including both helper-inducer cells and suppressor-inducer cells (2H4+) (Emery, P., et al., 1987, Arth. Rheum., 30, 849). In contrast, there is additional evidence that the CD4+ infiltrate may be predominantly suppressor-inducer cells (2H4+) (Mikasaka, N., et al., 1987, Amer. Rheum. Abstracts, p. S39).

2.6. γδ Positive T Cells

γδ TCR may be the principal TCR in selected sites such as the skin or other organs. Although the function of the γδ positive T cells is largely unknown, they appear to be involved in non-MHC-restricted cytotoxicity and IFN-γ production. γδ$^+$ T cells are known to secrete a variety of lymphokines, such as TNF alpha, IL2 and IL4 (Bluestone, J. A. and Matis, L. A., 1989, J. Immunol. 142, 1785–1788). The total population of δ+ T cells can be identified by the monoclonal antibody, TCRδ1, which recognizes a major framework determinant on the δTCR (Band, H., et al., 1987, Science, 238, 682). A subset of γδ positive T-lymphocytes can be identified by the monoclonal antibodies, δTCS1 (anti-V$_δ$1; Wu, Y-J., et al., 1988, J. Immunol. 141, 1476–1479) and BB3 (anti-V$_δ$ TCR, Bottino, C., et al., 1988, J. Exp. Med., —, 491–505). A study by Grossi, C. E., et al. (Proc. Natl. Acad. Sci., 1989) indicated that δTCS1$^+$ T cells exhibit motile cell morphology and migrate in tissue culture. δTCS1$^+$ T cells were also shown to be potent killer T cells (Rivas, A., et al., 1989, J. Immunol., 142, 1840–1846).

3. SUMMARY OF THE INVENTION

The present invention is directed to monoclonal antibodies which recognize defined regions of the T cell antigen receptor (TCR). The antibodies of the invention bind to epitopes of the variable, diversity, joining, and/or constant regions of the alpha, beta, gamma, or delta chains of the T cell antigen receptor.

In a specific embodiment, the invention provides monoclonal antibodies which are reactive with a constant region of the alpha chain of the TCR. In particular embodiments, the invention relates to the two monoclonal antibodies, termed αF1 and αF2, which react with two different epitopes on the framework, or constant, region of the α monomer of the TCR molecule. In various embodiments of the invention, αF1 or αF2, or both, or fragments or derivatives thereof, can be used to bind to the a TCR constant region amino acid sequences, either as part of an intact TCR complex or α peptide, or a fragment thereof.

In another specific embodiment, the invention is directed to monoclonal antibodies reactive with a variable region of the beta chain of the TCR. In a preferred embodiment of the invention, the monoclonal antibodies react with a "minor framework" region of the TCR beta chain, and thereby recognize a subpopulation of T cells. In particular, the invention provides two monoclonal antibodies, termed W112 and 2D1, which react with β-chain variable regions Vβ5.3 and Vβ8.1, respectively, and thereby recognize between 0.3 to 5% and 0.5 to 13% of peripheral blood lymphocytes, respectively. In various embodiments of the invention, W112 or 2D1, or fragments or derivatives thereof, can be used to bind with βTCR variable region amino acid sequences, either as part of an intact TCR or peptide, or T cell-surface molecule, or a fragment thereof.

In another specific embodiment, the invention is directed to monoclonal antibodies reactive with a variable region of the delta chain of the TCR. In a preferred embodiment of the invention, the monoclonal antibodies react with the Vδ1 region of the TCR delta chain, and thereby recognize a subpopulation of T cells.

In a further specific embodiment, the invention is directed to a particular monoclonal antibody, δTCS1, which is of the IgG2a isotype.

The monoclonal antibodies of the invention have value in the diagnosis and therapy of conditions and diseases affecting the immune system.

In particular embodiments of the invention, rheumatoid arthritis or Felty's syndrome may be diagnosed by detecting increased percentages of total T cells which express certain delta or beta chain T cell receptor variable region genes in a patient sample. In specific embodiments of the invention, rheumatoid arthritis may be diagnosed by detecting increased percentages of total T cells which express Vδ1, Vβ3, Vβ9, or Vβ10 T cell receptor variable regions in a patient sample. In a preferred embodiment of the invention, rheumatoid arthritis may be diagnosed by detecting increased percentages of total T cells which are δTCS1 positive in a patient sample.

In further particular embodiments of the invention, rheumatoid arthritis may be treated by administering a therapeutically effective amount of a monoclonal antibody, or fragment or derivative thereof, which recognizes an epitope of the variable region of the beta chain or the delta chain of a T cell antigen receptor. According to specific embodiments, monoclonal antibodies which recognize epitopes of Vδ1, Vβ3, Vβ9, or Vβ10 variable regions of the T cell antigen receptor may be used to treat rheumatoid arthritis.

The invention also provides for therapeutic compositions comprising the monoclonal antibodies of the invention.

3.1. Abbreviations and Definitions

As used herein, the following terms will have the meanings indicated:

C=constant
D=diversity
ELISA=enzyme linked immunosorbent assay
J=joining
mAb=monoclonal antibody
PBL=peripheral blood lymphocytes
PMA=phorbol 12-myristate 13-acetate
SDS-PAGE=sodium dodecylsulfate polyacrylamide gel electrophoresis
TCR=T cell antigen receptor
V=variable
anti-clonotypic antibody=an antibody that reacts solely with the T cell clone against which it was raised. Also referred to as an anti-idiotypic antibody.
anti-minor framework antibody=an antibody that reacts with a minor framework determinant present on a subset of T cells. Anti-minor framework antibodies recognize small percentages of PBLS, i.e., less than 20% in a normal subject. Anti-minor framework antibodies can be used to define closely related TCRs or TCR families.

anti-major framework antibody=an antibody that reacts with a major framework determinant present on a large population of T cells. Anti-major framework antibodies will recognize at least 20% of PBLs in a normal subject.

RES=reticuloendothelial system.
RA=Rheumatoid Arthritis
PB=peripheral blood
ST-line=RA synovial tissue-derived T cells
PB-T=peripheral blood-derived T cells
FS=Felty's Syndrome
SSA=Seronegative Spondyloarthropathies
EBV=Epstein-Barr virus
PBS=phosphate buffered saline
NK=natural killer
NST-line=non-RA synovial tissue-derived T cells
HLA=human leukocyte antigen

4. DESCRIPTION OF THE FIGURES

FIG. 1. Immunoprecipitation of $^{125}$I labeled HPB-cell lysates and Molt-13 cell lysates. HPB- and Molt-13 cells were surface labeled with $^{125}$I and lysed in 1% NP-40. Cell lysates were incubated with mAb and the precipitated immune complex was applied to 10% SDS-PAGE. Electrophoresis was run under non-reducing (A) and reducing conditions (B). The precipitated TCR proteins were detected by autoradiography.

Figure 2:
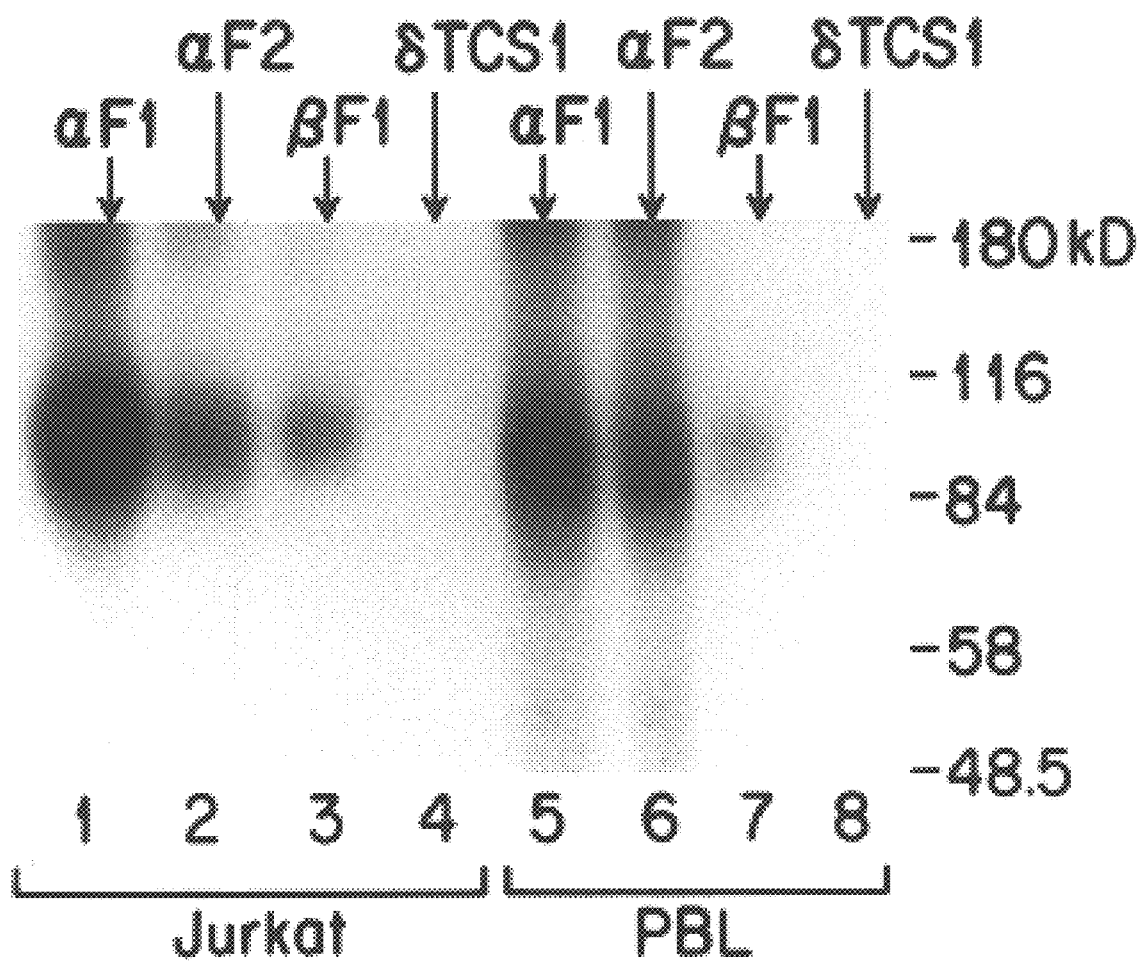
Figure 3A:
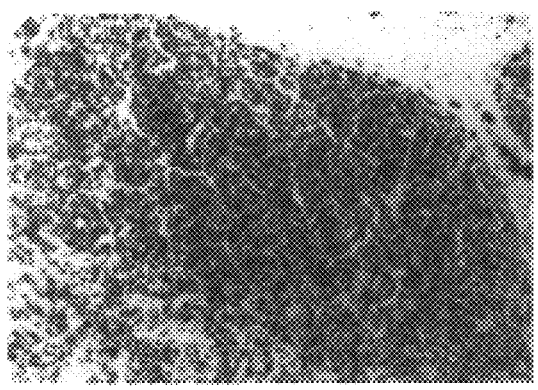
Figure 3B:
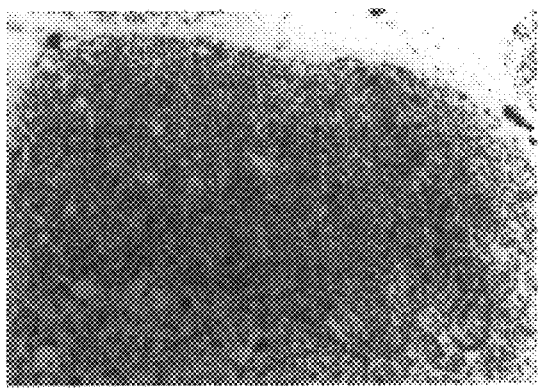
Figure 3C:
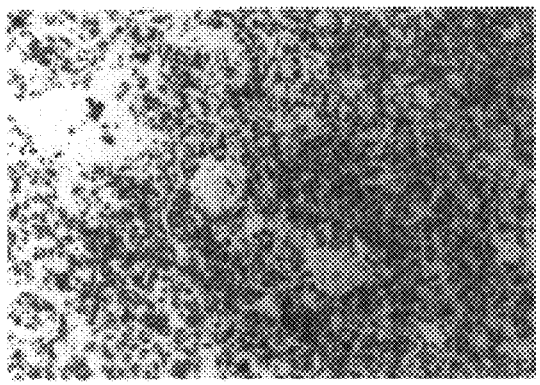
Figure 3D:
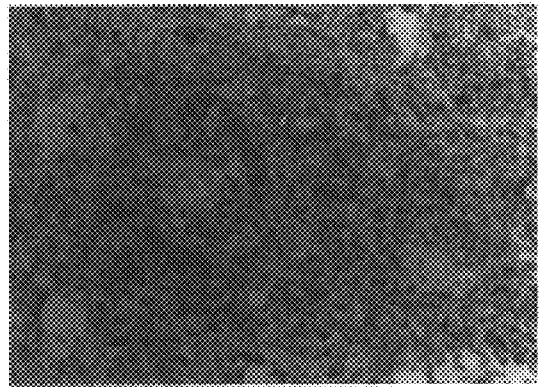
Figure 3E:
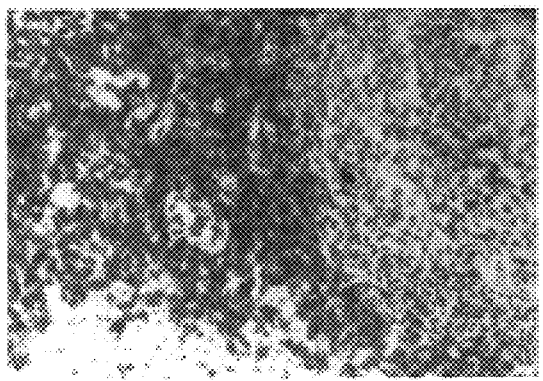
Figure 3F:
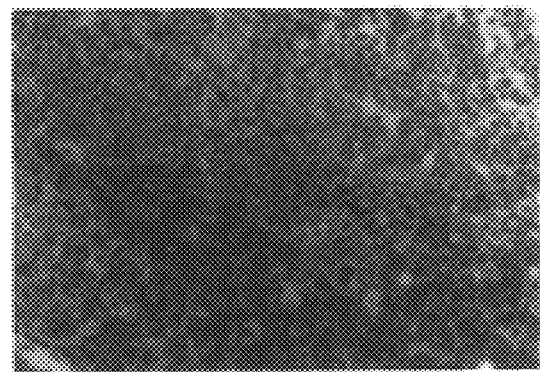

FIG. 2. TCR immunoprecipitation from Jurkat cells and PBL with αF1 and αF2. $^{125}$I labeled Jurkat cells and PBL were lysed in 1% NP-40 and incubated with αF1 and αF2 and control mAb. The immune complex precipitated was revealed by 10% SDS-PAGE under non-reducing conditions.

βF1 antibody was a positive control for immunoprecipitating the αβTCR. δTCS1 antibody reacts with δγ$^+$ cells, not ab$^+$ cells.

FIG. 3. Immunoperoxidase staining of human thymus and tonsilar tissue. A and B are thymus cortex; C and D are thymus medulla; E and F are human tonsil. βF1 stains about 70% of cells in cortex (A), over 90% in medulla (C) and all T cells in the interfollicular region of tonsil (E). A similar staining pattern is observed when αF1 is used (B, D, and F). Note that αF1 stains less thymus cortex cells (B).

FIG. 4. Competition assay of TCRα peptides with HPB-TCR. Two-fold dilutions of free α141–159 (amino acids 141–159 of TCRα)(open circle) or α212–231 (amino acids 212–231 of TCRα)(solid circle) were mixed with 10% HPB-lysates and incubated with αF1 (a) or αF2 (b) in a TCR-ELISA assay. Peptide concentration is shown on the X-axis in logarithmic scale. αF1 and αF2 were used at 4 μg/ml.

Figure 5:
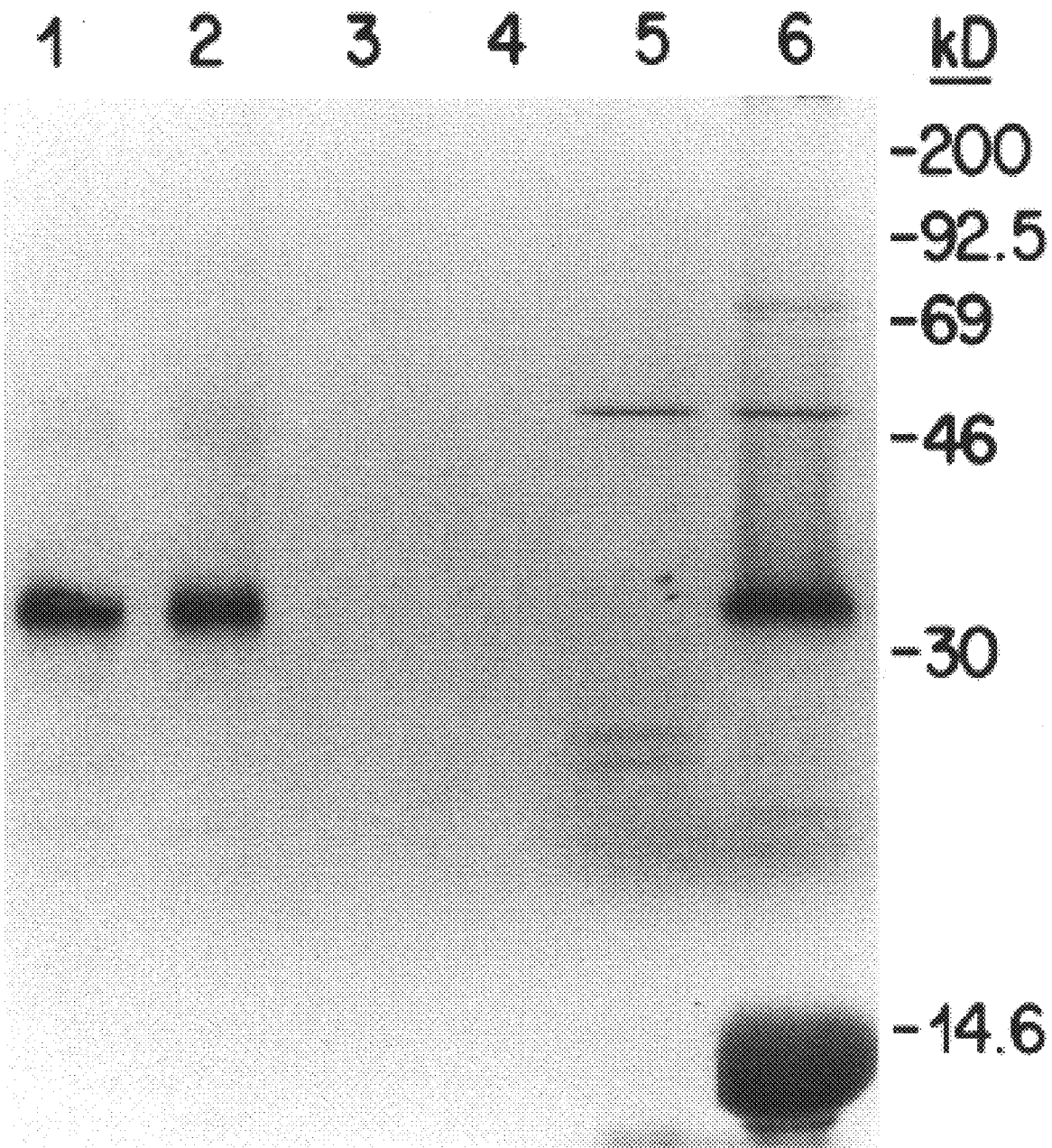

FIG. 5. Immunoprecipitation of in vitro translated α chain T cell antigen receptor protein with mAb αF1 and αF2. Aliquots of protein mixture containing both α chain and rabbit globin (lane 6) were immunoprecipitated separately with anti-Cα antibodies, αF1 (lane 1) and αF2 (lane 2), and isotype matched, irrelevant antibodies in lane 3 and lane 4. Lane 5, in vitro translation in the absence of any exogenous RNA. Samples were analyzed on a 12.5% SDS-PAGE which was dried and subsequently autoradiographed.

FIG. 6. A. A schematic of the hybridoma screening ELISA. Microtiter plate wells were coated with goat anti-mouse Ig Fc and washed to remove unbound reagent. Non-specific sites were blocked with bovine serum albumin. Aliquots of hybridoma supernatants were added to the wells with blocking buffer, incubated, and followed by washing to remove unbound proteins. NP40 generated cell lysates from αβ TCR cell lines were added, wells were washed, and biotin-conjugated βF1 F(ab)$_2$ was added. After washing to remove unbound reagent, HRP conjugated streptavidin was added, wells were washed, and color was developed using an HRP substrate, o-phenylenediamine.

B. Comodulation assay: Jurkat cells were incubated with antibodies overnight, washed, incubated with FITC-labeled OKT3 and analyzed by flow cytometry. Antibody 2D1 caused a dramatic reduction (over 90%) of OKT3 surface staining. C305, an anti-Jurkat IgM isotype antibody and OKT3 also modulated the CD3 expression, while isotype-matched control antibody W4 did not. This data indicated that the epitope recognized by 2D1 is on the CD3-TCR complex.

FIG. 7. A. Immunoprecipitation of HPB with W112 and control antibodies under non-reducing conditions followed by SDS-PAGE under reducing conditions. W112 and βF1 precipitated the αβ TCR heterodimer of 48 kD (α) and 40 kD (β). Normal mouse serum did not precipitate the αβ TCR heterodimer.

B. Immunoprecipitation of Jurkat cell lysates with 2D1 and control antibodies under non-reducing conditions followed by SDS-PAGE under reducing conditions. 2D1 precipitated the α,β TCR heterodimer of 48 kD (α) and 40 kD (β). βF1 and αF1 precipitated the same 48 kD and 40 kD bands, while negative control antibody δTCS1 did not.

Figure 8:
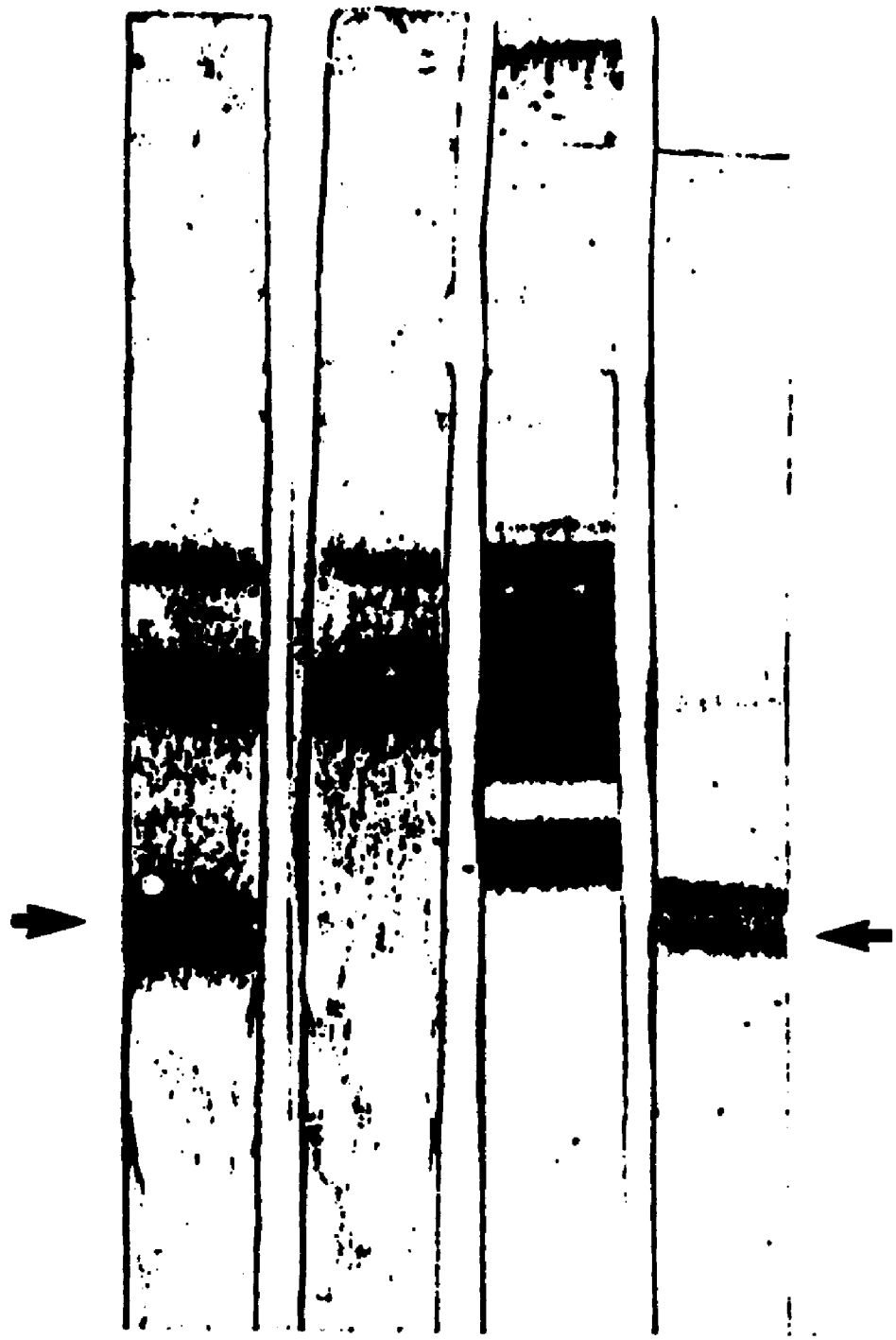

FIG. 8. Western blot analysis using HPB cell membranes. W112 recognized the 40 kD TCR β chain protein as indicated by the arrow. βF1 also detected the 40 kD band. Normal mouse serum did not react with this band. αF1 detected a different band of a higher molecular weight.

Figure 9:
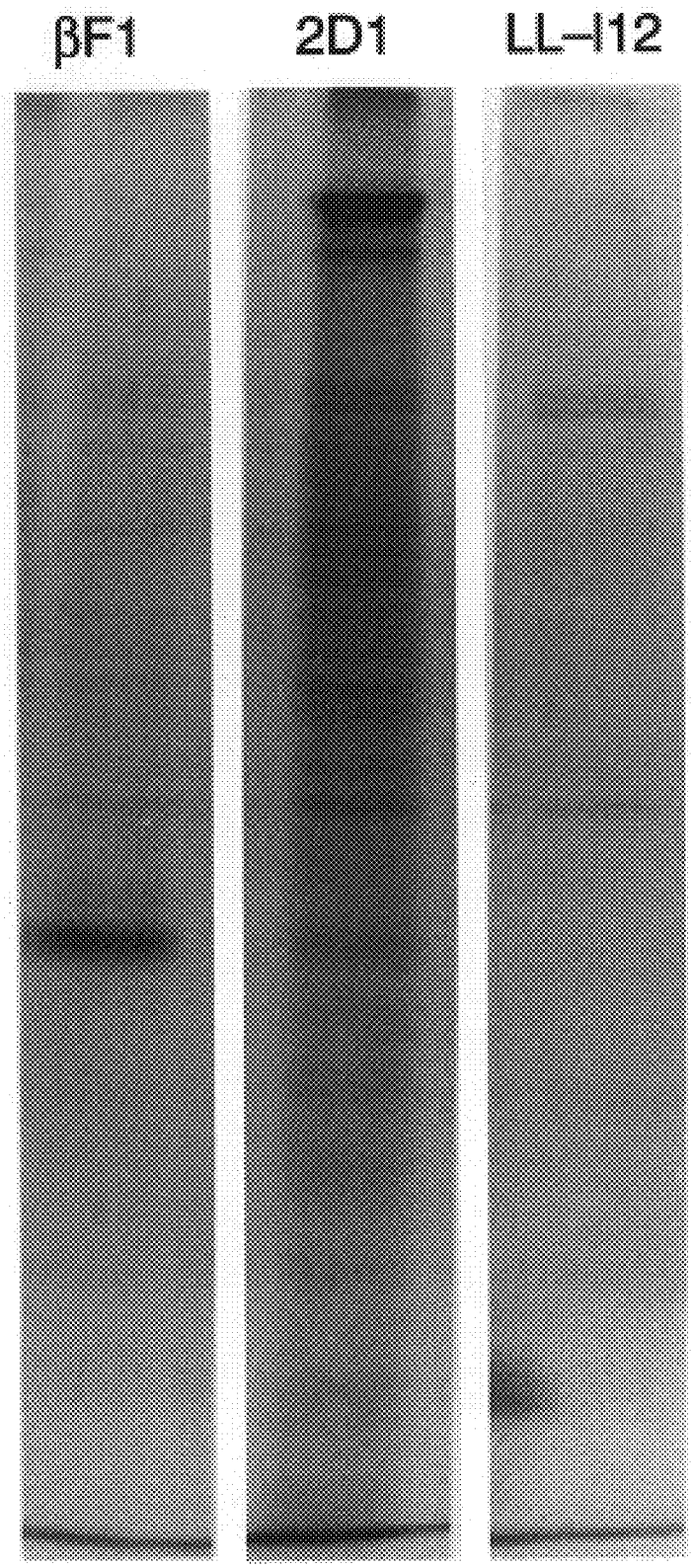

FIG. 9. Immunoprecipitation of metabolically labelled Jurkat cell lysates. 2D1 precipitated the 40 kD β chain TCR, as did βF1. Isotype-matched negative control antibody LL-112 was unreactive.

Figure 10:
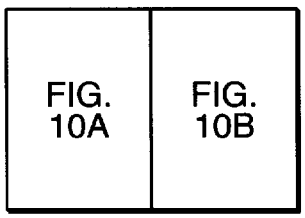
Figure 10A:
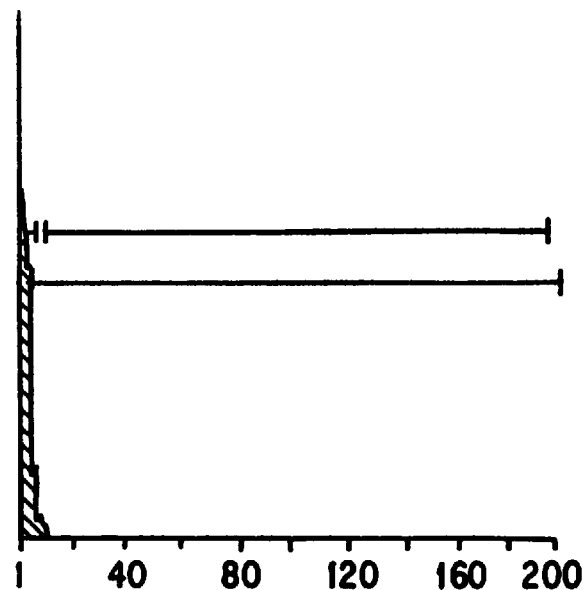
Figure 10A:
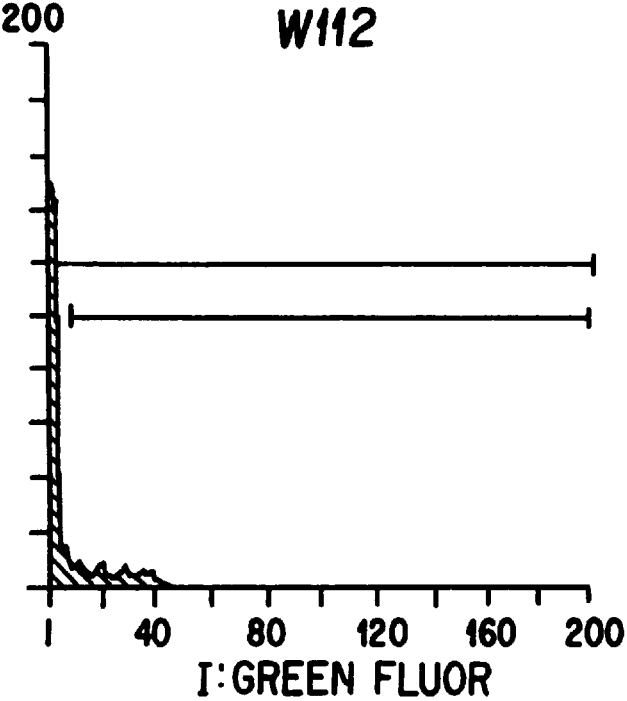
Figure 10B:
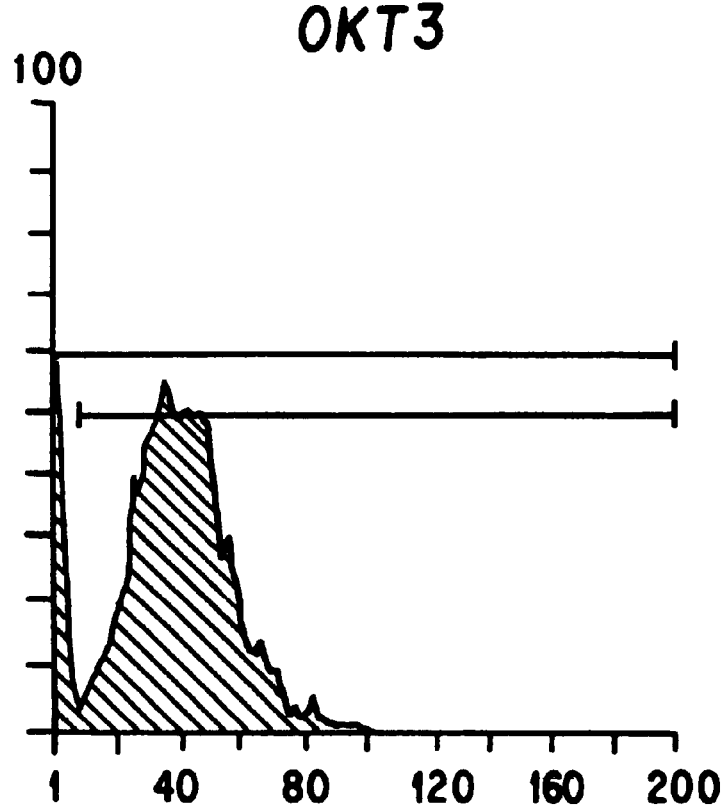
Figure 10B:
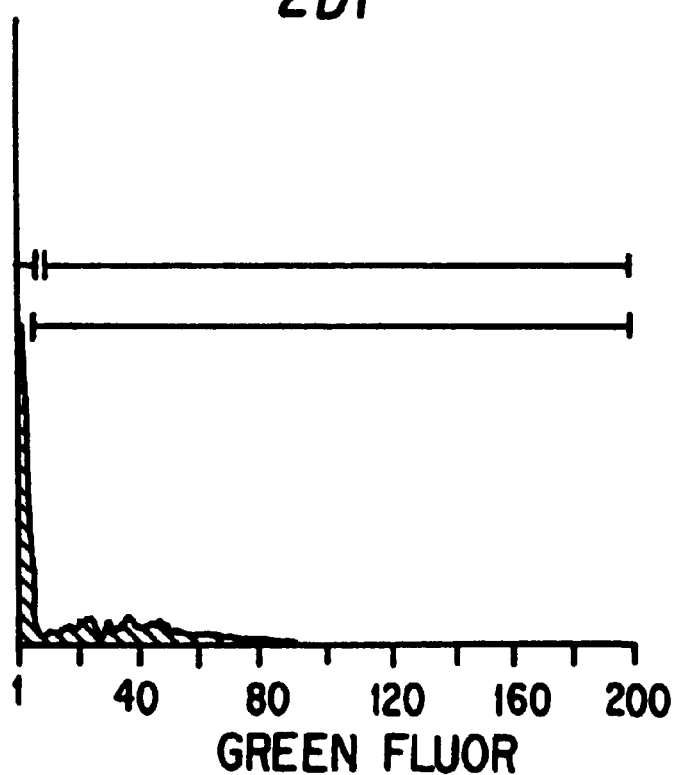

FIG. 10. Flow cytometric analysis of peripheral blood lymphocytes (PBLs) from one normal donor using W112 and 2D1 antibodies. The positive control pan-T monoclonal antibody OKT3 stained 70% of the PBLs. W112 stained a small subpopulation consisting of 3% of the PBLs and 2D1 stained a small subpopulation of 5.5% PBLs. Normal mouse serum did not react with any of the PBLs.

Figure 11:
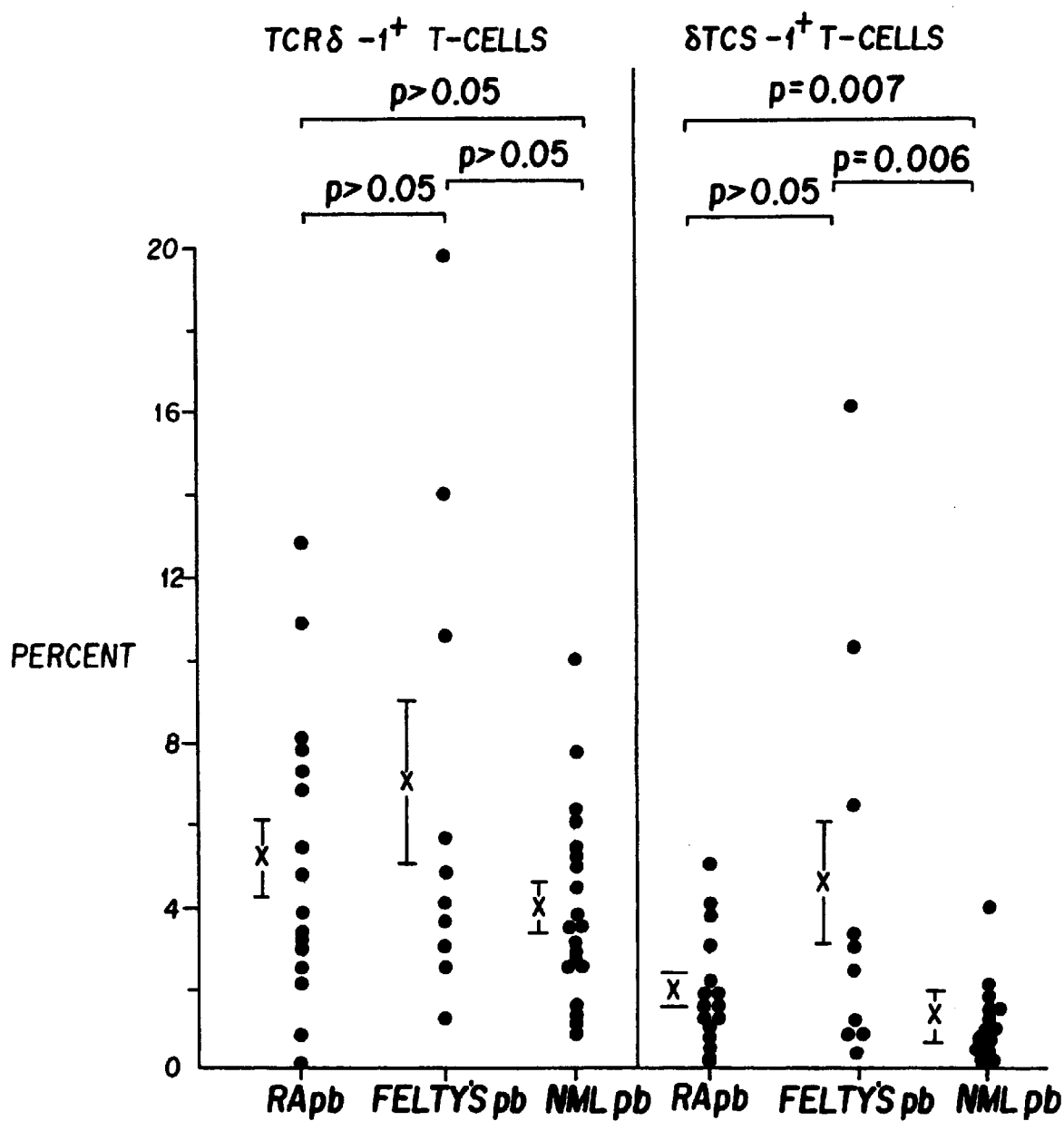

FIG. 11. Levels of TCRδ bearing T cells (left panel) and δTCS1 bearing T cell (right panel) in the PB of patients with RA, FS and NML. Arithmetic mean values are represented by the 'X' and the error bars represent ±1 standard error (S.E.).

Figure 12:
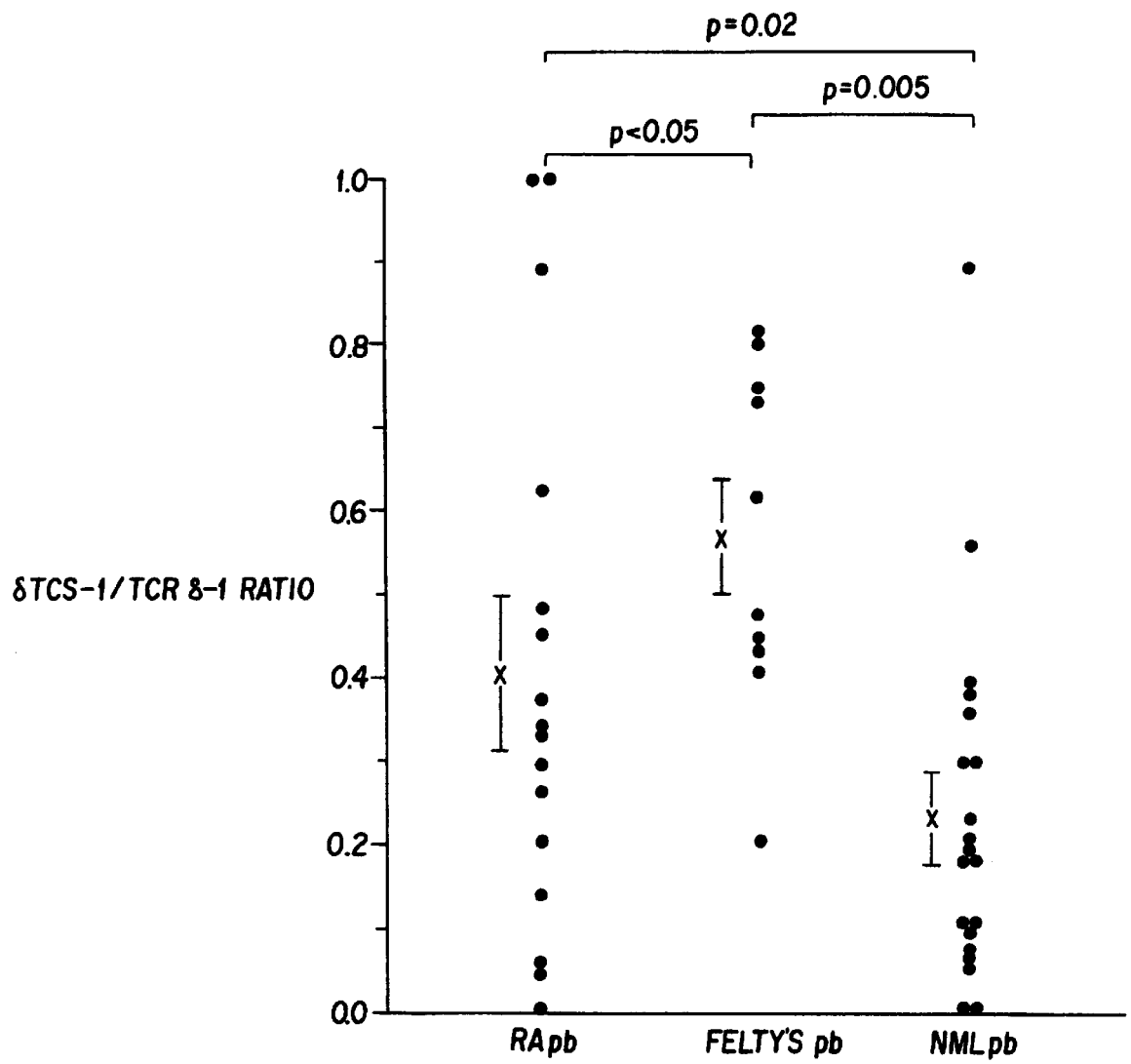

FIG. 12. Ratio of δTCS1/TCRδ1 bearing T cells in patients with RA, FS and NML. Notations as per FIG. 11.

Figure 13:
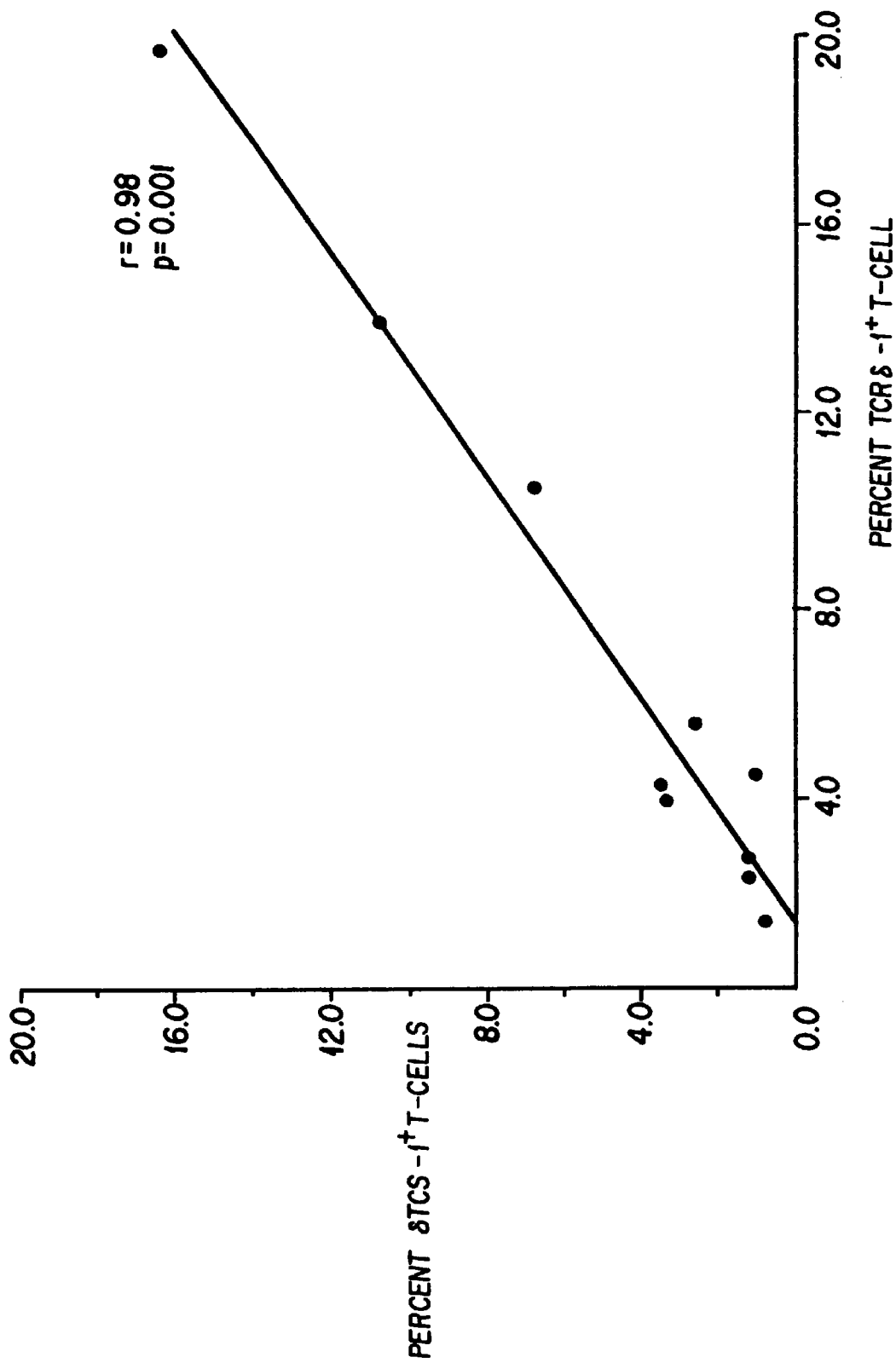

FIG. 13. Relationship between the percent of TCRδ1 T cells and the percent of δTCS1 T cells in patients with FS.

Figure 14B:
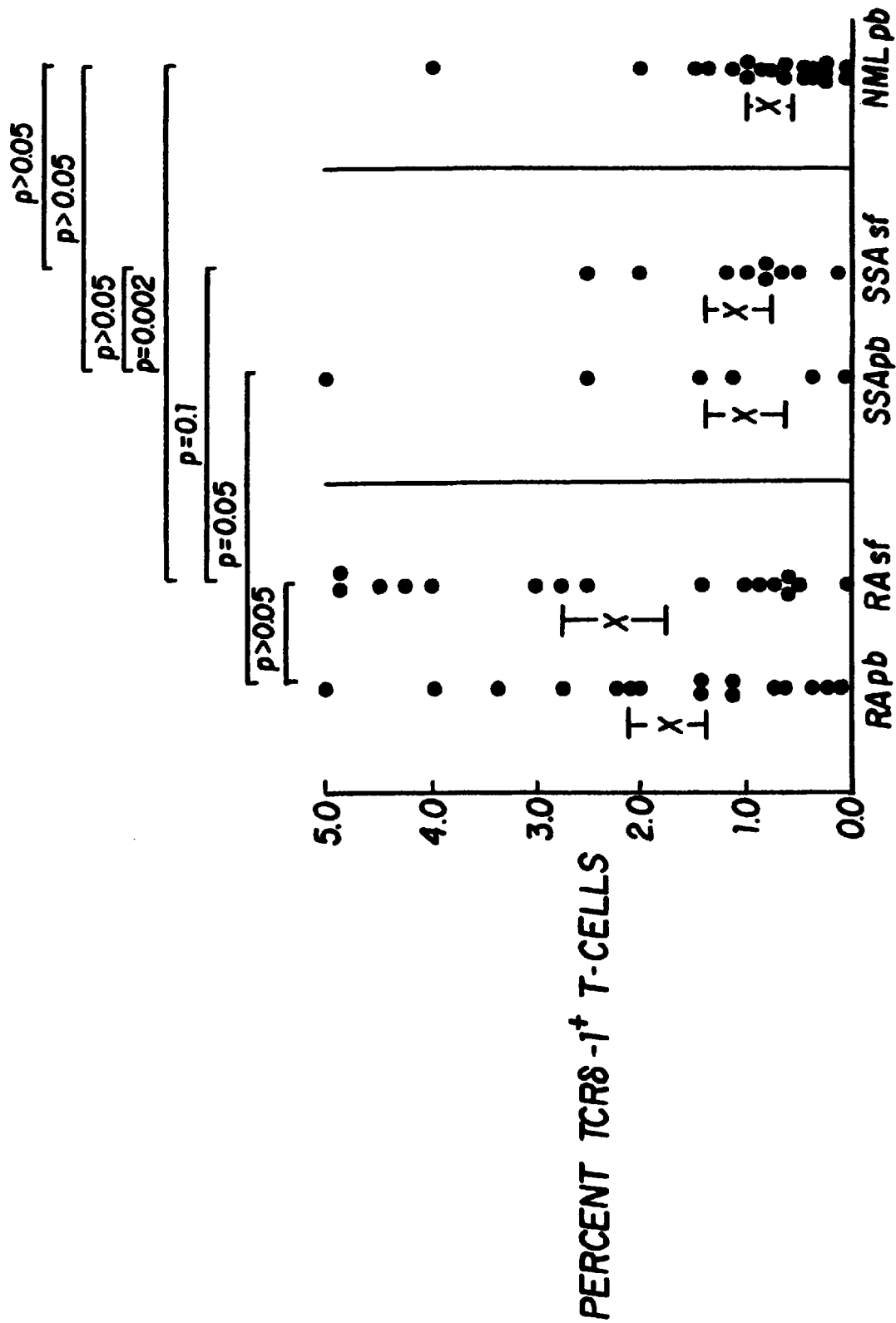

FIG. 14. Levels of TCRδ1 bearing T cells (upper panel) and δTCS1 bearing T cells (lower panel) in the PB and SF of RA and SSA patients. Notations as per FIG. 11.

Figure 15:
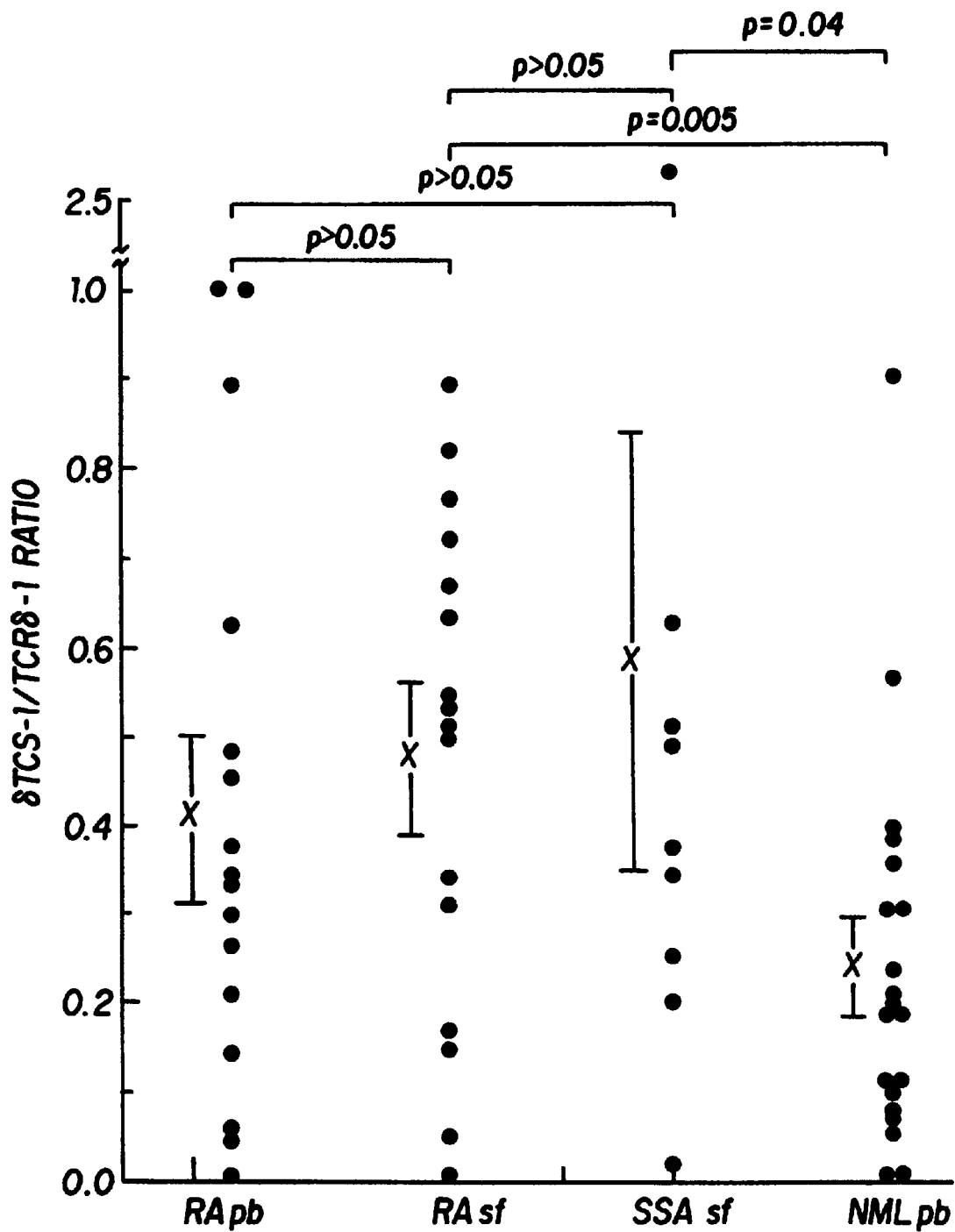

FIG. 15. Ratio of δTCS1/TCRδ1 bearing T cells in the PB and SF of RA patients and SF of patients with SSA. Notations as per FIG. 11.

Figure 16:
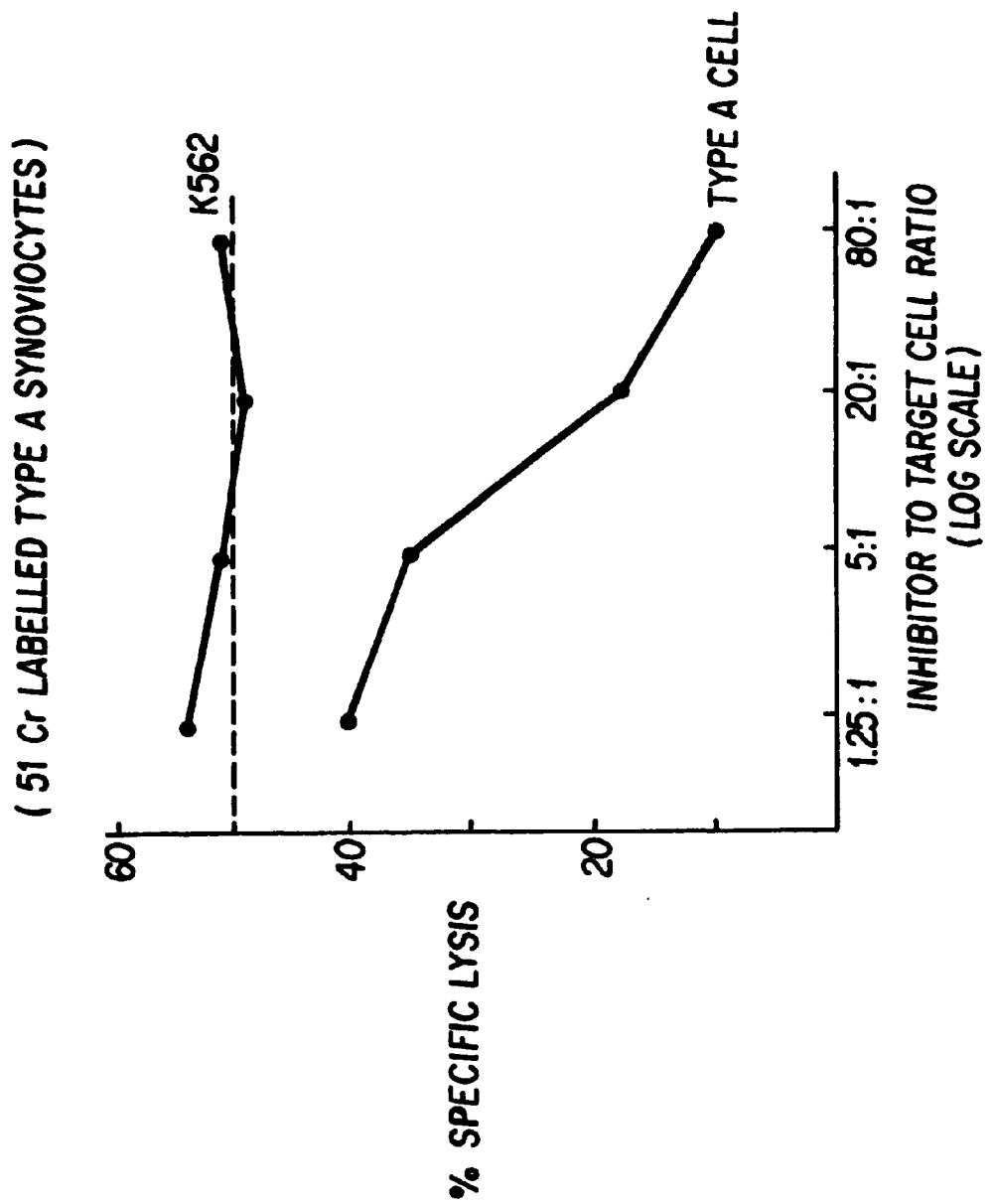

FIG. 16. Synovial derived T cell (ST-13) cytotoxicity of type A synovial target cells and the cold target inhibition by K562. Effector to $^{51}$Cr labelled target cell ratio was 1:1 while increasing concentrations of unlabelled target cells were added. The standard deviations did not exceed 4%. The spontaneous $^{51}$Cr release for ST-13 type A synoviocytes was 38%.

Figure 17:
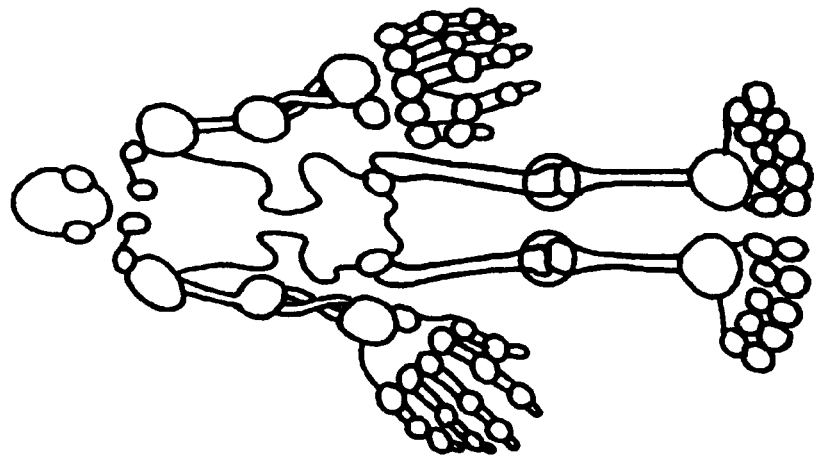

FIG. 17. Assessment of patient benefit. There are several standard criteria to assess whether arthritis patients are benefiting from treatment. At each visit, patients are scored according to the ten criteria listed and an overall additive score is determined. This score is used to establish the effectiveness of the drug treatment. Other parameters can also be measured. These include blood counts, liver function tests, Westegren sedimentation rates, rheumatoid factor tests, etc.

Figure 18:
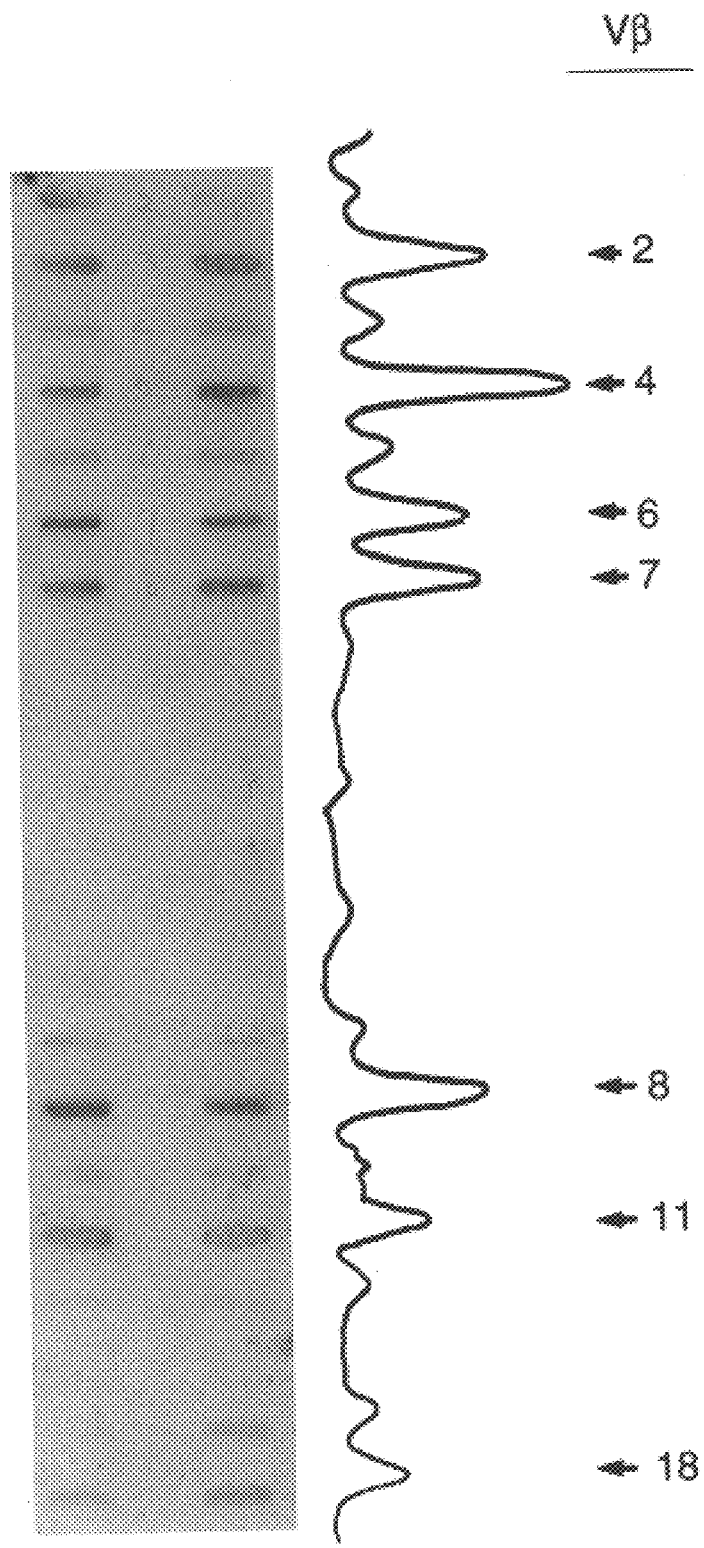

FIG. 18. Analysis of Vβ Gene Usage in Synovial Tissue Derived T Cell Line. Line ST-2, derived from the synovial membrane infiltrating cells of a rheumatoid arthritis patient, was analyzed for TCR Vβ expression using the cDNA, PCR amplification, slot blot hybridization protocol. The left part of the figure represents the autoradiograph obtained when the panel of Vβ genes was hybridized with the ST-2 amplified TCR specific cDNA probe. The right part of the figure is the densitometry trace of the autoradiograph.

Figure 19:
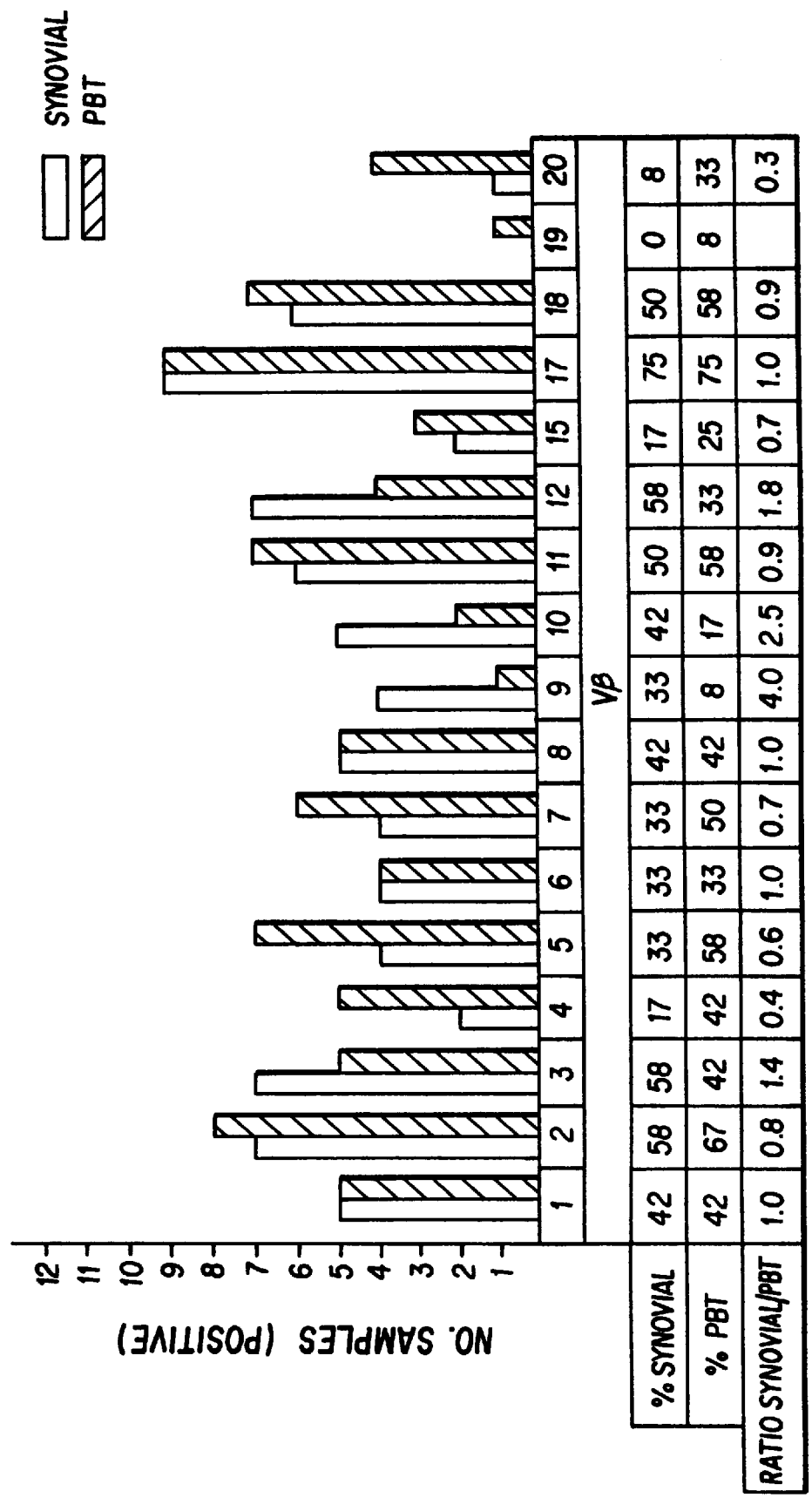

FIG. 19. Detection of Vβ Gene Usage in Rheumatoid Arthritis T Cells. This figure is a tabulation of the results of the expression of the panel of Vβ genes in 12 paired synovium tissue derived and peripheral blood derived T cell lines from rheumatoid arthritis patients. For the top part of the figure, the vertical axis represents the number of samples that were positive for a particular Vβ. The individual Vβ genes are indicated on the horizontal axis. Data derived from synovial T cells and peripheral blood T cells are plotted in pairs as the open and crosshatched bars, respectively. For the bottom part of the figure, the frequencies of the individual Vβ genes in the 12 patient samples are shown (% synovial and % PBT). To indicate preferential usage of Vβ genes the ratio of occurrence in the synovial/peripheral blood samples is shown.

Figure 20:
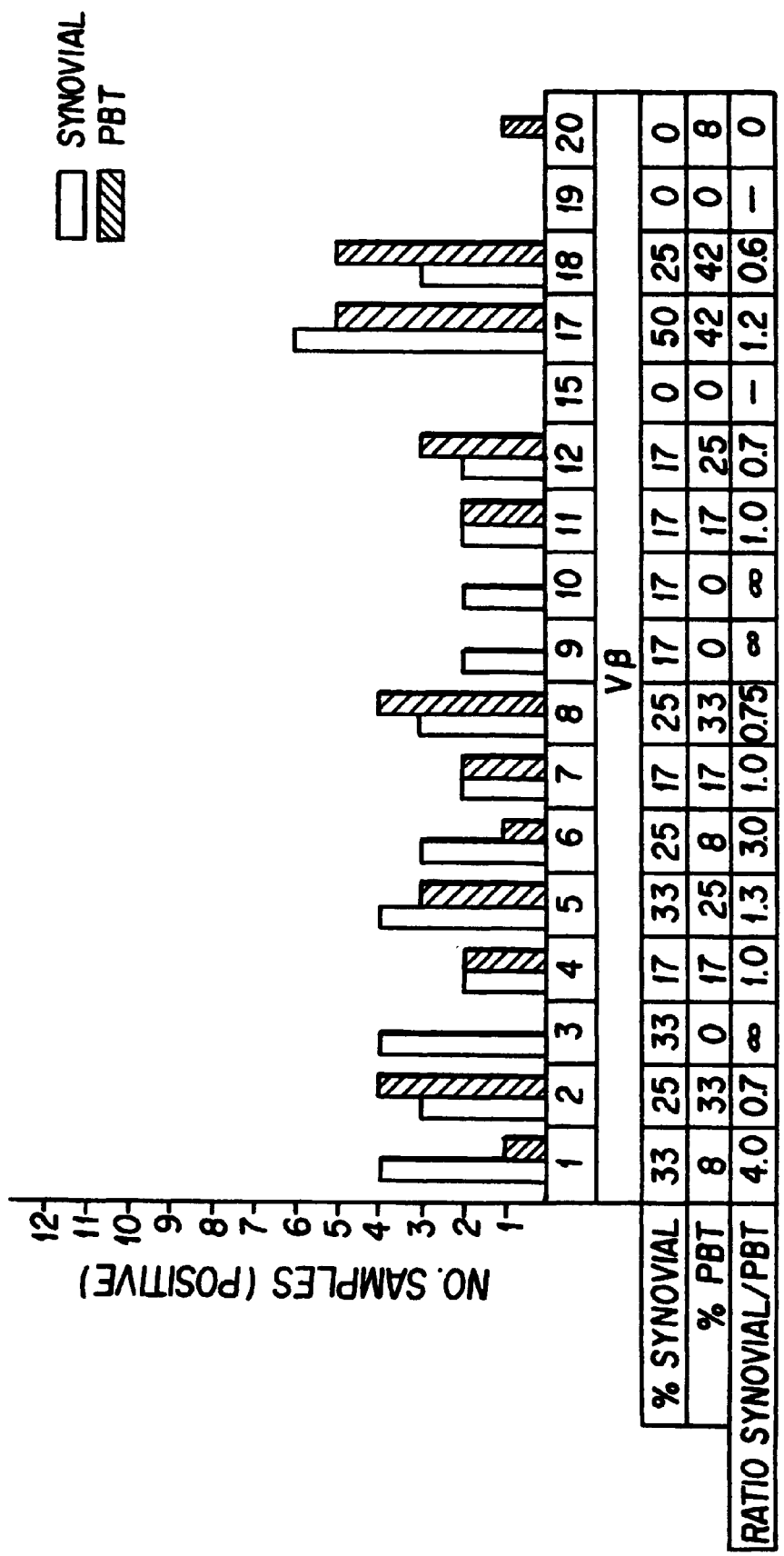

FIG. 20. Detection of Dominant Vβ Gene Usage in Rheumatoid Arthritis T Cells. This figure is similar to FIG. 19, except that the tabulated data includes only the expression of the most frequently occurring Vβ genes as determined by the densitometry trace. The most frequent or dominant Vβ was determined from the highest peak height which was used as a standard. Any Vβ gene with a corresponding densitometry peak with height greater than 50% of the standard was used in the tabulation.

Figure 21:
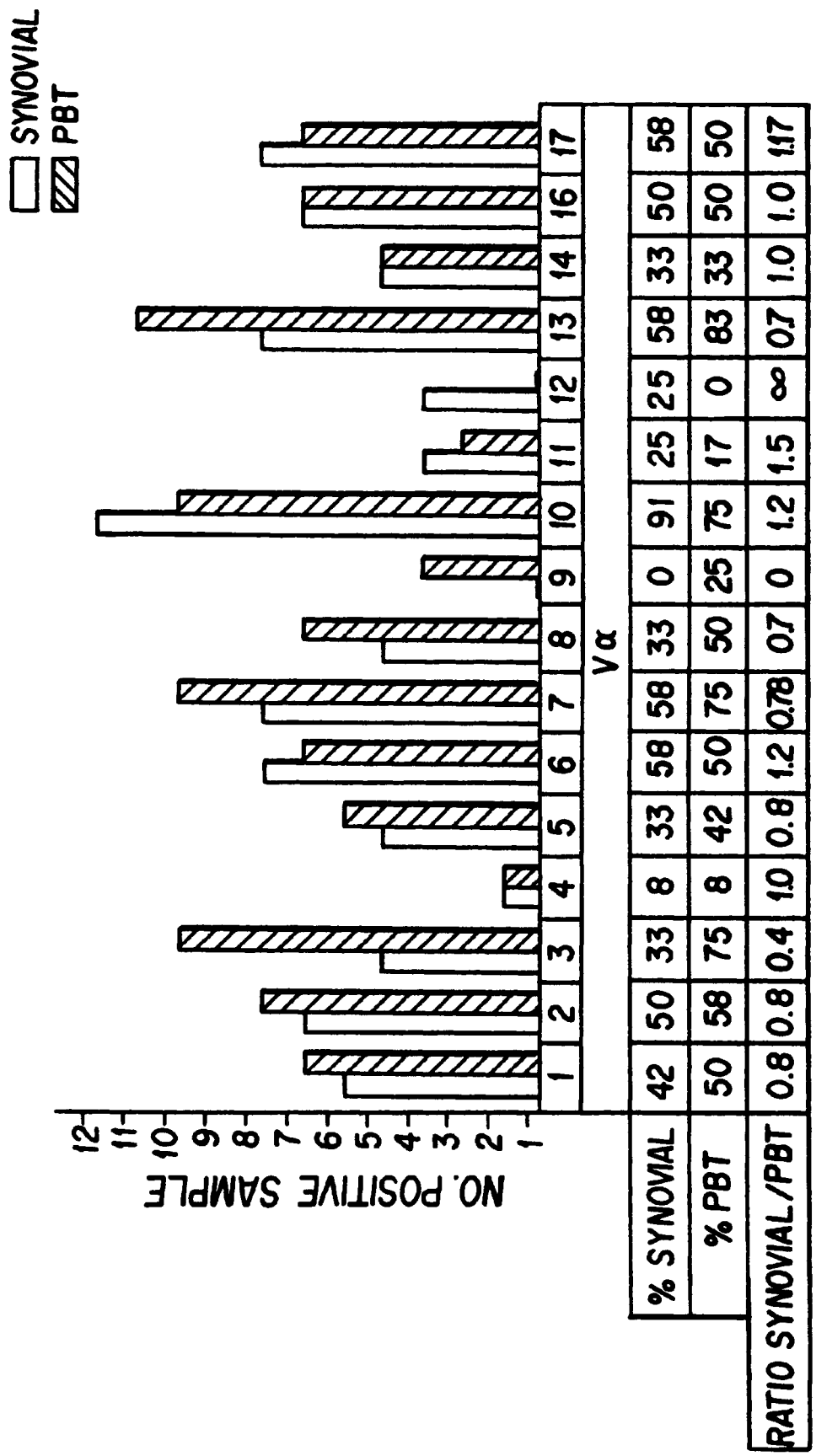

FIG. 21. Detection of Vα Gene Usage in Rheumatoid Arthritis T Cells. This figure is similar to FIG. 19, except the patient samples were analyzed for Vα gene expression. The data in this figure represents the total Vα expression observed, not the dominant or most frequently expressed Vα. 85% of the T cell samples tested expressed Vα10 at a densitometry peak height 100-fold greater than for the other Vα genes.

Figure 22:
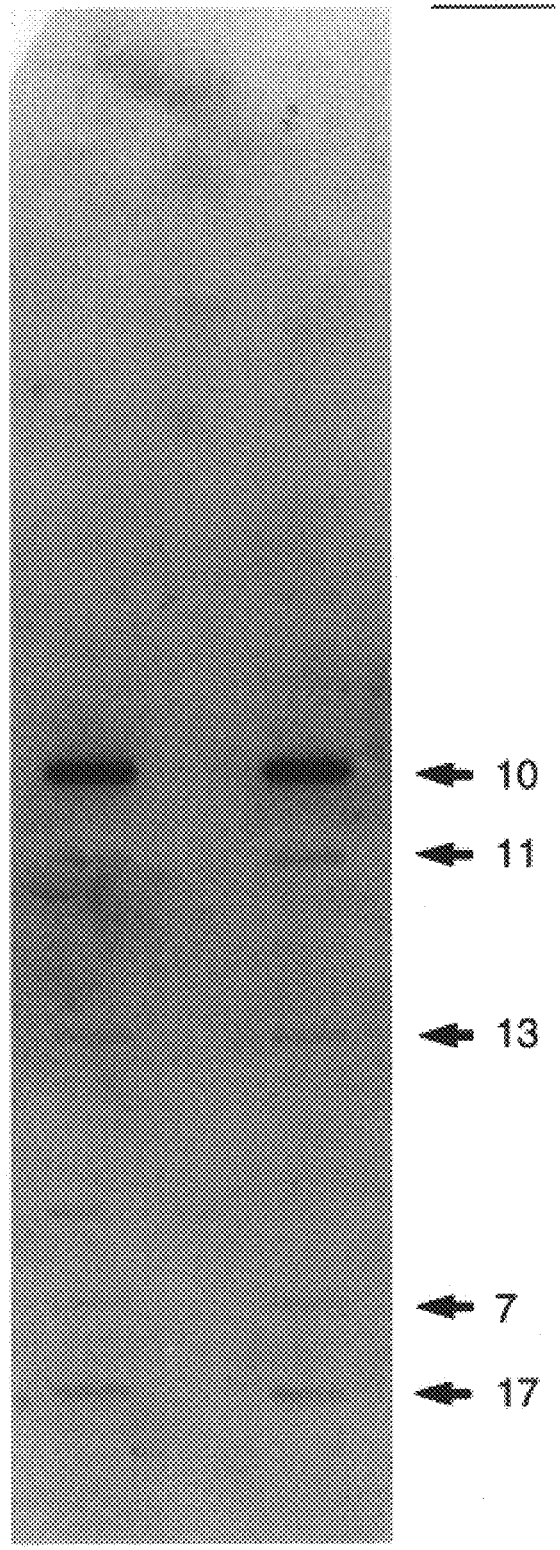

FIG. 22. Vα Gene Usage in the Synovial Tissue Derived T Cell Line ST-5. The dominantly expressed Vα gene is Vα10, although other Vα genes are expressed as minor populations.

5. DETAILED DESCRIPTION OF THE INVENTION

The present invention is directed to monoclonal antibodies which recognize defined regions of T cell antigen receptor (TCR) chains. Such antibodies bind to epitopes of the variable, diversity, joining, and/or constant regions of the alpha, beta, gamma, or delta chains of the T cell antigen receptor. As used herein, a monoclonal antibody reactive with the "variable region" of the TCR shall be construed to be a monoclonal antibody reactive with an epitope of the V region or a combination epitope of the V region or a combination epitope of the V-D or V-D-J regions; a monoclonal antibody reactive with a "variable region" of TCR may recognize an idiotype, a clonotype, or, preferably, may recognize a minor framework region expressed by a subgroup of T lymphocytes. The term minor framework region refers to a region of the TCR which is not shared by all TCR molecules, but is also not unique to a particular clone of T cells. In a specific embodiment, the monoclonal antibodies of the invention are reactive with a constant region of the alpha chain of the T cell antigen receptor. In another embodiment, the monoclonal antibodies are reactive with a variable region of the beta chain of the T cell antigen receptor. In particular, such an anti-TCRβ mAb can recognize Vβ5.3. In another particular embodiment, such an anti-TCRβ mAb can recognize Vβ8.1. In another embodiment, the monoclonal antibodies are reactive with a variable region of the delta chain of the T cell antigen receptor. In particular such an anti-TCRδmAb can recognize Vδ1.

The monoclonal antibodies of the invention, and fragments, derivatives, and analogues thereof, have uses in diagnosis and therapy.

In specific embodiments of the invention, monoclonal antibodies which bind to Vδ1, Vβ3, Vβ9, or Vβ10 variable regions of the T cell antigen receptor may be utilized in the diagnosis and therapy of rheumatoid arthritis.

5.1. Generation of Monoclonal Antibodies Reactive With Defined Regions of the T Cell Antigen Receptor The monoclonal antibodies of the invention are directed to an epitope of a defined region of the T cell antigen receptor. A monoclonal antibody to an epitope of the T cell can be prepared by using any technique which provides for the production of antibody molecules by continuous cell lines in culture. These include but are not limited to the hybridoma technique originally described by Kohler and Milstein (1975, Nature 256:495–497), and the more recent human B cell hybridoma technique (Kozbor et al., 1983, Immunology Today 4:72), EBV-hybridoma technique (Cole et al., 1985, Monoclonal Antibodies and Cancer Therapy, Alan R. Liss, Inc., pp. 77–96), and trioma techniques.

In one embodiment, the monoclonal antibodies may be of human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:7279; Olsson et al., 1982, Meth. Enzymol. 92:3–16). Chimeric antibody molecules may be prepared containing a mouse (or rat, or other species) antigen-binding domain with human constant regions (Morrison et al., 1984, Proc. Natl. Acad. Sci. U.S.A. 81:6851; Takeda et al., 1985, Nature 314:452). For therapeutic purposes, antibodies can be further humanized, by producing human constant region chimeras, where the conserved or framework regions of the antigen-binding domain are also from human sequences, and only the hypervariable regions are non-human.

As part of the production of the monoclonal antibodies of the invention, various host animals, including but not limited to rabbits, mice, and rats can be immunized by injection with purified T cell antigen receptors or polypeptides or fragments thereof, a recombinant or synthetic version thereof, or T lymphocytes.

Various cell lines can be used as immunogens to generate monoclonal antibodies to the V region of human T cell antigen receptors, including, but not limited to, those cell lines listed in Table 4 (Toyonaga et al., 1987, Ann. Rev. Immunol. 5: 585–620). Any T cell line could be used, including any γδ+ cell line, such as (but not limited to) PEER, MOLT 13, WM 14, AK119, etc., provided that TCR is expressed on the cell surface, as in the MOLT 13 cell line. Note that antibodies to known V, D, J, DJ, VJ, VDJ or combinations thereof can also be generated by immunizing with these cell lines. V, D, J, and C region α, β, γ or δ expression can be determined in any cell line by well known procedures including cDNA sequencing, in situ hybridization, polymerase chain reaction analysis, Northern analysis, Southern analysis, immunoassay, or flow cytometry, to name but a few.

Whole cells that can be used as immunogens to produce TCR specific antibodies also include recombinant transfectants. For example, β⁻ Jurkat cells can be reconstituted by transfection with an β cDNA to produce intact αβ TCR on the cell surface (Ohashi, P. S., et al., Nature, 316:606–609). These transfectant cells could then be used as immunogen to produce α or β TCR antibodies of preselected specificity. Other examples of such transfectant cells have been reported (Kaye, J. and Hedrick, S. H., 1988, Nature 336:580–583; Dembic, Z., et al., 1986, Nature 320: 232–238; Saito, T., et al., 1987, Nature 325:125–130), but any procedure that works to express transfected TCR genes on the cell surface could be used to produce the whole cell immunogen. This includes, but is not limited to, eukaryotic expression systems utilizing a phospholipid anchor domain (International Patent Application no. PCT/US88/02648 published Feb. 9, 1989).

Screening procedures that can be used to screen hybridoma cells expressing different anti-TCR antibodies include but are not limited to (1) enzyme linked immunosorbent assays (ELISA), (2) flow cytometry (FLOW) analysis, (3) immunoprecipitation, and (4) the ability to comodulate the CD3 antigen (part of the TCR-CD3 complex present on the surface of T cells) off of the surface of cells. The comodulation and FLOW screening procedures are preferred for the selection of antibodies potentially useful in therapy since these procedures will result in selection of antibodies that are able to recognize intact TCR on live cells due to the inherent properties of these techniques.

Many different formats of an ELISA that can be used to screen for anti-TCR antibodies can be envisioned by one skilled in the art. These include, but are not limited to, formats comprising purified, synthesized or recombinantly expressed TCR polypeptide attached to the solid phase or bound by antibodies attached to the solid phase or formats comprising the use of whole T cells or T cell lysate membrane preparations either attached to the solid phase or bound by antibodies attached to the solid phase. Samples of hybridoma supernatants would be reacted with either of these two formats, followed by incubation with, for instance, a goat anti-mouse immunoglobulin complexed to an enzyme-substrate that can be visually identified.

In another screening method, supernatants of antibody producing hybridomas can be screened by FLOW in a number of different ways as is known by one skilled in the art. One screening procedure involves the binding of potential antibodies to a panel of T cells that express well-known TCRs on their surface. Generally, antibodies that react with intact TCR are detected by this analysis, but the T cells can be fixed slightly with e.g. ethanol, in which case antibodies reacting with denatured TCR polypeptide can be identified. FLOW assays can also be formatted where potential antibodies are screened by their ability to compete with the binding of a known antibody for the TCR present on a T cell.

It is also possible to screen antibodies by their ability to immunoprecipitate a known TCR as analyzed by SDS-polyacrylamide gel electrophoresis or Western blot analysis. An advantage to this assay is that it is possible to identify the chain of the TCR heterodimer that the anti-TCR antibodies are recognizing.

Additionally, screening may be carried out by observing the comodulation of the CD3 antigen. The TCR normally exists on the surface of T cells as a complex with the chains of the CD3 complex. When an antibody binds to this TCR:CD3 complex, the complex in turn becomes internalized in the T cell and disappears from the cell surface. Thus, if T cells are reacted with an antibody specific to the TCR and the complex becomes internalized, a further reaction with an anti-CD3 specific antibody will result in substantially no detection of CD3 bearing cells by FLOW analysis. This comodulation screening procedure detects antibodies that are able to interact with intact TCR on the surface of T cells.

Many additional screening assays, such as those based upon competition with anti-TCR antibodies of known specificity or the ability to cause T cells expressing known TCRs to proliferate in culture, will be known to those skilled in the art and can be used for the selection of appropriate antibodies.

A molecular clone containing a DNA sequence of an antibody to an epitope of a T cell surface molecule can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

Antibody molecules may be purified by known techniques, e.g., immunoabsorption or immunoaffinity chromatography, chromatographic methods such as HPLC (high performance liquid chromatography), or a combination thereof, etc.

Once antibodies of the desired specificity are generated, other antibodies of the same epitope specificity can be selected. Antibodies of such similar epitope specificity can be selected, for example, by observing the ability of such antibody or binding region thereof to inhibit the binding of the antibody of known specificity to its antigen. Various competitive binding assays known in the art can be used.

5.2. Fragments and Derivatives of Monoclonal antibodies Reactive With Defined Regions of the T Cell Anitgen Receptor Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

Various chemical derivatives of the antibodies of the invention can also be produced. For example, immunoconjugates consisting of an antibody molecule or binding region thereof bound to a label such as a radioisotope or other tracer molecule can be made by techniques known in the art. Alternatively, the antibody molecule or fragment thereof can be bound to a therapeutically useful molecule which is targeted to its desired site of action by virtue of the antibody's binding specificity. As one example of such an embodiment, a cytotoxic compound can be conjugated to an antibody of the invention which is specific to a region of the TCR on lymphocytes which are the causative agents of an autoimmune disorder. The cytotoxic compound in conjugate form is thus targeted to the implicated T lymphocytes.

In addition, isotypes of the antibodies of the invention can be switched in order to optimize clinical applications. For example, some isotypes (such as IgG2a) are superior effectors of antibody dependent cell cytotoxicity reactions. Likewise, some isotypes (such as IgG2a) are more readily eliminated from the circulation via the Fc receptors present on cells of the reticuloendothelial system and sequestered in the spleen than others, and, if bound to a target cell (which, for example, may be an effector of autoimmune disease), would be more efficient at removing the target cell from sites of active disease. Accordingly, certain antibody isotypes may be preferable to others, depending on the intended clinical application. Therefore, hybridomas are screened for TCR specific mAbs using a TCR ELISA designed to select for desirable isotypes, such as IgG. In addition, a different isotype may be generated by spontaneous isotype switching and directed toward various uses. A method exists which facilitates selecting for the isotype of interest; the procedure for isotype switching of IgG1 to IgG2a presented as an example, is as follows:

Hybridoma cells are grown in log phase for a 2–3 week period prior to a magnetic bead negative selection. For the magnetic bead selection, super paramagnetic iron oxide particles coated with a goat anti-mouse antibody preparation including all IgG isotype classes (Biomag® beads purchased from Advanced Magnetics, Inc.) may be used. For the process of switching an antibody isotype from IgG1 to IgG2a, it is necessary to block the IgG2a binding sites on the antibody coated beads by incubating with an irrelevant antibody having an IgG2a isotype. $10^8$ hybridoma cells are then incubated with the beads, allowing cells expressing IgG1, IgG2b and IgG3 isotypes to bind to the beads and be removed magnetically from the population. This negative selection should be repeated several times. The remaining cell population, depleted of IgG1, IgG2b and IgG3 bearing cells and enriched for IgG2a bearing cells is plated in 15 microtiter plates at a cell density of about 1000 cells per well. Using commercially available anti-isotypic reagents in an ELISA assay, the wells are screened for IgG2a production. Wells should be screened again by ELISA for IgG2a production and positive clones replated at 0.3 cells per well followed by another round of screening and replating at 0.3 cells per well. Approximately 1–5 out of $10^7$ cells which have switched isotype are optimally selected. Switches such as IgM to IgG can be done similarly using the appropriately coated antibody-coated beads.

Accordingly, the isotype of TCSδ1 also referred to as δTCAR-3, described in U.S. patent application Ser. No. 115,256 filed Oct. 29, 1987, produced by hybridoma δTCAR-3, deposited with the ATCC and assigned accession number HB9578, was switched from $IgG_1$ to $IgG_{2a}$ by the above method.

5.3. Immunoassays

The antibodies of the invention, and fragments thereof containing the binding region (e.g., Fab, Fab', F(ab')$_2$), can be used in various immunoassays. Such immunoassays include but are not limited to competitive and non-competitive assay systems using techniques such as radioimmunoassays, ELISA (enzyme linked immunosorbent assay), "sandwich" immunoassays, precipitin reactions, gel diffusion precipitin reactions, immunodiffusion assays, agglutination assays, complement fixation assays, immunoradiometric assays, fluorescent immunoassays, protein A immunoassays, and immunoelectrophoresis assays, to name but a few.

5.4. Diagnosis and Therapy

The antibodies of the invention, and fragments and derivatives thereof, can be valuable in the diagnosis and therapy of various conditions and disorders affecting the immune system.

5.4.1. Diagnosis

In various embodiments, the antibodies, derivatives and fragments thereof of the invention can be used to detect, quantitate, and/or localize T lymphocytes which express TCRs that comprise and expose the defined region to which the antibody can bind. Both in vitro and in vivo assays can be used, including but not limited to the assays described in Section 5.3, supra. In addition, imaging techniques can be used, in which an antibody of the invention or derivative or fragment thereof is bound to a label. The labeled antibody can then be administered in vivo to determine the localization of its target antigen.

In particular embodiments of the invention, a lymphatic malignancy or immune disorder may be diagnosed by detecting the immunospecific binding of a monoclonal antibody, or derivative or fragment thereof, reactive with an epitope of a defined constant or variable region of a T cell antigen receptor in a patient sample. The patient sample may consist of any body fluid, including but not limited to peripheral blood, plasma, cerebrospinal fluid, lymphatic fluid, peritoneal fluid, or pleural fluid, to name but a few, or any body tissue. Binding may be accomplished and/or detected in vitro or in vivo. In vitro binding may be performed using histologic specimens or subfractions of tissue or fluid, i.e. substantially purified T cells. In vivo binding may be achieved by administering the antibody or fragment or derivative by any means known in the art (including but not limited to intravenous, intraperitoneal, intranasal, and intrasarterial, to name but a few) such that immunospecific binding may be detected; for example, by attaching a radioactive label to the diagnostic antibody, fragment, or derivative.

In specific embodiments of the invention, rheumatoid arthritis or Felty's syndrome may be diagnosed by detecting the binding of a monoclonal antibody, or fragment or derivative thereof, reactive with an epitope of Vδ1 (RA, FS), Vβ3, Vβ9, or Vβ10 (RA) variable region of a T cell antigen receptor in a patient sample, such that increased binding is detected in patients with rheumatoid arthritis or Felty's syndrome compared to normal controls.

In a preferred embodiment of the invention, rheumatoid arthritis or Felty's syndrome may be diagnosed by detecting binding of monoclonal antibody δTCS1, or fragments or derivatives thereof, in that the peripheral blood level of δTCS1 positive T cells in a patient with rheumatoid arthritis or Felty's syndrome is elevated compared to the level in the peripheral blood of a normal person. In a related embodiment, the percentage of total peripheral blood T cells which are δTCS1 positive is observed to be higher in a patient with rheumatoid arthritis or Felty's syndrome compared to the percentage of total peripheral blood T cells which are δTCS1 positive in a normal person. In additional embodiments of the invention, a diagnosis of rheumatoid arthritis or Felty's syndrome may be made based on detecting elevated numbers of δTCS1 positive T cells, relative to total T cells, in other body fluids and tissues including, but not limited to, synovial fluid and synovial membrane. In a further embodiment of the invention, rheumatoid arthritis or Felty's syndrome may be diagnosed in patients in which the peripheral blood ratio of δTCS1 positive to TCRδ1 positive T cells is elevated and, preferably, that it is greater than about 0.4. The binding of antibody or fragments or derivatives thereof may be detected in vitro or in vivo, as discussed supra. Intraarticular administration of a labelled antibody or derivative or fragments thereof may also potentially be utilized as a diagnostic procedure.

It should be understood that the diagnostic methods of the invention are best used in the context of other diagnostic parameters in order to obtain a comprehensive patient diagnosis. For example, a diagnosis of rheumatoid arthritis may be made based on the methods of the invention in the context of other clinical features of rheumatoid arthritis, such as typical joint involvement (chronic, symmetrical arthritis; early involvement most often in the hands); characteristic radiographic features; the presence of rheumatoid factor; the presence of rheumatoid nodules, etc. (Fishman et al., Medicine, Second Edition, J. B. Lippincott Company, Philadelphia, pp. 340–346). As with any diagnostic criteria, the parameters disclosed in the present invention may not be sole determinants, or pathognomonic, of a particular disorder.

Alternatively, according to the invention, a lymphatic malignancy or immune disorder may be diagnosed by detecting the presence of nucleic acid sequences homologous to a gene encoding a defined constant or variable region of a T cell antigen receptor in mRNA from a patient sample. Several procedures could be used to correlate TCR gene expression with disease. These involve 1) producing and analyzing cDNA libraries obtained from the disease related T cells to determine the presence of frequently used or dominant TCR genes. 2) Analyzing disease samples by Southern blot to determine whether specific genetic polymorphisms (restriction fragment length polymorphisms, RFLPs) or oligoclonal TCR rearrangements exist. 3) Analyzing disease samples by the cDNA synthesis, polymerase chain reaction amplification, and slot blot hybridization procedure, see Section 11, infra. The third procedure represents a more efficient procedure in the time required for analysis and in the number of patients that can be analyzed to detect a disease correlation. A fourth procedure using in situ hybridization of T cells without prior T cell culturing may also be extremely useful. Once the disease correlations of interest have been identified, then specific TCR based therapeutics, e.g. anti-TCR monoclonal antibodies, may be produced (see 11.3 infra).

In specific embodiments of the invention, rheumatoid arthritis may be diagnosed in a patient by detecting the presence of nucleic acid sequences homologous to a gene encoding Vδ1, Vβ3, Vβ9, or Vβ10 variable region of a T cell antigen receptor in mRNA from a patient sample, and finding that more frequently expressed Vβ genes include Vβ3, Vβ9, and Vβ10 and/or that a more frequently expressed Vδ gene is Vδ1.

5.4.2. Therapy

In other embodiments of the invention, antibodies, derivatives, or fragments thereof directed against a defined region of the TCR can be therapeutically administered. For example, if the antibody is capable of inducing in vitro T cell proliferation, it may be administered therapeutically to stimulate specific cell-mediated immunity. In another particular embodiment, an antibody directed against a defined region of the TCR can be used to target a cytotoxic molecule to specific TCRs which are the causative agents of an autoimmune disorder.

In another embodiment, an antibody may be administered therapeutically to block the interaction of effector T cells with their specific antigen and thus modulate a deleterious response. A further therapeutic embodiment is to administer an antibody therapeutically to bind to its target and mark those cells for elimination by the RES septem or by antibody dependent cell cytotoxicity (ADCC) reactions, the ablation of the target T cells resulting in a therapeutic effect. According to various embodiments of the invention, monoclonal antibodies directed toward defined regions of T cell antigen receptors may either be used therapeutically at low mitogenic concentrations to specifically activate the TCR bearing subset of interest, or alternatively could be used at much higher concentrations to bind to the receptors of interest, and thereby tag that T cell subset for elimination by the reticuloendothelial system. The important criteria for disease treatment is the ability to modulate specific disease related T cell subsets. The exact nature of this therapeutic modulation, whether to block or suppress a particular T cell subset, or alternatively, whether to stimulate and activate a particular subset, will depend upon the disease of interest and the specific T cell subset(s) involved.

According to various embodiments of the invention, the number of γδ+ T cells with cytotoxic activity may be increased by exposing T cells to an effective concentration of a monoclonal antibody, or derivative or fragment thereof, reactive with an epitope of the variable region of the delta chain of the T cell antigen receptor. Alternatively, higher concentrations of the same antibody may be effective in depleting γδ+ cells. The concentrations of antibody which induce proliferation, or which result in depletion, of γδ+ T cells may be accomplished by methods known in the art, as exemplified in Section 9 below. In specific embodiments of the invention, δTCS1 monoclonal antibody, or fragments or derivatives thereof, used at different concentrations, may result in proliferation, increased cytotoxic activity, or decreased cytotoxic activity, respectively, of T cell populations derived from patients with rheumatoid arthritis.

First generation treatments based on T cell receptor therapeutics may be developed based upon the correlation of specific TCR Variable region subfamilies with disease. These treatments offer an improvement over current procedures, such as anti-CD3 antibody treatment in patients undergoing renal transplant rejection, as the whole T cell population will not be modulated; only the particular T cell subset expressing the TCR V region subfamily of interest will be modulated. In addition, TCR variable region subfamily derived reagents are applicable to the treatment of groups of patients showing similar expression; whereas, a therapeutic combination based on a specific $V_\alpha$ (V-J-C) or a specific $V_\beta$ (V-D-J-C) may only be useful for the treatment of individual patients expressing that exact TCR combination.

Second generation TCR based therapeutics, may include further refinements of the association of particular variable (V), diversity (D) and joining (J) regions with specific disease states for α, β, γ and δ TCR genes. Patients may be further subdivided into groups for treatment based upon the TCR V, D, J and C regions involved; with the goal being to only modulate the actual disease related T cells and not to effect other T cell subsets.

In a particular embodiment of the invention, rheumatoid arthritis may be treated by administering therapeutically effective amounts of a monoclonal antibody, fragment or derivative thereof, which recognizes an epitope of the variable region of the beta chain of a T cell antigen receptor. In particular embodiments, the variable region comprises Vβ3, Vβ9, or Vβ10.

In additional embodiments of the invention, a lymphatic malignancy or immune disorder may be treated by administering therapeutically effective amounts of a monoclonal antibody, or fragment or derivative thereof, which recognizes the constant region of the alpha chain or the variable region of the delta chain of a T cell antigen receptor. In one embodiment of the invention, rheumatoid arthritis or Felty's syndrome may be treated by administering therapeutically effective amounts of a monoclonal antibody, derivative, or fragment thereof, which recognizes an epitope of the Vδ1 variable region of the delta chain of a T cell antigen receptor. In a preferred embodiment, this monoclonal antibody has the binding characteristics of δTCS1. In a specific embodiment of the invention, a patient with rheumatoid arthritis may be treated by administering milligram quantities per day of δTCS1 antibody, or a fragment or derivative thereof, in a suitable pharmaceutical carrier into a patient in need of such treatment (See Section 10, infra).

5.4.3. Therapeutic Compositions; Kits

Various delivery systems are known and can be used for therapeutic delivery of the antibodies of the invention and fragments and derivatives thereof. Methods of introduction include but are not limited to intradermal, intramuscular, intraperitoneal, intravenous, subcutaneous, and intranasal routes. In one embodiment, the antibody can be encapsulated in liposomes.

Various pharmacologic compositions may be utilized in order to deliver the antibodies, or fragments or derivatives thereof, according to the invention. Any suitable pharmaceutical agent with desirable solubility characteristics and chemical properties may be used, including but not limited to, where appropriate, saline or dextrose solutions.

Kits for practice of the instant invention are also provided. For example, such a diagnostic kit comprises in one or more containers a monoclonal antibody or derivative or fragment thereof reactive with an epitope of the constant region of the α TCR. In other embodiments, the antibody or derivative or fragment is reactive with Vβ5.3, or Vβ8.1 of the TCR. The antibody may be labeled. Alternatively, the kit can further comprise a labeled binding partner of the antibody, derivative or fragment. Therapeutic kits can comprise the therapeutic compositions of the invention in one or more containers.

5.5. Monoclonal Antibodies Reactive With the Constant Regions of the T Cell Antigen Receptor Alpha Polypeptide In a specific embodiment, the present invention relates to monoclonal antibodies reactive with the constant region of the alpha chain of the TCR. In a particular example, the invention relates to mAb αF1. In another particular embodiment, the invention relates to mAb αF2.

αF1 and αF2 recognize two different epitopes of the framework region of the constant region of the TCRα monomer. In various embodiments of the invention, αF1 or αF2, or both, or fragments or derivatives of either, or both, can be used to bind to TCRα peptide amino acid sequences, either as part of an intact TCR complex or α peptide, or a fragment thereof.

Monoclonal antibodies αF1 and αF2 are described more fully in the subsections below and in Section 6, infra.

5.5.1. Binding Specificities of αF1 and αF2

Monoclonal antibodies αF1 and αF2 were found to react with αβ TCR⁺ T cell lines, but did not react with αβ TCR⁻ T cell lines (including γδ TCR⁺ cell lines) or B cell lines. Since αF1 and αF2 react with TCR on many T cell lines and a large percentage of PBLs, they are reactive with major framework regions of the TCR molecule.

Both mAb αF1 and αF2 immunoprecipitate the 90 kD αβ TCR heterodimer. mAb αF1 reacts with the oligopeptide representing amino acid residues 141–159 of the α peptide, whereas αF2 reacts with the oligopeptide representing amino acid residues 212–231. Both oligopeptides reside within the constant region of the α chain sequence. Both αF1 and αF2 selectively immunoprecipitated in vitro synthesized peptide.

5.5.2. Immunohistological analysis Using αF1 and αF2

Although both αF1 and αF2 immunoprecipitate TCR of cell lysates of diverse T cell lines, neither bind to viable T cells. Presumably this is because the epitopes recognized by αF1 and αF2, on the constant region of α chain TCR, are hidden on the cell surface.

When the integrity of the cell membrane is disrupted, for example, by histologic fixative, αF1 and αF2 can be used to bind to TCR α peptide. By immunohistological staining, both αF1 and αF2 recognize greater than 90% of both mature peripheral resting and activated T cells, corresponding to the distribution of αβ TCR in the adult T cell population.

5.5.3. Uses Of αF1 and αF2

Because αF1 and αF2 bind to epitopes within the constant region of TCR α peptide, both mAb can be used to define populations of TCR α⁺ cells.

For example, in one embodiment of the invention αF1 and αF2 can be used to study TCRα expression during thymocyte differentiation. It is thought that thymocytes differentiate and mature gradually as they pass from thymic cortex to medulla and finally to peripheral blood (Benjamini and Leskowitz, 1988, *Immunology A Short Course*, Alan R. Liss, Inc., New York p. 141). Numerous studies have suggested that in thymus, during T cell differentiation, δ, β, and γ chain genes are rearranged and transcribed earlier than a chain genes (Chien et al., 1984, Nature 312:31; Raulet et al., 1985, Nature 314:103; Snodgrass et al., 1985, Nature 315:332). αF1 and αF2 can be used to correlate the expression of TCR α protein with thymocyte development.

Furthermore, αF1 and αF2 can be used to determine the state of αTCR protein expression in a cell. For example, unstimulated CEM cells express neither TCR nor CD3 on their surface; however, stimulation with PMA induces CD3 expression (Schackelford et al., 1987, J. Immunol, 138:613). Using αF1, the unstimulated CEM line was found to be negative for the expression of α chain TCR protein in the cytoplasm; however, stimulation with PMA resulted in an increase in intracellular TCRα and surface expression.

αF1 and/or αF2 can also be used to generate or select monoclonal antibodies directed at unique epitopes of the TCRα constant region, i.e. by competitive binding studies. Novel mAb reacting with different epitopes of the TCR α constant region would not compete with αF1 or αF2 for TCR α binding. αF1 and αF2 can also be used to generate antibodies to the αTCR constant region that are able to react with viable cells.

αF1 and αF2 can also be valuable in diagnosis and therapy, as described infra.

In one embodiment of the present invention, αF1 and/or αF2 can be used to detect TCR α protein expression in specimens in vitro, e.g., in cell lysates or in histologically prepared specimens. In one particular embodiment, classification of lymphatic malignancies into B cell, T cell, or non-B non-T cell groups, can be greatly facilitated by demonstrating the presence or absence of TCR α protein using αF1 and/or αF2 according to the present invention.

αF1 and αF2, in various embodiments of the present invention, can be used to establish the cellular derivation of lymphatic malignancies, such as leukemia, lymphoma, and myeloproliferative diseases, and may prove useful in the diagnosis of other malignancies or non-malignant disorders of the immune system.

In another embodiment of the present invention, αF1 and αF2 can be used to monitor therapies involving the proliferation or ablation of α$^+$ T cells.

In a further embodiment of the present invention, αF1 and αF2 could be used to detect TCR-α-producing tissues in vivo. Because αF1 and αF2 do not bind to viable cells, binding would only occur to cells which exhibit enhanced permeability, such as moribund or necrotic cells. These cells would, most likely, be localized to malignant tumors or similar neoplasms associated with lymphoid cell death. In an embodiment of the invention, αF1 and αF2 could be conjugated to a label comprising, for example, a radioisotope. Labeled αF1 and αF2 could then be injected into a patient; localization of radiolabeled antibody can reveal tumor sites.

5.6. Monoclonal Antibodies Reactive With the Variable Region of the T Cell Antigen Beta Polypeptide In another specific embodiment, the present invention relates to monoclonal antibodies reactive with specific variable regions of the beta chain of the TCR. In one particular embodiment of this aspect of the invention, the invention relates to a monoclonal antibody reactive with Vβ5.3. An example of such a Vβ5.3-specific antibody is mAb W112. In another particular embodiment, the invention relates to a monoclonal antibody reactive with Vβ8.1. An example of such a mAb, reactive with human Vβ8.1, is mAb 2D1.

In various embodiments of the invention, W112 or 2D1, or fragments or derivatives of either, can be used to bind with TCRβ peptide amino acid sequences, either as part of an intact TCR complex or β peptide, or T cell surface protein, or a fragment thereof.

Monoclonal antibodies W112 and 2D1 are described more fully in the subsections below and in Section 7, infra.

5.6.1. Binding Sepcificities of W112 and 2D1

W112 immunoprecipitates a heterodimer of 48 kd and 40 kd from HPB, and 2D1 immunoprecipitates the same size dimer from Jurkat cell lysates. Both W112 and 2D1 are anti-minor framework antibodies as they react with a minority of peripheral blood T cells, indicating specificity directed toward the variable portion of TCRβ. Western blot analysis showed that both W112 and 2D1 reacted with the TCRβ protein of their respective cell lines. W112 is a TCR Vβ5.3 specific reagent and 2D1 is a TCR Vβ8.1 specific reagent.

5.6.2. Uses of W112 and 2D1

Because both W112 and 2D1 are anti-minor framework TCRβ specific reagents, these mAb can be used to study, define, quantitate, and localize a subset of T cells.

In one embodiment of the present invention, W112 and 2D1 can be used to study Vβ5.3 and Vβ8.1 expression during thymocyte differentiation. In another embodiment, W112 and 2D1 can be used to generate or select additional anti-minor framework antibodies, i.e., by competitive binding studies.

W112 and 2D1 can also be valuable in diagnosis and therapy, as described infra.

In one embodiment, W112 and/or 2D1 can be used to detect Vβ5.3 and Vβ8.1 subsets of T cells in specimens in vitro, e.g., in cell lysates or in histologically prepared specimens. Such use is of value in the diagnosis of patients with immune system disorders affecting such subsets of their T lymphocytes. In an embodiment of the present invention, W112 and 2D1 can be used to monitor therapeutic procedures that effect these subsets of T cells.

Since both W112 and 2D1 react with viable cells, they can be used therapeutically to modulate Vβ5.3 and Vβ8.1 expressing T cells involved in disease. In one embodiment, W112 or 2D1 could be administered therapeutically to ablate the Vβ5.3 or Vβ8.1 T cell subsets. In another embodiment, W112 or 2D1 could be administered therapeutically to induce the proliferation of the Vβ5.3 or Vβ8.1 T cell subsets. In these embodiments the selective ablation or proliferation of a specific T cell subset by anti-minor framework antibodies will be preferred to modulating the whole T cell population with anti-major framework or pan-T reagents, as only the disease specific T cell subsets will be effected.

In another embodiment of the present invention, W112 or 2D1 could be conjugated to a label comprising, for example, a radioisotope. Labeled W112 or 2D1 could then be injected into a patient; localization of radiolabeled antibody can reveal Vβ5.3 or Vβ8.1 specific disease sites.

6. EXAMPLE: THE GENERATION OF TWO MONOCLONAL Antibodies αF1 AND αF2, DIRECTED AGAINST TWO DIFFERENT EPITOPES OF THE HUMAN αTCR CONSTANT REGION We describe herein two mAb, termed αF1 and αF2, generated against purified αβ heterodimer TCR. Using synthetic oligopeptides, we demonstrated that αF1 recognized amino acid residues 141–159, and αF2 recognized amino acids 212–231, of the constant region of the α chain TCR. Although neither mAb reacted with viable T cells, both antibodies immunoprecipitated TCR αβ heterodimer from HPB, Jurkat, and PBL cells, α chain protein of PMA-stimulated CEM cell line, and a 32 kD in vitro translation product of α chain cDNA. These antibodies have proved to be useful in the immunohistochemical staining of human tissues. These two mAb are valuable tools in the study of TCR and in the clinical classification of T cell lineage neoplasms.

6.1. Material and Methods

6.1.1. Cell Lines

The human cell lines HPB-ALL, Jurkat, Daudi, U923, CEM and Molt-4 were obtained from the American Type Culture Collection (Rockville, Md.), and were maintained in RPMI-1640 medium supplemented with 10% fetal bovine serum. Sequence analyses of the HPB-ALL and HPB-MLT has indicated that both cell lines have the same β and α TCR genes and may have been confused during in vitro culturing (Berkhout et al., 1988, Nucleic Acids Research 16:5209). These cells are referred to as HPB cells to indicate that they are the same line. The cell line Molt-13 was supplied by Dr. Michael Brenner, Harvard Medical School, Boston, Mass. TIL21 and TIL21pBT are human T cell lines isolated from infiltrated lymphocytes of lung tumor (Flatow et al., 1988, FASEB J. 2:3505). Human peripheral blood lymphocytes (PBL) were isolated from normal donors using Ficoll-Hypaque gradient separation (Pharmacia, Piscataway, N.J.).

6.1.2. Monoclonal Antibodies

The murine hybridomas 3A8 and 3D6 were generated by immunizing eight week old female Balb/c mice (Jackson Laboratories, Bar Harbor, Me.) with 1.0 μg of purified αβ TCR protein in complete Freund's adjuvant intraperitoneally. At two-week intervals the mice were given 1.0 μg purified αβ TCR in incomplete Freund's adjuvant intraperitoneally. After three months, sera were tested to be positive as determined by immunoprecipitation of TCR heterodimer using $^{125}$I-labelled HPB and Jurkat cell lysates. Four days before fusion, the mice received the final intravenous injection of 1 lg of purified TCR in PBS. Hybridoma cells were generated sing an established protocol (Wu et al., supra). The mAb produced by clones 3A8 and 3D6 were designated as αF1 and αF2, respectively. The isotypes of mAb αF1 and αF2 were determined to be IgG2a and IgG2b, respectively, using a commercial typing kit (Zymed, San Francisco, Calif.). βF1 (Brenner et al., 1987, J. Immunol. 138:1502), and δTCS-1 (Wu et al., supra.) (T Cell Sciences, Cambridge, Mass.) are mAb that react with the β and δ chains of TCR, respectively. OKT3 was purchased from Ortho Diagnostic System (Raritan, N.J.)

6.1.3. T Cell Lysates and αβ TCR Protein

Human T cell lines bearing the appropriate TCR were solubilized at $5 \times 10^7$ cells/ml in lysis buffer containing 10 mM Tris PH 8.0, 1% Nonidet-P 40 (NP-40), 10 mM iodoacetamide (IAA), 1 mM phenylmethyl sulfonyl fluoride (PMSF), 0.04% aprotinin and 0.3 mM N-tosyl-L-phenylalanine chloromethyl ketone (TPCK). HPB cell lysates were applied to a mixed lectin column of lentil- and ricin-agarose column (Sigma, St. Louis, Mo.). The effluent from the lectin column was further purified through a column of mAb βF1 immobilized Affi-gel 10 (Biorad, Rockville Centre, N.Y.). The bound αβ TCR protein was then eluted with solution containing 25 mM of diethylamine, pH 11.5 and 0.2% NP-40. In general, approximately 80 μg of αβ TCR protein were purified from $5 \times 10^{10}$ HPB-ALL cells.

Figure 6A:
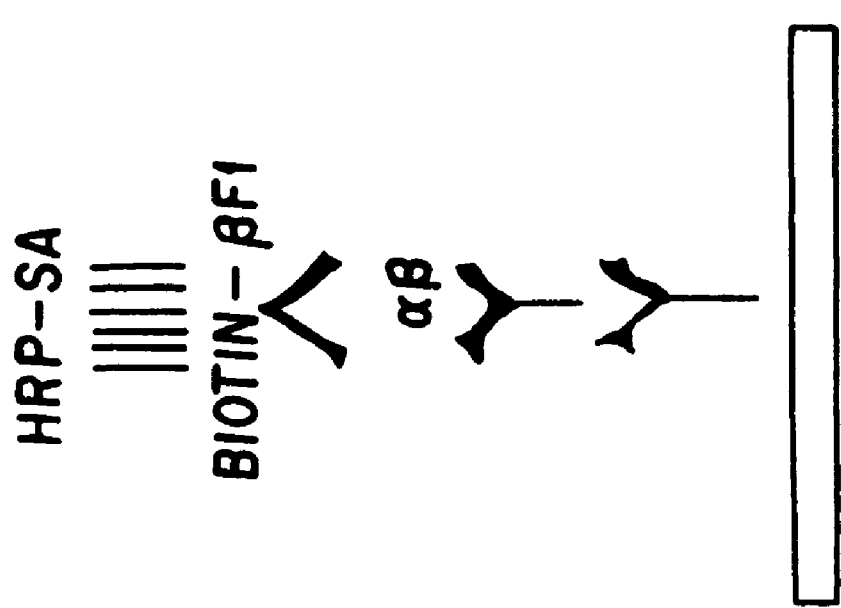

6.1.4. ELISA Method for Screening mAb (FIG. 6A)

96-well microtiter plates (Dynatech, Alexandria, Va.) were coated overnight at 4° C. with 100 μl per well of goat anti-mouse IgG Fc-specific antibodies (Cappel, West Chester, Pa.) at 1 μg/ml in PBS. This was designed to preferentially select for monoclonal antibodies having an IgG isotype. Plates were then blocked with 100 μl per well of 1% BSA in PBS containing 0.05% Tween-20 for 30 minutes. 100 μl of hybridoma supernatants were added to each well and incubated for 1 hour. 100 μl of cell lysate containing 25% FCS and 0.1 μg/ml of biotin-labelled βF1 F(ab)$_2$ fragment were then added to each well and incubated for an additional 2 hours. After washes, 100 μl horseradish peroxidase (HRP) conjugated streptavidin (Zymed, San Francisco, Calif.) was added at 1:2500 dilution to each well. After 30 minutes of incubation, 50 μg of the 0.1% O-phenylenediamine dihydrochloride (OPD) (Sigma, St. Louis, Mo.) substrate solution was added to each well.

The reactions were stopped with 100 μl of 2N $H_2SO_4$. The absorbance of each well was then read on a micotiter plate reader (Dynatech, Cambridge, Mass.) at 490 nm. Between each step, ELISA plates were washed four times with 250 μl per well of PBS containing 0.5% Tween-20 and the incubations were carried out at room temperature.

6.1.5. Assay for TCR Peptide Binding

TCR oligopeptides were custom synthesized by Pennisular Laboratory (Belmont, Calif.) according to the deduced sequences from the α-and β-chain TCR genes (Yanagi et al., 1985, Proc. Nat;. Acad. Sci. U.S.A. 82:3430; Yanagi et al., 1984 Nature 308:145–149). TCR oligopeptides were coupled to protein carrier, BSA (Sigma, St. Louis, Mo.) with succinimidyl-4-(p-maleimidophenyl) butyrate (Pierce, Rockford, Ill.) according to the published procedure (Gitman et al., 1985, Proc. Natl. Acad. Sci. U.S.A. 82:7309). 100 μl of 4.0 μg/ml the peptide conjugates were added per well to microtitre plates and incubated overnight at 4° C. Plates were blocked with PBS containing 1% BSA and 0.05% Tween-20 for 30 minutes. 100 μl of each of the test mAb at about 10 μg/ml were added to each well and incubated for 2 hours. After washing, 100 μl per well of 1:1000 dilution of HRP-conjugated goat anti-mouse IgG antibodies (Zymed, San Francisco, Calif.) were added to each well of the plate and incubated for an additional two hours, followed by the addition of 0.1% of OPD substrate solution. The reactions were stopped with 100 μl of 2N $H_2SO_4$. The absorbance of each well was then read on a microtiter plate reader (Dynatech, Cambridge, Mass.) at 490 nm. Between each step, ELISA plates were washed four times with 250 μl per well of PBS containing 0.5% Tween-20 and the incubations were carried out at room temperature.

10 6.1.6. Immunoprecipitations and SDS-PAGE

Cells were harvested at log growth phase and their surface proteins were labelled with $^{125}$I by the lactoperoxidase method (Brenner et al., 1984, J. Exp. Med. 160:541). Lysates of the iodinated T cells were prepared in a manner similar to that described above.

Immunoprecipitation and one dimensional SDS-PAGE using 10% gels under either non-reducing or reducing conditions were performed as previously described (Wu et al., supra).

6.1.7. Immunohistological Tissue Section Section Analysis

Culture cells were cytocentrifuged on glass slides (Cytospin, Shandon, Pittsburgh, Pa.) and fixed with 100% methanol. The immunoperoxidase staining of cytospun cell smears was carried out using commercial staining kits (CRL, Cambridge, Mass.). Immunoperoxidase staining was also carried out on frozen cryostat sections of thymus and tonsil.

6.1.8. In Vitro Translaiton

Phage Sp6 RNA polymerase and rabbit reticulocyte in vitro translation system were purchased from New England Biolabs (Beverly, Mass.) and Bethesda Research Laboratories (Gaithersburg, Md.), respectively. pGA5-pSP73 plasmid construct was a gift of Dr. Michael Brenner, Harvard Medical School, Boston, U.S.A. pGA5-pSP73 is a plasmid construct composed of a pSP73 plasmid backbone (Promega, Wis., U.S.A.) and a coding region for the α chain TCR gene derived from the pGA5 cDNA clone (Sim et al., 1986, Nature 312:771). pGA5-pSP73 plasmid construct was linearized with restriction enzyme XhoI, and was subsequently used as the DNA template for the transcription of the pGA5 α chain gene using the phage Sp6 promoter (Krieg et al., 1984, Nucl. Acids Res. 12:7057; Hope and Struhl, 1985, Cell 43:177). The resulting capped pGA5 RNA transcript was then translated into $^{35}$S-labeled α chain protein in the rabbit reticulocyte in vitro translation system according to the manufacturer's protocol. Rabbit globin mRNA was also included in the in vitro translation system as an added irrelevant protein for the immunoprecipitation assays.

6.2. Results

6.2.1. Isolaiton of Major Framework mAb.

Figure 1B:
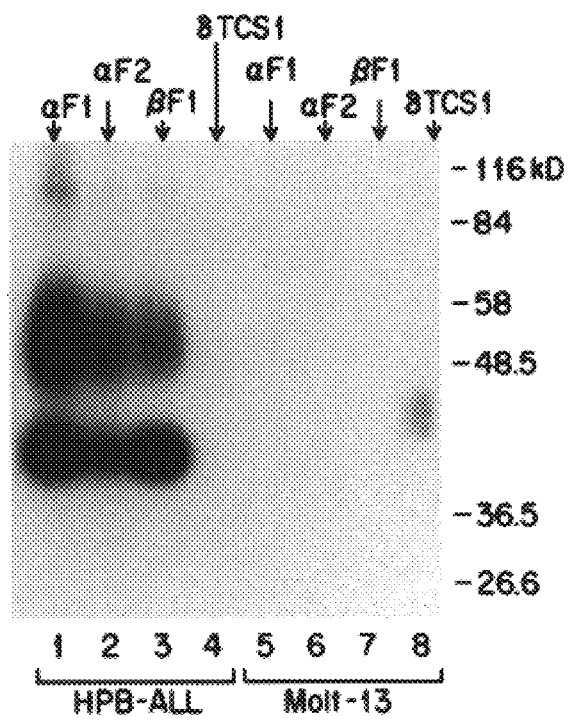

Both mAb αF1 and αF2 tested positive in the ELISA using cell lysates of αβTCR$^+$ HPB and Jurkat cell lines, but tested negative with cell lysates of MOLT-4 and Daudi. MOLT-4 is a T cell line that lacks α chain TCR and Daudi is a B cell line that is αβ TCR negative. The mAbs were further analyzed by immunoprecipitation using $^{125}$I-labeled HPB and MOLT 13 cell lysates. Both mAb immunoprecipitated a 90 kD protein of TCR α and β heterodimer from HPB cells under non-reducing conditions (FIG. 1a, lanes 1 and 2). The same αβ TCR protein is immunoprecipitated by βF1, a mAb directed against β framework of TCR (FIG. 1A, lane 3) (Brenner et al., 1987, J. Immunol. 138:1502). Under reducing conditions, both αF1 and αF2 mAb immunoprecipitated two proteins of 40 and 49 kD from HPB cells, as does βF1 (FIG. 1B, lanes 1, 2 and 3). In contrast, no proteins were immunoprecipitated by either αF1, αF2, or βF1 when membrane lysates from Molt-13, a γδ T Cell line, was used (FIG. 1A and 1B, lanes 5, 6, 7).

As a control, the Vδ specific antibody, δTCR-1, immunoprecipitated the γδTCR from the γδ$^+$ cell line MOLT-13, but not from the αβ cell line HPB (FIGS. 1A and 1B, lanes 4 and 8).

Similar results were also obtained with cell lysates isolated from $^{125}$I-labeled αβ$^+$ Jurkat cells and PBLs (FIG. 2).

6.2.2. Reactivity of mAb αF1 and αF2

Immunocytochemical staining using αF1 and αF2 mAb was performed on a variety of cell lines. As shown in Table 1, both αF1 and αF2 mAb reacted positively with αβ T cell lines HPB, Jurkat, TIL21 and TIL21PBT, but negatively with γδ T Cell line Molt-13 and non-T cell lines Daudi and U923. Also αF1 and αF2 detected the presence of α chain TCR protein in the PMA stimulated CEM line, but not in the unstimulated cells.

TABLE 1

CROSS REACTIVITY OF mAb WITH DIFFERENT HUMAN CELL LINES

| Cell Name | Cell Type | Reactivity with mAb | | | | |
|---|---|---|---|---|---|---|
| | | OKT3 | BF1 | αF1 | αF2 | δTCS1 |
| HPB | T Cell | ++ | +++ | +++ | +++ | − |
| Jurkat | T Cell | ++ | +++ | +++ | +++ | − |
| TIL21 | T Cell | ++ | ++ | ++ | ++ | − |
| TIL21pBT | T Cell | ++ | ++ | ++ | ++ | − |
| CEM | T Cell | + | ++ | − | − | − |
| CEM + PMA** | | ++ | ++ | ++ | + | − |
| Molt-13 | T Cell | ++ | − | − | − | + |
| Daudi | B Cell | — | — | — | — | — |
| U923 | Monocyte | — | — | — | — | — |

*Cell growing at log phase were washed and cytospinned onto glass slides. Immunohistological staining with different mAb was performed as described. Reactivity was determined arbitrarily on a scale of − to +++.
**CEM cells were incubated with PMA at 1 ng/ml for three days before being harvested and stained with mAb.

Both αF1 and βF1 were used to stain cryostat sections of human thymus and tonsil. As shown in FIG. 3, βF1 stained about 70% of T cells in the cortical zone (3A) and over 90% in the medullary zone (3C) of the thymus. αF1, however, stained about 30% T cells in cortex (3B) and 90% in medulla (3D). When tested on tonsil tissue section, both mAb reacted with T cells in the interfollicular areas (E and F). αF2 staining was similar but weaker than that of αF1. Neither mAb stained viable T cells at a detectable level.

6.2.3. Specificity of αF1 and αF2 mAb

To further define the specificity of αF1 and αF2, both mAb were tested for their ability to recognize synthetic oligopeptides derived from α-chain TCR sequence in an ELISA. The reactivities of αF1 and αF2 against α and β chain derived synthetic oligopeptides are shown in Table 2.

TABLE 2

REACTIVITY OF αF1 and αF2 WITH SYNTHESIZED α AND β PEPTIDES

| Peptide* | BOUND (OD$_{490}$) MONOCLONAL ANTIBODY | | | |
|---|---|---|---|---|
| | αF1 | αF2 | βF1 | δTCS1 |
| α21–42 | 0.04 | 0.08 | 0.04 | 0.04 |
| α141–159 | 0.26 | 0.05 | 0.08 | 0.04 |
| α163–182 | 0.04 | 0.05 | 0.05 | 0.05 |
| α212–231 | 0.03 | 0.86 | 0.06 | 0.05 |
| β42–56 | 0.04 | 0.07 | 0.04 | 0.04 |
| β144–161 | 0.05 | 0.05 | 0.04 | 0.06 |
| β192–210 | 0.08 | 0.04 | 0.07 | 0.03 |
| β231–244 | 0.06 | 0.04 | 0.06 | 0.04 |

*α and β peptides from both the variable and constant region were coupled to protein carrier and coated on the microtitre plates. Reactivity with mAb was observed by developing a signal with a second goat anti-mouse-HRP conjugate. The number after α and β indicate their spanning location residue within their corresponding α and β TCR chains.

mAb αF1 reacted with the oligopeptide derived from TCR α chain spanning from amino acid 141 to 159 (α141–159) whereas mAb αF2 reacted with a different oligopeptide derived from TCRα amino acid 212 to 231 (α212–231). Both oligopeptides reside within the constant region of the α chain sequence. Six other oligopeptides derived from other regions of α and β chains of human TCR did not react with either αF1 or αF2. Neither of the control antibodies, βF1 and δTCS-1, reacted with the synthetic α or β chain oligopeptides.

Figure 4A:
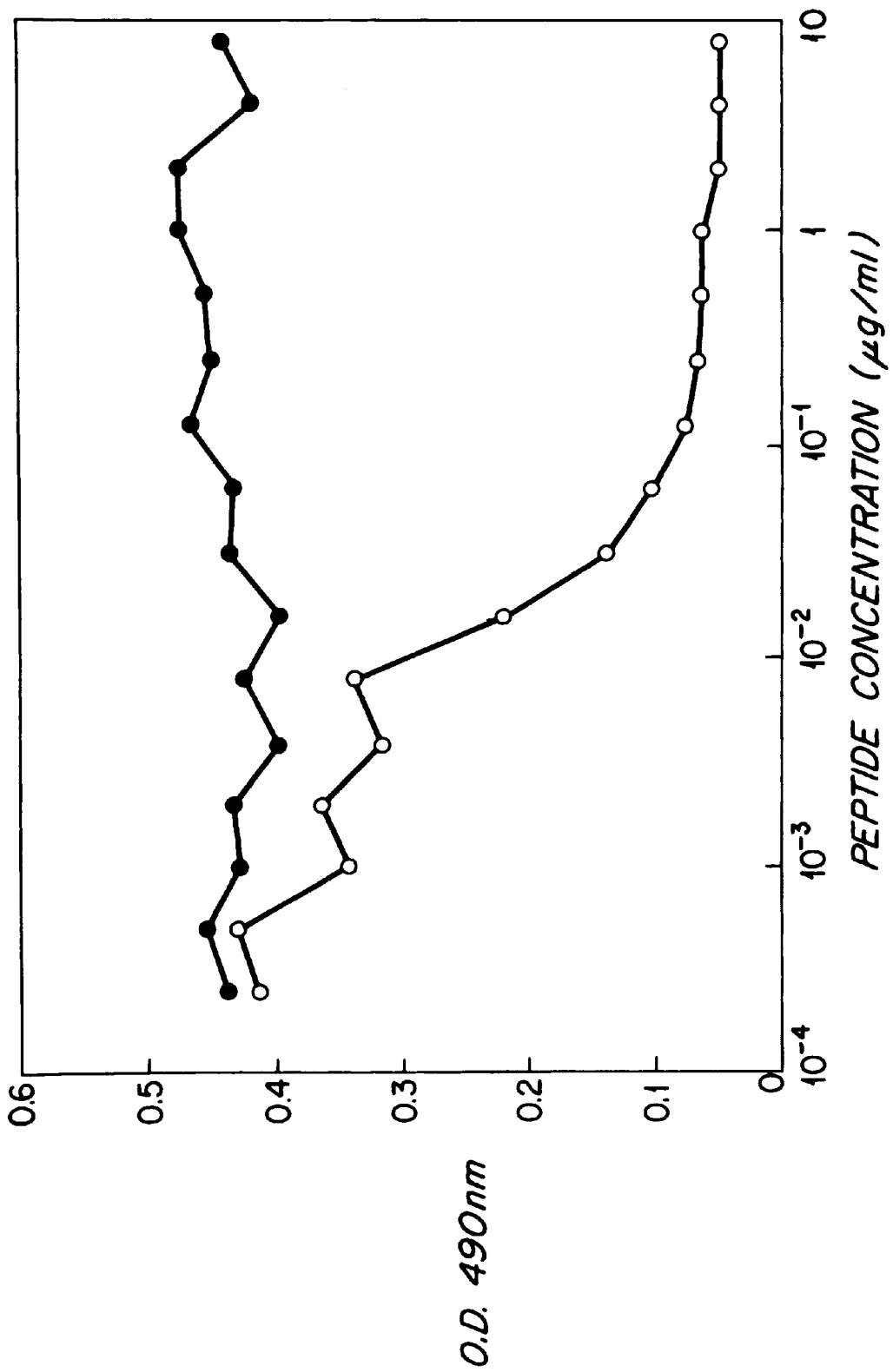
Figure 4B:
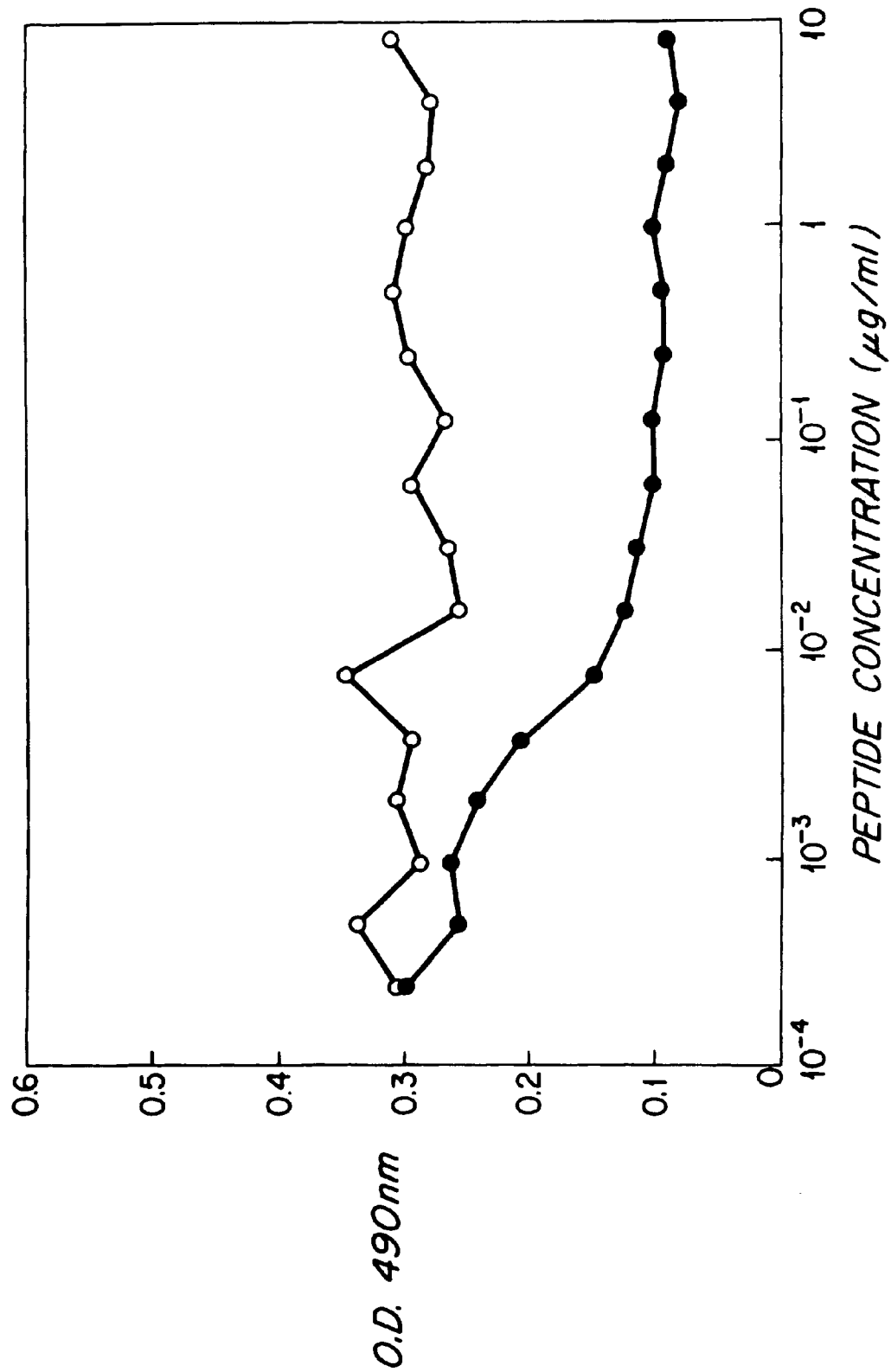

In addition, in a competitive TCR-ELISA immunoassay, oligopeptide α141–159 blocked the binding of mAb αF1 to TCR isolated from HPB, with a $K_d$ of $2\times10^{-9}$ M (FIG. 4a). Similarly, synthetic oligopeptide α212–231 was able to compete with the TCR of HPB for the binding to αF2 ($K_d$ $5\times10^{-9}$ M) (FIG. 4b). None of the other oligopeptides tested was able to compete with HPB TCR in the TCR-ELISA assay.

6.2.4. Immunoprecipitation of In Vitro Synthesized α CHAIN TCR BY αF1 AND αF2

To further confirm the specific reaction of αF1 and αF2 with α chain TCR protein, both mAb were used in an immunoprecipitation assay using an in vitro translated protein mixture containing a known α chain TCR protein and an irrelevant protein, rabbit globin (FIG. 5, Lane 6). In this assay, αF1 and αF2 specifically immunoprecipitated an α chain TCR protein of 32 kD but not the irrelevant rabbit globin (12 kD)(FIG. 5, Lane 1 and 2). In contrast, there were no proteins immunoprecipitated when two isotype matched, irrelevant mAb were used (FIG. 5, Lane 3 and 4).

6.3. Discussion

We have generated two mAb, αF1 and αF2, directed against two distinct epitopes on the constant region of the α chain of TCR protein. Both mAb were shown to immunoprecipitate an αβ heterodimer of human TCR from αβ T cell lines, such as HPB and Jurkat, as well as peripheral blood lymphocytes. By immunohistological staining, both antibodies recognized greater than 90% of both the mature peripheral resting and activated T cells and lymphocytes in thymus and tonsil. Both mAb also immunoprecipitated the in vitro translated product of an α cDNA clone. Using synthetic oligopeptides prepared according to the published sequences of α chain constant region, we have identified the specific epitopes recognized by both mAb αF1 and αF2.

Both αF1 and αF2 do not stain viable T cells. It is surprising that even αF1, which recognized an epitope in the constant region that was very close to the variable region is not able to recognize the surface TCR proteins on viable T cells. Thus, it appears that the epitopes recognized by αF1 and αF2 on the constant region of α chain TCR are hidden on the cell surface. It should also be noted that αF1 stains all the available T cells expressing the α chain TCR protein. This observation indicates that the epitope recognized by αF1 is conserved among all the αβ T cells.

TCR is present on the cell surface as a complex associated with at least three other proteins, the CD3 complex (Davis and Bjorkman, 1988, supra). Both the constant region of the αβ TCR and the CD3 complex are highly non-polymorphic. This conservation of sequence suggests that the constant region of TCR may serve as an important functional domain to interact with the CD3 complex for the transduction of signals during T cell activation. Upon binding of antigen, the variable region of TCR may undergo conformational changes and subsequently alter the interaction between the constant region of TCR and the CD3 complex. The latter alteration may thus initiate the functional role of the CD3 complex in signal transduction during T cell activation. αF1 and αF2 will be useful in further analyzing this process.

Both αF1 and αF2 are useful for studying TCR biosynthesis during T cell differentiation. αF1 identifies T cells in tissue section, as does βF1. Numerous studies have suggested that in the thymus, during T cell differentiation, TCR δ, γ and β chain genes are rearranged and transcribed earlier than α chain genes (Chien et al., 1984, Nature 312:31; Raulet et al., Nature 314:103; Snodgrass et al., 1985, Nature 315:232). It is also suggested that in thymus T cells differentiate and mature gradually along their path from cortex to medulla and finally to peripheral blood. The differential staining patterns of αF1 versus βF1 in the cortical area of the thymus may indicate the presence of such a process of T cell maturation.

αF1 and αF2 can also be used to study TCRα protein expression. It has been reported that in the absence of α chain TCR, the CEM cell line does not express TCR and CD3 complexes on its cell surface (Uppenkamp et al., 1988, J. Immunol. 140:2801). However, upon stimulation with PMA, the CEM line does express surface CD3 complexes (Shackelford et al., 1987, J. Immunol. 138:613). Using αF1, we found that the unstimulated CEM line is negative for the expression of α chain TCR protein. However, in the presence of PMA, the intracellular level of α chain TCR protein increases and the TCR:CD3 complex appears on the cell surface. This observation demonstrates that PMA induces the expression of α chain protein, resulting in surface CD3 expression.

αF1 and αF2 can also be useful in the clinical classification or diagnosis of lymphoid malignant or non-malignant disease. In mouse, it has been demonstrated that the expression of β protein precedes that of α protein. It is, therefore, possible to identify undifferentiated leukemic cells where the various stages of differentiation can be subclassified. Thus, αF1 and αF2 are useful reagents in analyzing the pathway of TCR expression in man and may also be valuable reagents for the clinical classification of T lymphocytes in disease states.

Similarly, abnormal expression of TCRα in malignant cells can be detected by αF1 and αF2. The T-cell lymphoma cell line SUP-T1 (Denny et al., 1986, Nature 320:549) expresses a hybrid mRNA transcript comprised of an immunoglobulin heavy-chain variable region and a portion of TCRα, including J segment sequences. αF1 and αF2 were used to show that this hybrid mRNA is, in fact, translated into a protein which includes a portion of the TCRα constant region.

7. EXAMPLE: MONOCLONAL Antibodies TO THE VARIABLE REGIONS OF HUMAN T CELL ANTIGEN RECEPTOR

7.1. Results

7.1.1. Generation of W112 and 2D1 Monoclonal Antibodies

To make mAb specific to Vβ5.3 and Vβ8.1, two human T cell leukemic lines, HPB and Jurkat, were used as immunogens. HPB expresses Vβ5.3 on its cell surface (Leiden and Strominger, 1986, Proc. Natl. Acad. Sci. U.S.A. 83:4456–4460; Leiden et al., 1986, Mol. Cell Biol. 6:3207–3214; Toyonaga and Mak, 1987, Ann. Rev. Immunol. 5:585–620), and Jurkat cells express Vβ8.1 (Yanagi et al., 1984, Nature 308:145–149; Leiden and Strominger, 1986, supra; Toyonaga and Mak, 1987, supra). BALB/c mice were immunized with $1\times10^7$ HPB-MLT or Jurkat cells. Four weeks later, the same amount of cells were injected intravenously into the primed mice and the splenocytes were fused after four days with mouse myeloma P3X63Ag8.653 cells. Ten days later, hybridomas were screened for anti-TCR activity with an ELISA protocol as illustrated in FIG. 6(a), using HPB and Jurkat cell lysates. Positive wells were cloned by limiting dilution and clones rescreened. Data from a sample ELISA rescreening is shown in Table 3. Out of 500 hybridoma supernatants screened, only 2D1 was positive in the ELISA assay. Anti-TCR major-framework mAb, W76, was used as a positive control as it binds to the constant region of every β chain. Anti-CD3 mAb, OKT3, was used as the negative control.

TABLE 3

| Screening: | 2D1 | W76 | OKT3 |
|---|---|---|---|
| 1 | 0.132 | 0.165 | 0.055 |
| 2 | 0.278 | 0.315 | 0.115 |

W76 is an anti-TCR major framework reagent used as a positive control.
OKT3 is an anti-CD3 reagent used as a negative control.

Figure 6B:
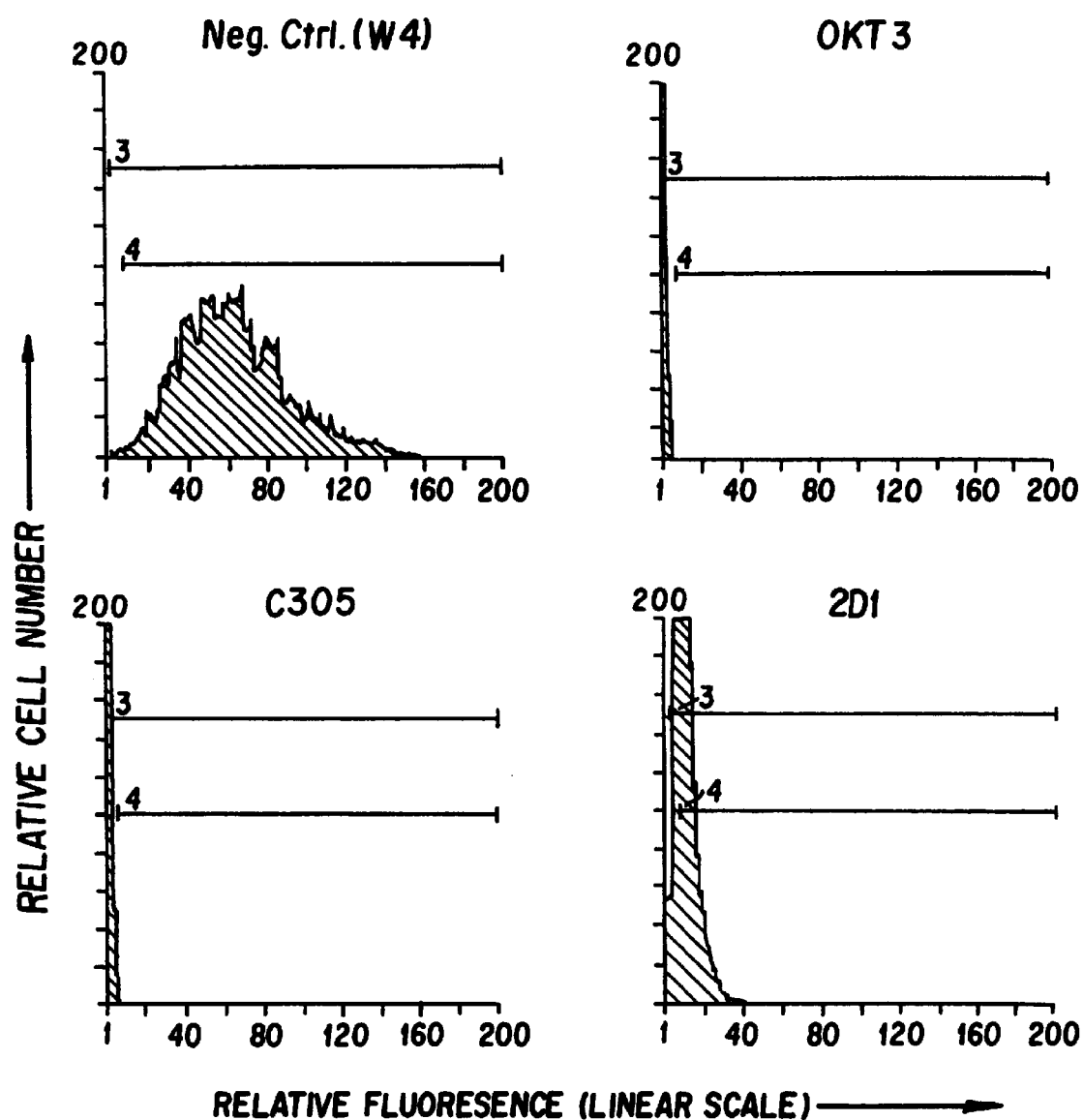

To further confirm the TCR-ELISA screening results, CD3-comodulation assays were run as shown in FIG. 6(b). For the comodulation assays, Jurkat or HPB cells were incubated overnight with hybridoma supernatants. Cells were then washed and reincubated with FITC-conjugated OKT3, and analyzed by flow cytometry. Positive hybridoma supernatants such as 2D1 that were able to modulate the TCR-CD3 complex off of the cell surface, stained negatively with OKT3 the following day. Negative hybridoma supernatants stained positively with OKT3 the following day. From the screening, mAb W112 reactive with HPB and 2D1 reactive with Jurkat were identified.

7.1.2. Specificity of W112 and 2D1

Figure 7A:
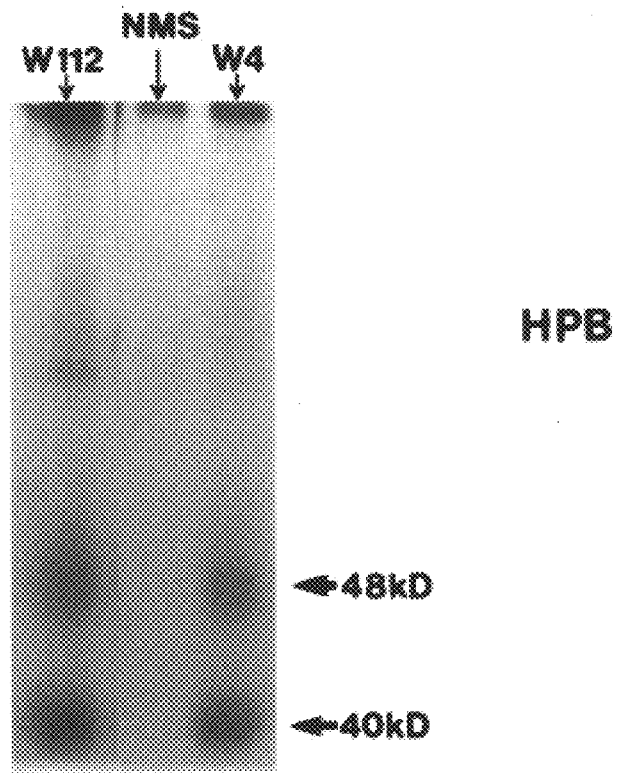
Figure 7B:
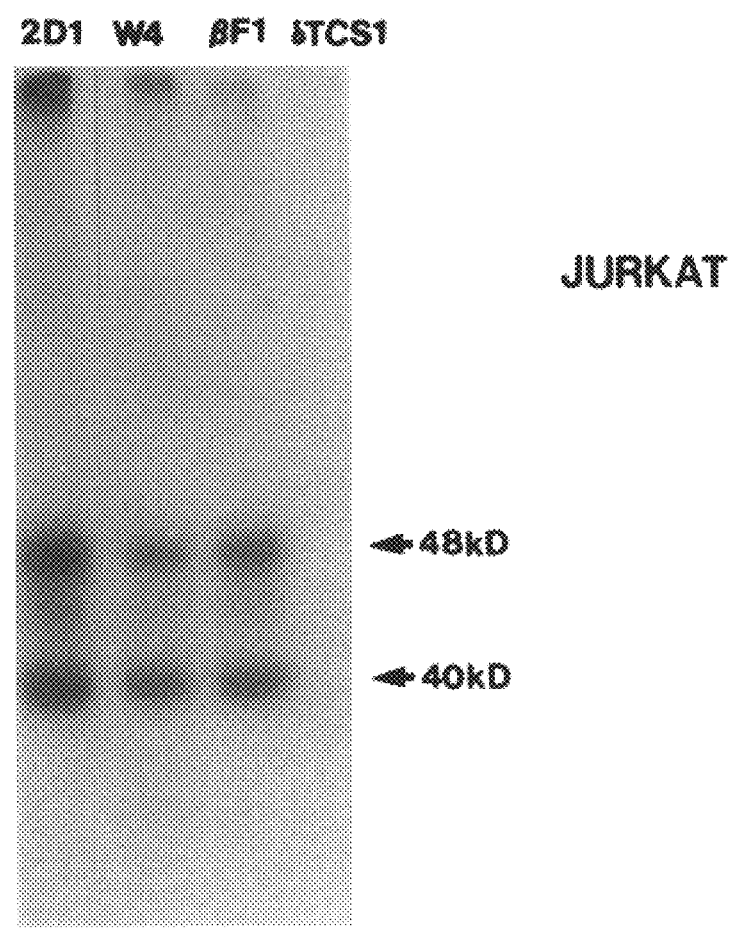

The reactivity of W112 and 2D1 with TCR on HPB and Jurkat cells was tested using immunoprecipitation. $^{125}$I surface labelled HPB and Jurkat cell lysates were incubated with mAb and the precipitated immune complexes were then run on 10% SDS-PAGE (FIG. 7). W112 specifically immunoprecipitated a heterodimer of 48 kD and 40 kD from HPB lysates (FIG. 7A). 2D1 immunoprecipitated the same sized heterodimer from Jurkat cell lysates (FIG. 7B). The molecular weights of the immunoprecipitated proteins are similar to those precipitated by βF1, a mAb reactive with a framework epitope of the β chain constant region, or by αF1, the anti-major framework anti-TCRα antibody (Section 6, supra).

The reactivity of W112 was also tested by Western blot analysis (FIG. 8). HPB cell lysates were fractionated by 10% SDS-PAGE and then transferred to nitrocellulose sheets. The sheets were first incubated with W112, washed and then incubated with horse radish peroxidase (HRP) conjugated goat anti-mouse antibody. After washing, color was developed with an HRP substrate. W112 specifically reacted with a 40 kD protein. This 40 kD protein also reacted with the β constant region reagent βF1 (FIG. 8) indicating W112 was TCRβ chain specific.

To determine the chain specificity of 2D1, Jurkat cells were metabolically labelled with $^{35}$S-methionine and the cell lysates were incubated with 2D1. Immunoprecipitated complexes were then fractionated by 10% SDS-PAGE and the dried gel autoradiographed. Antibodies 2D1 and βF1 reacted with the 40 kD β chain of Jurkat cells (FIG. 9).

7.1.3. Fluorescent Activated Cell Sorting Using W112 and 2D1

Reactivity of W112 and 2D1 was determined by FACS analysis. PBLs from normal donors were reacted with W112, 2D1, OKT3 or normal mouse serum, washed, incubated with FITC-labelled goat anti-mouse antibody and analyzed on an Ortho® flow cytometer (FIG. 10). When tested against normal PBLs, W112 and 2D1 antibodies detected only minor populations of cells. Among 10 samples tested, W112 reacted with from 0.3% to 5% peripheral blood cells, and 2D1 reacted with 0.5% to 13%. The positive control antibody, OKT3, represented a pan-T cell reagent, and stained 70% of the peripheral blood lymphocytes. The negative control reagent, normal mouse serum, was non-reactive. Since W112 and 2D1 react with subsets of T cells, they are anti-minor framework antibodies.

7.2. Discussion

Together these results indicate that both W112 and 2D1 antibodies detect a small subset of T cells in the large population of cells present in peripheral blood. W112 and 2D1 are TCR anti-minor framework specific reagents that react with only that subpopulation of cells in peripheral blood that expresses that particular minor framework determinant protein. Both antibodies are specific to the β chain of the TCR heterodimer and furthermore are specific to that variable region present on the cells used as their immunogen.

2D1 is a TCR Vβ8.1 specific reagent. W112 was determined to be a TCR Vβ5.3 specific reagent by the following criteria. It has been reported that the T cell leukemia line HPB-MLT rearranges two TCR β genes which are expressed at the mRNA level (Leiden, et al., 1986, Molec. Cell. Biol. 6:3207). Cloning and sequencing of cDNA clones corresponding to the two rearranged genes revealed that one of the rearrangements is defective and is characterized by a out-of-frame V-D-J joining event which causes several stop codons in downstream C-region sequences. A second cDNA represents the functional β gene from HPB since it is composed of a full-length open reading frame and its deduced amino acid sequence corresponds to the amino-terminal protein sequence of the β chain isolated from HPB-ALL cells (Jones, et al., 1985, Science 227:311. The deduced amino acid sequence for the defective gene is identical to the V region sequence which identifies the Vβ6.1 family (Concannon, et al., 1986, Proc. Natl. Acad. Sci. 83:6598; Kimura et al., 1986, J. Exp. Med. 164:739). The amino acid sequence for the functional gene is identical to the V region sequence which identifies the Vβ5.3 family. Thus, TCR Vβ-specific antibodies which bind to HPB cells must recognize the Vβ5.3 family. Thus, W112 is a TCR Vβ5.3 specific reagent.

W112 and 2D1 were generated against specific T cell clones having defined TCR proteins and selected for the preferred IgG isotype using the TCR ELISA. Different IgG subtypes for these antibodies could be selected by the isotype switching protocol described in Section 5.2, supra. These reagents have clinically relevant uses in disease diagnosis and therapy. Since these antibodies react with anti-minor framework determinants present on specific T cell subsets, they would be preferred clinical reagents for detecting or modulating Vβ5.3 and Vβ8.1 disease specific T cells as compared to anti-major framework reagents or pan-T reagents that by their nature must affect large populations of T cells.

The data presented supra for generating TCR antibodies of defined specificity using whole T cell clones as immunogens and selecting for TCR reagents of defined isotype, can readily be extended to producing additional anti-minor framework monoclonal antibodies. Antibodies to Vβ12.1, Vβ1.2, Vβ12.4, Vβ2, Vβ9, and Vβ10 are being generated by immunizing with the T cell clones or cell lines listed in Table 4. αβ+ T cell clones can likewise be used to produce anti-minor framework or viable region specific anti-γ and anti-δ reagents.

TABLE 4

| Cell line | Vβ | Vα | Dβ | Jβ |
|---|---|---|---|---|
| C11 | 2.? | | | |
| M11 | 2.2 | | 2.1 | 2.3 |
| DT259 | 3.2 | | 1.1 | 2.1 |
| 2G2 | 4.1 | | 2.1 | 2.5 |
| DT110 | 4.2 | | 1.1 | 1.1 |
| HPB | 6.1 | 12.1 | 2.1 | 2.5 |
| 3A1, 5A5 | 6.1 | | | |
| ATL122 | 6.3 | 1.1 | | 1.5 |
| L17 | 6.9 | 17.1 | 1.1 | 1.5 |
| Jurkat | 8.1 | 1.2 | 1.1 | 1.2 |
| CEM2 | 9.1 | | | 2.3 |
| ATL121 | 10.2 | | 1.1 | 1.5 |
| CEM1 | 12.4 | | | |
| ATL21 | 15.1 | | 1.1 | 1.5 |
| HUT102 | 20.1 | | | 1.2 |
| DT55 | | 4.3 | | |
| SUPT1 | | 7.2 | | |
| HUT 78 | 18.1 | 1. | | |
| MOLT 16 | 1. | 2. | | |

8. EXAMPLE: ELEVATION OF A γδ T-CELL SUBSET IN PERIPHERAL BLOOD AND SYNOVIAL FLUID OF PATIENTS WITH RHEUMATOID ARTHRITIS

The levels of δTCS1 positive and TCRδ1 positive T cells were determined in the peripheral blood and synovial fluid of patients with rheumatoid arthritis (RA) and Felty's syndrome (FS). Elevated levels of a γδ T cell subset identified by δTCS1 was found in the peripheral blood and synovial fluid of patients with RA as well as in the peripheral blood of patients with FS.

8.1. Materials and Methods

8.1.1. Patient Selection

Twenty-nine patients with definite or classical RA and 11 additional patients with Felty's Syndrome seen in the Rheumatic Disease Unit of the Wellesley Hospital were studied. Controls consisted of 22 healthy volunteers (NML) from the Wellesley Hospital and T Cell Sciences, Inc. Twelve of the controls were age-matched. Since the data obtained from the age-matched control subjects from the two groups were comparable to those not matched for age, all control data was pooled. In addition, 5 patients with seronegative spondyloarthropathies (3 with psoriasis, 1 with Reiter's syndrome and 1 with ankylosing spondylitis) were examined. All patients were receiving nonsteroidal anti-inflammatory drugs (NSAIDs). In addition to NSAIDs, some of the RA patients had received at various times during active disease stages any of the following: remittive agents, prednisone, or cytotoxic agents/remittive agents.

8.1.2. Clinical Evaluation

A number of clinical variables were examined in each patient, including: 1) disease duration, 2) number of actively inflamed joints (defined as those with tenderness or effusions), 3) erythrocyte sedimentation rate (ESR; Westergren) and 4) medications.

8.1.3. Ppreparation of Monocuclear Cells From Peripheral Blood

Equal volumes of whole blood (containing anti-coagulant) and Sepracell-MN (Sepratech Corp.) were added to a centrifuge tube. After gentle mixing, the tube was centrifuged at 1500×g at room temperature for 20 minutes. After density separation, mononuclear cells found in the opalescent compact band just below the meniscus were collected. They were washed twice by mixing the cells with four volumes of PBS-BSA (0.1% w/v), and subjecting the mixture to centrifugation at 300×g for 10 minutes per wash.

8.1.4. Immunofluorescence Staining of Cell Surface Markers

All patient cells were phenotyped by flow cytometry using the Ortho Diagnostics Cytofluorograph II (Ortho Diagnostic Systems, Inc., Raritan, N.J.). Fluorescein-conjugated monoclonal antibodies specific for various cell surface determinants were used for a direct immunofluorescence staining procedure. Briefly, $2-5 \times 10^5$ mononuclear cells were suspended in 100 μl of PBS with 0.2% bovine serum albumin and 0.05% sodium azide (flow buffer) at 4° C. Conjugated monoclonal antibodies (100 ng) were added to the cell suspension mixed well and incubated for 30 minutes at 4° C. The stained cells were washed with flow buffer two times and finally resuspended in the same buffer for cytometric analysis. The monoclonal antibodies utilized for immunofluorescence included the following from Ortho Diagnostics Systems, Inc. (Raritan, N.J.), OKT3, OKT4, and OKT8, which recognize the CD3, CD4 and CD8 determinants, respectively, and TCRδ61 and δTCS1, which recognize all human γδ T cells and a subset of them, respectively.

8.2. Results

We first examined the levels of TCRδ1$^+$ T cells and δTCS1$^+$ cells in the peripheral blood of patients with rheumatoid arthritis (RA) and compared them to the levels in peripheral blood of patients with Felty's synodrome (FS) and healthy control subjects (NML). The results (FIG. 11, left panel) revealed comparable log mean levels of peripheral blood TCRδ1$^+$ T cells in RA (5.2%) and NML (3.9%) patients (p>0.05), whereas FS patients exhibited higher levels (6.8%) relative to the other groups; however, the difference was not statistically significant (p>0.05). In contrast, mean levels of PB δTCS1$^+$ T cells in RA (1.8%) and FS (4.5%) were significantly elevated relative to NML (0.8%) (p=0.007 and p=0.006, respectively) (FIG. 11, right panel). The level of δTCS1$^+$ T cells in RA was not statistically different from that in FS (p>0.05).

The level of peripheral blood δTCS1$^+$ T cells was next examined as a proportion of TCRδ1$^+$ cells. The results (FIG. 12) revealed an elevation in the mean ratio of δTCS1/TCRδ1 in both RA (0.4) and FS (0.6) relative to NML (0.2) (p=0.02 and p=0.005, respectively). Moreover, in patients with FS who demonstrated elevated levels of TCRδ1$^+$ T cells, δTCS1$^+$T cells accounted for the majority of TCRδ1$^+$ T cells while in normals, δTCS1 T cells account for <20% of the TCRδ1$^+$T cell population. These results suggested a correlation between the level of δTCS1$^+$ T cells and TCR61$^+$ T cells. Indeed, the level of δTCS1$^+$ T cells correlated strongly with the level of TCRδ1$^+$ T cells in FS (r=0.98, p=0.001) (FIG. 13).

Since elevated levels of peripheral blood δTCS1$^+$ T cells were observed in RA, we next asked whether the increased peripheral blood levels could be a reflection of a local increase in δTCS1$^+$ T cells within the synovium. To address this issue, we evaluated the levels of δTCS1$^+$ T cells and TCR61$^+$ T cells in paired synovial fluid and peripheral blood samples from 16 RA patients and compared these levels to synovial fluid samples from 9 patients with seronegative spondyloarthropathies (SSA), five of whom also had peripheral blood levels determined. The results (FIG. 14, lower panel) revealed comparable log mean levels of $\delta TCS1^+$ cells in paired RA peripheral blood and synovial fluid samples (1.9% and 2.2%, respectively). Moreover, the level of $\delta TCS1^+$ T cells in RA peripheral blood was elevated relative to the peripheral blood level in SSA patients (0.05%) (p=0.05), and there appeared to be a difference between the synovial fluid levels in RA and SSA (p=0.1). The level in RA peripheral blood and RA synovial fluid, but not in SSA synovial fluid, was greater than that in the peripheral blood NML group. The levels of $TCR\delta1^+$ T cells in paired RA peripheral blood and synovial fluid samples were comparable (5.2% vs 5.2%) and not significantly different from that in peripheral blood of NML controls (3.6%) (p>0.05 for both comparisons (FIG. 14, upper panel). Again, there was a trend toward a lower synovial fluid level in SSA (3.0%) relative to RA peripheral blood and synovial fluid levels.

When we examined $\delta TCS1/TCR\delta1$ ratios in paired peripheral blood and synovial fluid samples, we observed comparable ratios in RA peripheral blood (0.40), RA synovial fluid (0.5) and SSA synovial fluid (0.6), (p>0.05 for all comparisons) (FIG. 15). However, the $\delta TCS1/TCR\delta1$ ratios in RA synovial fluid were significantly elevated relative to that in NML peripheral blood (0.2±0.5) (p=0.005). Of note, the $\delta TCS1/TCR\delta1$ ratio in SSA synovial fluid was also elevated relative to NML peripheral blood (p=0.04). The ratio in SSA peripheral blood was comparable to those in NML peripheral blood and RA peripheral blood (p>0.05 for both).

8.3. Discussion

The results of the present study demonstrate elevated levels of a $\gamma\delta$ T cell subset in the peripheral blood and synovial fluid of RA patients and in peripheral blood of patients with FS. In contrast to the preliminary data of Brennan, F. M., et al. (1988, J. Autoimmunity, 1, 319–326) we did not observe an elevation in total $\gamma\delta$T cells in the synovial fluid of RA patients. Brennan et al., however, examined paired peripheral blood and synovial fluid samples from only 3 patients.

The pathogenic significance of an elevation in a $\gamma\delta$ T cell subset in RA remains unclear. However, an increase in a T cell population in RA synovial fluid with cytotoxic potential is consistent with the observation of spontaneous cytotoxicity of synovial T cells directed against both self and non-self epitopes in RA (Example 9, infra). These findings may not reflect non-specific recruitment of T cells into the inflammatory process; an elevation of a specific subset of $\gamma\delta$ T cells was observed, not an elevation in the whole $\gamma\delta$ population. Moreover, the elevation of $\delta TCS1^+$ T cells in RA synovial fluid and not SSA synovial fluid suggests that the increase in $\delta TCS1^+$ T cells in RA is not a result of non-specific effects of inflammation.

To date, a total patient population of 20 normals, 16 RAs, and 10 Felty's patients has been evaluated for the presence of an elevated $\delta TCS1^+$ subset in peripheral blood. An elevated level, defined as the mean value observed for the patients plus 2 standard deviations, was observed in 1/20 normals (5%), 4/16 RAs (25%) and 5/10 Felty's (50%). The proportion of patients with elevated $\delta TCS1^+$ cells in the FS group and RA population was statistically greater than that in the group of healthy subjects with $X^2$=8.9 (p=0.003) and 2.9 (p=0.08), respectively. It is expected that as the general patient population is further divided into subgroups based upon HLA expression and disease state, that these levels of correlation between $\delta TCS1^+$ cells and disease will increase.

9. EXAMPLE: NOVEL AUTOREACTIVE CYTOTOXIC ACTIVITY AGAINST SYNOVIOCYTES BY RHEUMATOID ARTHRITIS DERIVED T CELL LINES AND CLONES

T cell lines were established from synovial tissue and peripheral blood of RA and non-RA patients. Phenotypic and functional studies indicated that specific T cell recruitment occurs in rheumatoid arthritis joints.

9.1. Materials and Methods

9.1.1. Patient Samples

A total of 23 paired RA patient synovial tissue and peripheral blood samples were collected for this study. All the patients had seropositive classic RA with ages ranging from 38 to 77 years with a mean age of 59.5. In addition to the RA patient samples, we also obtained tissue samples from 8 non-RA patients. Seven of these patients had traumatic arthritis of the knee (i.e., torn meniscus) and their synovial tissue was derived by arthroscopy. One of the eight (NST-7) non-RA tissue specimens was from the knee of a patient with ankylosing spondilitis. In the non-RA patient group, a peripheral blood sample was obtained only from the ankylosing spondylitis patient.

9.1.2. Sample Processing and Cell Lines

A panel of various cell lines were derived from each patient, whenever possible. T cell lines were obtained from both the disease site and the peripheral blood.

9.1.3. Synovial Tissue-Derived T Cell Lines

Synovial tissue-derived T cell lines from RA patients (ST-line) were initially established by placing finely minced synovium in a 24 well plate (Costar, Cambridge, Mass.) containing IL-2 medium which consisted of RPMI 1640 supplemented with 10% fetal calf serum (Hyclone, Logan, Utah), 100 Units/ml penicillin, 100 ug/ml streptomycin, 1 mM sodium pyruvate, 50 ng/ml gentamycin, 10 mM Hepes and 20 Units/ml of recombinant interleukin-2 (I1–2) (Amgen, Thousand Oaks, Calif.). After the culture conditions had been optimized, the minced synovium was instead placed into fetal calf serum free medium consisting of AIM-V (Gibco, Grand Island, N.Y.), 5% human AB serum (Center for Diagnostic Products, Milford, Mass.), 5% LymphocultT (Biotest, Fairfield, N.J.) and 20 u/ml recombinant IL-2. The activated T cells within the diseased synovium migrated out of the tissue in the presence of IL-2 medium. The ST-line T cells were maintained by replacing half of the culture volume with fresh IL-2 medium twice a week. After 3 weeks in culture, the T cells required additional stimulation. Initial cultures were stimulated with allogeneic, irradiated feeder cells from normal peripheral blood lymphocytes (PBL) at a concentration of $2\times10^5$/well and 100 ng/ml of a CD3-specific monoclonal antibody, OKT3. ST-line T cells were cloned by limiting dilution in round bottom 96 well plates (Costar, Cambridge, Mass.) with $1\times10^5$ feeder cells per well. After optimization, later cultures were stimulated by growing the T cells on CD3 coated 24 well plates (coated with 2.5 $\mu$g/ml OKT3) for a minimum of 3 hours, followed by washing 3 times and then plating the cells. It was observed that the use of allogeneic and even autologous feeder cells biased the cell growth toward CD8+ cells during culture. The lines maintained their original phenotype better on CD3 coated plates.

9.1.4. Peripheral Blood-Derived T Cell Lines

Peripheral blood-derived T cell lines (PB-T) were obtained by culturing PBL in IL-2 medium plus 1 ug/ml PHA (Welcome Research Laboratories, Beckenham, England).

9.1.5. B Cell Lines

B cell lines were derived from PBL by Epstein-Barr virus (EBV) transformation (Alpert, S. D., et al., 1987, J. Immunol., 138, 104).

9.1.6. Peripheral Blood Macrophages

Peripheral blood macrophages (PBMO) were obtained by overnight adherance of PBL in RPMI medium plus 10% human AB serum (Center for Diagnostic Products, Milford, Mass.). The non-adherant cells were thoroughly washed away and the adherant macrophages isolated by incubation with ice cold calcium/magnesium free phosphate buffered saline (PBS).

9.1.7. Synoviocytes

Synoviocytes were also obtained by culturing in IL-2 medium in either 100 mm dishes in which the tissue was minced or in 6 well dishes (Costar, Cambridge, Mass.). The medium was usually supplemented with human serum unless otherwise stated. Type B synoviocytes were fibroblast cells which were negative for nonspecific esterase (Sigma, St. Louis, Mo.) and HLA-DR while Type A synoviocytes were nonspecific esterase and HLA-DR positive (Carson, D. A. and Fox, R. I., 1985, In "Arthritis and Allied Conditions", McCarty, D. J. (Ed.), p. 257; Iguchi, T., et al., 1986, Arth. Rheum., 29, 600). Separation of Type A and Type B cells was accomplished by differential adherance and trypsin sensitivity. Synovial fibroblast cultures could be obtained by 3–5 minute trypsinization from a tissue monolayer outgrowth or by allowing the fibroblasts to overgrow the primary mixed culture. The mixed cultures that had 3–5 minute trypsin treatment resulted in greater than 95% pure Type A, macrophage-like cultures, as measured by esterase staining. Not all patient samples generated Type A cells in adequate numbers for functional assays. Both types of synoviocytes, PB macrophages and the EBV-B cell lines were used as autologous targets in cytotoxicity assays.

9.1.8. Cell Surface Phenotyping

All patient cell lines were phenotyped by flow cytometry using the Ortho Diagnostics Cytofluorograf II. Fluorescein-conjugated monoclonal antibodies specific for various cell surface determinants were used for a direct immunofluorescence staining procedure. Briefly, $2-5 \times 10^5$ cells were suspended in 100 µl of PBS with 0.2% bovine serum albumin and 0.1% sodium azide (flow buffer) at 4° C. Conjugated monoclonal antibodies (100 ng) were added to the cell suspension mixed well and incubated for 30 minutes at 4° C. The stained cells were washed with flow buffer two times and finally resuspended in the same buffer for cytometric analysis. The monoclonal antibodies utilized for T cell phenotyping include the following from Ortho, Raritan, N.J.; OKT3, OKT4, OKT8, which recognize the CD3, CD4 and CD8 determinants, respectively. In addition to the T4/T8 subsets, we also stained for the helper-inducer and helper-suppressor subsets using phycoerythrin-conjugated monoclonals 4B4 and 2H4 (Coulter, Hialeah, Fla.). Finally, T cells were also stained with a $V_\delta 1$ TCAR specific monoclonal antibody, δTCS-1. Fluorescein-conjugated HLA DR Class II-specific antibody was purchased from Becton Dickinson, Mountain View, Calif.

9.1.9. Cytotoxicity Assay

T cell mediated cytotoxicity was measured by a 3-hour $^{51}$Cr release assay as previously described (Snider, M. E., et al., 1986, Transplantation, 42, 171). Briefly, target cells were labeled with 50–100 µC $^{51}$Cr for 30 minutes at 37° C. in a shaking water bath. After washing the target cells three times in Hanks buffered saline containing 10% serum, they were resuspended in assay medium which consisted of RPMI plus 10% fetal calf serum and 10 mM Hepes. Assay plates were prepared by the addition of 200 µl volume of effector T cells adjusted to $6.25 \times 10^4$ per well (resulting in an Effector:Target ratio of 25:1) or by the addition of 200 µl of medium or water alone. Radioactive target cells were placed in prepared V-bottom 96 well plates (Costar, Cambridge, Mass.) at $2.5 \times 10^3$ cells in a 20 µl volume. The plates were spun at 50×g for 5 minutes and incubated at 37° C. in a humidified, 5% $CO_2$ incubator for 3 hours. The assay was harvested by removing 100 µl of supernatant from each quadruplicate well and radioactivity release was measured on an LKB gamma counter. Percent specific lysis was calculated using the following formula:

$$\% \text{ Specific Lysis} = ER - SR/X - B \times 100$$

where ER=mean $^{51}$Cr release in the presence of effector T cells, SR=mean spontaneous $^{51}$Cr release in media alone, X=mean maximum $^{51}$Cr release in water and B=machine background. Means were calculated from quadruplicate wells and standard deviations never exceeded 10%.

9.1.10. In Situ Immunohistochemistry

Synovial tissue in about 2 cm square pieces was snap frozen in liquid nitrogen, coated with OCT media, and stored at −70° C. Frozen sections were cut at 5 µm on a cryostat, placed on microscope slides, air dried, and fixed in acetone for 5 minutes at room temperature. Sections were rehydrated in PBS and stained with δTCS1 at 10 µg/ml final concentration for 30 minutes at room temperature. Reactivity with δTCS1 antibody was determined using a commercial immunoperoxidase kit specific for mouse Ig (Ortho, Raritan, N.J.). Cells were counterstained using hematoxylin and examined by light microscopy.

9.1.11. Suppressor Factor Assay

Normal peripheral blood lymphocytes were stimulated with either OKT3 or PHA. Suppressor activity was determined by the ability of a γδ+ cell culture supernatant to inhibit the proliferative response of PBLs to OKT3 or PHA. Culture supernatants were generated from RA synovial tissue derived T cell cultures or from the paired RA PBL derived T cell cultures following stimulation on either OKT3 or δTCS1 coated plates. Plates were coated first with 2.5 µg/ml goat anti-mouse IgG1 (Southern Biotech Assoc., Birmingham, Ala.) followed by the appropriate monoclonal antibody at 2.5 ng/ml for 3 hours at 37° C. Control cultures received either no stimulation or stimulation with irradiated allogeneic peripheral blood lymphocytes plus 100 ng/ml OKT3. Monoclonal antibody coated plates were selected to eliminate the production of lymphokines by the allogeneic feeders. Normal PBLs were plated in 96 well flat bottom plates at $8\times10^4$ cells/well in RPMI 1640 plus 10% FCS with either 10 ng/ml OKT3 or 0.5 ng/ml PHA (Wellcome Diagnostics, Dartford, England). Culture supernatants were added at a starting dilution of 1:4 with serial dilutions up to 1:1024. Assays were pulsed on day 3 with 1.0 μCi/well of tritium for 8 hours before harvesting.

9.2. Results

9.2.1. Cell Surface Phenotype of Synovial Tissue-Derived and Peripheral Blood-Derived T Cells

9.2.1.1. δTCS1 Cell Surface Phenotype

The gamma delta T cell antigen receptor specific monoclonal antibody, δTCS1 (Wu, Y-J., et al., 1988, J. Immunol., 141, 1476–1479), was used to quantitate the gamma delta T cell receptor positive T cells infiltrating synovial tissue. Table 5 compares the percentage of δTCS1 positive T cells from RA patient synovium (ST-line) with the peripheral blood T cells of each of the 23 paired RA samples and 8 paired non-RA samples.

TABLE 5

PERCENTAGE OF δTCS1 POSITIVE T CELLS DERIVED FROM ARTHRITIS PATIENT T CELL LINES*

| Patient Sample | Synovial Tissue | Peripheral Blood |
|---|---|---|
| ST-2 | 12 | 5 |
| ST-9 | 7 | 1 |
| ST-17 | 0 | 7 |
| ST-18 | 2 | 1 |
| ST-24 | 2 | 1 |
| ST-25 | 64 | 11 |
| ST-27 | 10 | 5 |
| ST-28 | 18 | 8 |
| ST-29 | 2 | 13 |
| ST-30 | 0 | 0 |
| ST-31 | 2 | 1 |
| ST-32 | 34 | 0 |
| ST-33 | 13 | 0 |
| ST-34 | 1 | 1 |
| ST-35 | 80 | 3 |
| ST-36 | 1 | 2 |
| ST-37 | 7 | 1 |
| ST-38 | 5 | 0 |
| ST-39 | 9 | 3 |
| ST-43 | 8 | 0 |
| ST-48 | 5 | 3 |
| ST-49 | 1 | 5 |
| ST-51 | 3 | 1 |
| x ± SD | 12.4 ± 20 | 3 ± 4 |
| NST-1 | 2 | NA+ |
| NST-2 | 3 | NA |
| NST-5 | 8 | NA |
| NST-7 | 2 | + |
| NST-9 | 2 | NA |
| NST-10 | 9 | NA |
| NST-17 | 5 | NA |
| NST-13 | 1 | NA |
| x ± SD | 4 ± 3 | NA |

* = double immunofluorescence with OKT3 and δTCS1 monoclonal antibodies. Numbers are expressed as percentage δTCS1 positive cells relative to percentage CD3 positive cells, in order to standardize for samples having varying amounts of CD3+ cells.
+NA = not available (no peripheral blood received)

In normal subjects, gamma-delta T cells comprise 1–5% of peripheral blood T cells (Wu, Y-J., et al., supra; Brenner, M., et al., 1986, Nature, 322, 145). Our results show that while the values of percentage of δTCS1 positive T cells derived from peripheral blood derived T cell lines from RA patients were within the normal range, the values for several paired RA synovial tissue lines were above the normal range (Table 5). Indeed, a marked increase in the proportion of gamma-delta T cells was observed in RA synovial tissue lines. The lower half of Table 5 demonstrates that in most cases the proportion of gamma delta cells from non-RA synovial-derived T cells (NST-lines) are not significantly elevated. These paired patients' T cell lines were cultured in parallel, with the mean length in culture of 18.8±8 days, ranging from 11 to 36 days.

Three of the synovial tissue lines were stained by double immunofluorescence with fluorescein-cinjugated OKT8 and phycoerythrin-conjugated δTCS1. We found a significant percentage of gamma delta+ cells were also CD8+, since the percent of double staining cells for ST-25, ST-32 and ST-33 were 47%, 23%, and 5%, respectively. In addition, the majority of the gamma delta+ cells in ST-35 were CD4+ since the T cell line was 94% CD4+ and 80% δTCS1+. These findings suggest that at least in some synovial tissue, the gamma delta+ cells are not members of the CD4$^-$CD8$^-$ cell population.

9.2.1.2. CD4, CD8, 4B4, 2H4 Cell Sruface Phenotypes

Synovial tissue lines and paired peripheral blood T cell lines from seven RA patients different from those listed in Table 5 were analyzed for T cell subset information (i.e. CD4/CD8 ratio and suppressor-inducer/helper-inducer cell ratio). These paired RA patient T cell lines were cultured in parallel with the mean length in culture of 13±1.8 days, ranging from 9 to 15 days. The RA patients' lines were also compared with synovial tissue-derived T cells from four non-RA patients (NST-line). The NST-lines were in culture for a mean of 14±3 days, ranging from 10–19 days. Table 6 confirms previous reports (Forre, O., et al., 1982, Scand. J. Immunol., 16, 815) that T cells derived from diseased joints and stimulated with PHA are predominantly CD4+ (mean value of 79% ±15) and 4B4+ (mean value of 91.4%±6) while the T cells from the peripheral blood of the same patients had an equal mixture of CD4 and CD8 populations (mean values for CD4 and CD8 were 43.8%±17 and 48.8%±12, respectively).

TABLE 6

Comparison of Cell Surface Phenotype of Rheumatoid and Non-Rheumatoid T Cell Lines.*

| | Phenotype Marker | | | | |
|---|---|---|---|---|---|
| Sample | CD4 | CD8 | 4B4 | 2H4 | 4B4/2H4 |
| ST-LINE | 79 ± 15 | 13.9 ± 8.6 | 91.4 ± 6 | 3.1 ± 1.8 | 29.5 |
| ST-PBT | 43.8 ± 17 | 48.8 ± 12.4 | 69.9 ± 14.6 | 22.2 ± 17 | 3.1 |
| NST-LINE | 89 ± 6.5 | 6.7 ± 2.4 | 92.4 ± 8.4 | 1.4 ± 0.7 | 66 |

* = % positive ± standard deviation

However, this is the first reported evidence that the phenotype of cultured T cells from synovial tissue of RA and non-RA patients are similar since the NST-line CD4 mean value was 89% ±6 and the mean 4B4 value was 92.4%±8. Again, the PBT cells from the RA patients had a more normal distribution of helper-inducer and suppressor-inducer cells, as compared to the infiltrated T cells (i.e. the mean values for ST and PBT were 69.9%±15 4B4 and 22.2%±17 2H4). However, the ratio of 4B4/2H4 in the RA patients was distinct from normal subjects regardless of the source of T cells studied (Morimoto, C., et al., 1985, J. Immunol., 134, 1508).

9.2.2. In Situ Immunohistochemistry

Samples of synovial tissue were analyzed by in situ staining with δTCS1 to determine whether γδ+ cells were in fact present in inflamed RA joints and that their detection was not due to the selective expansion of a minor T cell subset during the cell culture procedure. As can be seen in Table 7, δTCS1+ cells were present in the majority of infiltrated synovial membrane tissue.

TABLE 7

In situ Staining by T cell Specific Monoclonal Antibodies in Untreated Synovial Tissue

| Sample | DR | Infiltrate | CD3 | CD4 | TCRδ1 | δTCS1 |
|---|---|---|---|---|---|---|
| ST-46 | − | + | + | + | − | − |
| ST-47 | − | ++ | ++ | | + | + |
| ST-48 | − | ++ | ++ | | + | +/− |
| ST-49 | − | − | − | | − | − |
| ST-50 | − | − | − | | − | − |
| ST-51 | − | ++ | ++ | ++ | + | + |
| ST-52 | − | ++ | ++ | | + | + |
| NB-02 | 4 | +++ | +++ | | − | − |
| NB-04 | 4 | +++ | +++ | | + | + |
| NB-05 | 4 | +++ | +++ | | +/− | +/− |
| TW-01 | − | +++ | +++ | | + | + |

Thus, δTCS1 cells have been detected in the peripheral blood, synovial fluid and synovial membrane of patients with RA and in the peripheral blood of Felty's patients.

9.2.3. Functional Acitivity of Synovial Tissue Derived T Cells

9.2.3.1. Cytotoxicity Activity

Cytotoxicity of T cell lines from RA synovial tissue against their autologous Type A synoviocytes (macrophage-like cells), Type B synoviocytes (fibroblasts) and peripheral blood macrophages was measured in a 3 hour $^{51}$Cr release assay (Table 8]

TABLE 8

Cytotoxicity of RA Synovial Derived T Cell Lines*

| Effector Cell ST-Line: | Type A Synoviocytes | Type B Synoviocytes | Peripheral Blood Macrophages |
|---|---|---|---|
| ST-1 | 80 | 9 | ND |
| ST-9 | 50 | 5 | 5 |
| ST-11 | 41 | 8 | ND |
| ST-13 | 50 | 2 | 6 |
| ST-14 | 42 | 4 | 24 |
| ST-15 | 11 | 7 | ND |
| ST-16 | 1 | 5 | ND |
| ST-17 | 61 | 0 | ND |
| ST-22 | 27 | 2 | ND |
| ST-25 | 26 | 6 | 13 |
| ST-28 | 0 | 7 | 4 |

* = % specific lysis in 3 hour $^{51}$Cr release assay.

ST-lines derived from nine out of eleven patients demonstrated cytotoxicity against autologous Type A synovial target cells while not affecting the viability of the Type B synovial cells or PB macophages. In addition, autologous B cells were not lysed by the ST-lines. The natural killer (NK)-like activity of the T cell lines was variable and did not correspond with the lytic activity against autologous synovial macrophage-like cells. In fact, cloning of T cells from a patient (ST-1) whose line exhibited high NK-like activity resulted in Type A-specific clones with no detectable NK-like activity (Table 9).

TABLE 9

Cytotoxic Activity of Synovial Tissue Derived T Cell Line and Clones*

| Effector Cell | Target Cells | | |
|---|---|---|---|
| ST-Line or Clone: | Type A Synoviocytes | Type B Synoviocytes | K562 |
| Line | 81 | 9 | 63 |
| Clone 1 | 58 | 0 | 8 |
| Clone 2 | 60 | 0 | 1 |
| Clone 3 | 32 | 0 | 2 |
| Clone 4 | 24 | 0 | 0 |

* = % specific lysis in 3 hour $^{51}$Cr release assay.

Table 9 also shows that both CD4+ and CD8+ clones could specifically lyse Type A synoviocytes since clones 1, 3 and 4 were CD4+ while clone 2 was CD8+.

The specificity of ST-lines for their syngeneic tissue-derived targets was not shared by the peripheral blood T cell lines from the same patients. In fact, the peripheral blood derived T cells followed two patterns of cell lysis: either they were very lytic against the entire target cell panel including K562, or they had very weak activity against K562 and occasionally other target cells as well. An example of the latter is shown in Table 10.

TABLE 10

Comparison of the Cytotoxic Activity of a Synovial-Derived T Cell Line and a peripheral Blood T Cell from a single Patient.

| | % Specific Lysis By:* | |
|---|---|---|
| TARGET CELLS | ST-Line | ST-PBT |
| Type A Synoviocytes | 50 | 3 |
| Type B Synoviocytes | 2 | 4 |
| PB-Macrophage | 6 | 21 |
| EBV-B Cell | 0 | 0 |
| K562 | 11 | 18 |
| Daudi | 2 | 1 |

*The effector-to-target cell ratio was 25:1 and this experiment was done with the RA patient, ST-13.

In this case, one patient's (ST-13) ST-line and PB-T cytotoxicity was measured against a panel of autologous target cells, K562, and the lymphokine-activated killer (LAK)-sensitive target cell, Daudi. The ST-line lysed the Type A cells and had some detectable natural killer cell-like activity while not lysing any other target cells in the panel. However, the PB-T cells from the same patient which were cultured in parallel did not lyse either of the autologous synoviocytes but did have some NK-like activity and lysed some of the PB macrophages. To examine the specificity of ST-13 line activity more closely, a cold target inhibition assay was performed (FIG. 16). Lysis of $^{51}$Cr labeled Type A cells by ST-line T cells was directly inhibited by the addition of increasing numbers of unlabeled Type A cells. However, addition of increasing numbers of unlabeled K562 did not inhibit $^{51}$Cr release of the Type A cells, suggesting that the lysis of Type A cells is not due to NK-like activity.

The Type A cell specificity of RA synovial tissue-derived T cells was not shared by synovial-derived T cells from the one out of nine non-RA patients(NST-3) where cultures yielded enough Type A synoviocytes for $^{51}$Cr labeling. Table 11 shows the cytotoxic activity of 2 NST-lines and 2 ST-lines against a panel of target cells including autologous synoviocyte targets, allogeneic synoviocyte targets and allogeneic B cells.

TABLE 11

Comparison of the Alloreactivity and Target Specificity by Non-Rheumatoid and Rheumatoid Arthritis-Derived T Cell Lines

| Target Cells | % Specific Lysis by: | | | |
|---|---|---|---|---|
| | NST-3 | NST-7 | ST-17 | ST-22 |
| Autologous Type A cells | 17 | NA | 61 | 27 |
| Autologous Type B cells | 42 | NA | 0 | 2 |
| Allogeneic Type A cells | 0 | 3 | 7 | 34 |
| Allogeneic Type B cells | 7 | 2 | 39 | 4 |
| Allogeneic EBV-B cells | 2 | 0 | 33 | 40 |

The allogeneic synoviocyte and B cell targets were derived form Rheumatoid Arthritis patients.
NA = target cells not available NST-3 line T cells lysed Type B cells to a greater extent than the Type A cells and neither NST-lines had any significant alloreactivity. In contrast, the synovial tissue derived lines both appeared to lyse the Type A cells while not affecting the Type B cells. In addition, the T cells from these two patients demonstrated alloreactivity against Epstein Barr Virus B cells and cytolytic activity against allogeneic Type A cells for ST-22 or allogeneic Type B cells for ST-17. This alloreactivity was only seen in these 2 patients from the panel of 11 patients tested to date.

9.2.3.2. Cytotoxic Activity of a γδ Positive T Cell Line; Effect of δTCS1 Monoclonal Antibody T cell line ST-25, derived from the synovial tissue of a rheumatoid arthritis patient, was assayed for cytotoxic activity against its autologous target cells. The effector cells were pretreated with δTCS1 (2 μg/ml) and then washed. The anti-HLA-DR (Becton Dickinson, Mountain View, Calif.) and the anti-KLH (Keyhole limpet hemocyanin) control antibodies were added at the initiation of the assay (2 μg/ml) and were present during the 3 hour assay. At the time of the assay, the phenotype of ST-25 was 41.8% double positive for δTCS1 and CD3 and 39.3% double positive for δTCS1 and CD8. The results of the ST-25 killing assay are given in Table 12.

TABLE 12

Cytotoxicity Data for T Cell Line ST-25*

| Target Cells | ST-25 alone | ST-25 anti-HLA-DR antibody | ST-25 plus δTCS1 antibody | ST-25 plus anti-KLH antibody |
|---|---|---|---|---|
| ST-25 Type A Synoviocytes | 17 | 7 | 52 | 15 |
| ST-25 Type B Synoviocytes | 9 | ND | ND | ND |
| ST-25 B Cell Line | 0 | ND | ND | ND |
| ST-25 PBMO | 24 | 14 | 124 | 43 |
| PB Line 13 | 0 | 0 | 4 | ND |
| PB Line | 0 | 1 | 21 | 0 |
| K562 | 29 | ND | ND | ND |

* = % specific lysis at an effector target ratio of 25:1
ND = not determined

The ST-25 cell line effectively killed ST-25 autologous Type A synoviocytes and peripheral blood macrophages and K562 cells. Preincubation of ST-25 cell line with an anti-HLA-DR antibody (Becton Dickinson, Mountain View, Conn.) caused a slight inhibition of the assay, while a control antibody to keyhole limpet hemocyanin (KLH) caused little effect. Treatment with δTCS1, however, resulted in a significant enhancement of the lysis.

In summary, the activity of some subsets of γδ positive cells may be cytotoxic and it may be possible to enhance the killing activity of this subset by treatment with δTCS1 monoclonal antibody. This antibody also shows mitogenic activity (Wu, Y-J., et al., 1988, J. Immunol., 141, 1476–1479). Using appropriate amounts of antibody, δTCS1 binds to the surface of γδ positive cells and stimulates the proliferation of a minor cell population of resting human PBL to levels where the proportion of γδ positive cells in the culture exceeds 90%.

9.2.3.3. Suppressor Activity of γδ Positive ST Cell Lines

For the suppression assays, fresh peripheral blood lymphocytes were prepared and then stimulated with either PHA or anti-CD3 monoclonal antibody. The inhibition of the proliferation of these cells was tested by adding varying dilutions of supernatant fluid obtained from the cell cultures of ST-25 and ST-32 cell lines. Supernatant fluid from both ST-25 and ST-32 cell lines suppressed the proliferation of PHA or anti-CD3 stimulated PBLs. This suppression was observed at supernatant dilutions exceeding 1:1024 for ST-32 and 1:256 for ST-25. The factors are soluble and are not removed by dialysis overnight at 4° C. (molecular weight cutoff of 3,000). The antibody, δTCS1, is mitogenic for γδ$^+$ cells (see 9.3.3.2, supra) and it may be that, following the triggering of these cells with the antibody, suppressor factors are produced. This would result in the ability to modulate this affect in the γδ$^+$ T cell subset by using the appropriate dosage of antibody.

9.2.4. Blocking of the Cytotoxicity Reaction By δTCS1

To establish the ability of δTCS1 monoclonal antibody to block the cytotoxic activity of δTCS1$^+$ effector cells against specific and non-specific target cells, the RA derived effector cells may be preincubated with δTCS1 antibody using a range of concentrations. To distinguish between Fc receptor dependent killing and δTCS1 specific blocking in the cytotoxicity assays, both whole antibody and Fab fragments of δTCS1 antibody may be tested. The whole antibody may be used to give rise to Fc receptor mediated killing, whereas the Fab fragment (which has the Fc portion of the antibody removed) may be used to effect specific blocking of γδ$^+$ effector cell cytotoxic activity.

9.2.5. Depletion Assay Using δTCS1

To establish the ability of δTCS1 monoclonal antibody to modulate γδ$^+$ T cells and cause their specific elmination in vitro, δTCS1 may be tested in complement mediated lysis assays. For these assays, RA derived effector cells may be preincubated with δTCS1 antibody using a range of concentrations. Following preincubation, rabbit serum may be added as a source of complement pathway components. With the appropriate concentrations of δTCS1, the complement cascade may become activated leading to complement dependent lysis of the δTCS1+ cells and their depletion from the cell population. Effective in vivo concentrations of δTCS1 for T cell elimination may be estimated to be approximately equal to those observed for the therapeutic monoclonal antibody, OKT3 (see Example 10, infra).

9.3. Discussion

The results of this study provide phenotypic and functional evidence that specific T cell recruitment occurs in rheumatoid arthritis joints. It is well known that CD4+ T cells infiltrate the diseased synovium and are in close contact with HLA DR+ synoviocytes (Iguchi, T., et al., 1986, Arth. Rheum., 29, 600; Harris, E. D., Amer. J. Med., 80, 4). This close association of T cells and HLA DR+ tissue macrophage-like cells is thought to be responsible for propagating the inflammatory response in the synovium of RA patients. The exact nature, or even the existence of specific antigens causing RA is unclear. However, it is believed that antigens may be presented by the synoviocytes with elevated HLA DR, the appropriate class II restricting element for CD4+ cells. Therefore, we isolated and expanded the diseased tissue-infiltrated T cells for phenotypic and functional characterization with a specific focus on the interaction of those T cells and the other cell types found in the diseased, autologous synovium.

A novel functional response from synovial tissue-derived T cells was observed. Short-term cultured lines and cloned T cells from diseased joints were able to specifically lyse autologous Type A macrophage-like synoviocytes, in vitro. Previous studies have shown that peripheral blood derived T cells could lyse synovial type B fibroblasts, however, this was observed primarily against allogeneic fibroblasts (Griffiths, M. M., et al., 1976, J. Clin. Invest., 58, 613; Person, D. A., et al., 1876, J. Clin. Invest., 58, 690). Our data represents the first report of autologous Type A synoviocyte cytotoxicity by synovial tissue derived T cells, and the lytic activity we observed in the PB-T lines was mostly of an NK-like nature. The structure(s) recognized by the ST-lines and clones are not known; however, it does not appear to be class II antigen alone since DR+ autologous peripheral blood macrophages and B cells were not killed in the same assays. Attempts are ongoing to isolate adequate numbers of Type A cells for future molecular analysis of unique proteins. In the meantime, T cells exhibiting this unique pattern of target cell recognition are abundant.

Cell surface staining with a monoclonal antibody which recognized the second type of T cell antigen receptor, $\gamma\delta$ cells, showed that RA synovium contained significantly higher numbers of $\gamma\delta+$ T cells than those found in peripheral blood of the same patient. In addition, those gamma delta+ cells were not from a double negative CD4-CD8-population since they stained brightly for either CD8 or CD4 in those patients studied by double immunofluorescence. The selection of $\gamma\delta+$ T cells seen in RA synovium but not in non-RA synovium has not been previously reported. The specificity and function of human $\gamma\delta$ T cells is not yet fully understood; however, preliminary reports suggest that they may be HLA-unrestricted killer cells (Faure, F., et al., 1988, J. Immunol., 140, 1372) and murine $\gamma\delta$ cells are thought to be alloreactive (Maeda, K., et al., 1987, Proc. Natl. Acad. Sci. U.S.A., 84, 6536; Matis, L. A., et al., 1987, Nature, 330, 262). Preliminary information on the cytotoxicity of the RA-derived $\gamma\delta$ + T cell lines indicates some direct alloreactivity in ST-28 line while no detectable alloreactivity was observed with the others tested.

The synovial tissue of RA patients is known to be infiltrated with the helper-inducer subset of T cells by immunofluorescence of frozen membrane sections (Duke, O., et al., 1987, Arth. Rheum., 30, 849). We have confirmed this observation using isolated T cells obtained from pieces of synovium cultured in the presence of IL-2 medium. There is some discrepancy concerning the ratio of CD4+ to CD8+ cells in the peripheral blood of RA patients. Some reports indicate an increased number of CD4+ cells (Fox, R. I., et al., 1982, J. Immunol., 128, 351), others show a decrease in the CD4+ cells (Forre, O., et al., 1982, Scand. J. Immunol., 15, 221) and still others observe no change in the T cell ratios in peripheral blood (Silverman, H. A., et al., 1976 Arth. Rheum., 19, 509). Our data demonstrates a decreased relative number of CD4+ cells and an increased number of CD8+ cells as compared to the values found in PHA stimulated peripheral blood, resulting in a lower than normal ratio of CD4/CD8 cells. In addition, we found a lower than normal level of 2H4+ cells in the peripheral blood of RA patients; however, the defect in suppressor-inducer cells is more dramatic in the tissue than in the blood. Moreover, the major T cells involved in the pathogenesis of joint damage are the helper-inducer T cells and the normal counterbalance provided by the suppressor-inducer cells was lacking in the joint and reduced in the periphery of RA patients.

Several reports have indicated that the T cell abnormalities in RA include diminished suppressor cell activity, decreased mitogenic responses and increased antibody production (Silverman, H. Aa., et al., 1976, Arth. Rheuem., 19, 509; Indiveri, F., et al., 1986, Cell. Immunol., 97, 197; Wernick, R. Mm., et al., 1985, Aarth, Rheum., 28, 742). Also, depressed lymphokine production and responsiveness have been reported for both IL-2 and gamma-interferon (Lotz, M., et al., 1986, J. Immunol., 136, 3643; Husby, B. and Williams, R. C., 1985, Arth. Rheum., 28, 174). In most cases, however, T cell responses were not measured in the context of synovial tissue-derived antigens. Our data demonstrated the effector function against autologous synovial tissue-derived antigens. The cytotoxicity does not appear to be mediated by NK-like mechanisms. Evidence for this tissue specificity in vivo is yet to be determined but the implication is that the infiltrating T cells may be directly contributing to the membrane damage in the disease process. In fact, the quantitative relationship between Type A and Type B synoviocytes in the synovial membrane is known to be altered in RA (Carson, D. A. and Fox, R. I., 1985, In "Arthritis and Allied Conditions", McCarty, D. J. (Ed.), p. 257). An increased number of Type A cells early in the synovitis may even provide a mechanism of selection in directed homing of T cells capable of recognizing Type A antigen(s). This hypothesis of T cell selection in the diseased joint is supported by the finding that T cells in the PB of RA patients did not exhibit the same pattern of target specificity as T cells cloned directly from the synovium. Additional evidence for a disease-related T cell migration into the synovium may include the lack of Type A specificity in the T cells derived from non-RA synovium, but more patient samples must first be tested.

In summary, we provide evidence of a novel functional specificity mediated by RA synovial-derived T cells. T cells from RA peripheral blood or non-RA synovium did not show any preferential target cell lysis which indicated that the unique structure(s) recognized by synovial tissue lines may be disease related. Many of the synovial tissue lines exhibited a significantly higher percentage of $\gamma\delta+$ T cell antigen receptors as compared to either peripheral blood or non-RA synovial-derived T cells. In contrast, the CD4/CD8 ratios and 4B4/2H4 ratios were similar in ST-lines and NST-lines implying no disease correlation with these classes of T cell subsets infiltrating the synovial membrane. Because of this, the nature of the TCAR specificity should be more informative than studying the surface CD4, CD8, 4B4, 2H4 or similar surface phenotypes of T cell subsets. Most data to date support the hypothesis that RA patients, as well as other autoimmune patients (Maeda, K., et al., 1987, Proc. Natl. Acad. Sci. U.S.A., 84, 6536), lack sufficient suppressor cells to control autoreactivity. Our findings are consistent with an aggressive, but novel, autoreactivity and depressed suppressor inducer T cells in RA patients. Studies are underway to study the molecular nature of the T cell antigen receptors found in the diseased synovium (see Example 8, supra and Example 11, infra) and should provide information on the autoimmune mechanisms propagating chronic RA. The contribution of T cell-mediated Type A synoviocyte destruction in RA or other inflammatory arthrophathies remains unclear and is being studied further.

10. EXAMPLE: δTCS1, A MONOCLONAL ANTIBODY REACTIVE WITH THE Vδ1 REGION OF HUMAN T CELL ANTIGEN RECEPTOR, IS USEFUL IN THE TREATMENT OF RHEUMATOID ARTHRITIS

Our results show that under different conditions, the antibody δTCS1 can specifically modulate the activity of a subset of γδ$^+$ T cells. These cells are elevated in the synovial fluid and peripheral blood of RA patients and in the peripheral blood of Felty's patients. In addition, they are present in the population of T cells that infiltrates the inflamed synovial tissue of RA patients. Improved therapies can be developed using δTCS1, because this antibody can selectively modulate a specific disease related subset of T cells and not affect other T cell populations. Depending upon the dosage of antibody used, δTCS1 based immunotherapies will either stimulate the specific T cell subset or cause it's elimination from the body; and enhance or block the T cell subset's function. For anti-CD3 monoclonal antibody treatments, different elimination and stimulation therapies have been described (Chatenoud et al., 1982, Eur. J. Immunol. 12:979–982; Hirsch et al., 1989, J. Immunol. 142:737–743; Chatenoud et al., 1988, C. R. Acad. Sci. Paris, 307:833–836). The protocol given below as an example is one designed to specifically deplete δTCS1$^+$ T cells from patients in whom their presence is deleterious.

10.1. Preclinical Data

10.1.1. Peripheral Blood Study In RA and Felty's Patients

During a preliminary study of the T cell subsets in RA patients in 1987, we observed a patient with extremely elevated δTCS1+ T cells (70%) in his blood. Upon further inquiry, the patient was diagnosed to have Felty's Syndrome. To date, our study of γδ+T cells in disease has included 40 RA patients, 11 Felty's patients, 5 non-RA joint disease patients and 22 age matched normals. As shown in Example 8, 45.5% of the Felty's and 27.5% of the RA patients showed significant elevations of δTCS1$^+$ T cells (mean of normal plus 2 standard deviations) in peripheral blood.

The prevalence of various autoimmune diseases is associated with well defined HLA phenotypes (see Table 13).

TABLE 13

Some HLA-DR-Associated Autoimmune Diseases

| Disease | HLA Type | PATIENT % | NORMAL % | Relative Risk |
|---|---|---|---|---|
| Felty's Syndrome | DR4 | 95 | 20 | 76 |
| RA with Vasculitis | DR4 | 95 | 20 | 76 |
| RA | DR4 | 68 | 25 | 3.8 |
| IDDM | DR4 | 72 | 24 | 9.1 |
|  | DR3 | 49 | 22 | 4.3 |

RA = Rheumatoid Arthritis
IDDM = Insulin dependent diabetes mellitus

If Felty's Disease patients or RA patients are further divided into sub-groups based upon their HLA DR and Dw phenotypes, it is probable that the elevation of δTCS1$^+$ T cells will correlate even more strongly with disease.

10.1.2. Longitudinal Studies

It is expected that the elevation of δTCS1$^+$ T cells in RA or Felty's will correlate with disease state (e.g., tender joints, vasculitis, etc.). In addition, it is well known that female RA patients undergo remission of symptoms shortly after becoming pregnant. Their symptoms return again after giving birth. Longitudinal studies are underway to study the levels of δTCS1$^+$ T cells in RA and Felty's patients and in pregnant women. These numbers may then be correlated with the intensity of the disease during these stages. This data may be used to subdivide patients that would benefit from δTCS1 therapies designed to modulate (eliminate or block or stimulate or enhance) the δTCS1$^+$ T cell subset.

10.1.3. Synovial Fluid and Synovium Tissue Study

Analysis of RA synovium-derived T cells upon expansion in IL2 supplemented culture fluid and of synovial fluid T cells yielded elevated levels of δTCS1$^+$ cells in RA patients as was seen for peripheral blood (see Examples 8 & 9, supra). In many RA samples, paired blood and synovium tissues from the same patients were studied (see Example 9, supra). Furthermore, we further evaluated the δTCS1$^+$ T cells in RA synovium by using in situ immunohistochemistry (Example 8, supra). 6 out of 11 RA patients studied showed significant infiltration of δTCS1$^+$ T cells in synovium. This indicated that the elevation of δTCS1 was not due to a bias in cell growth during in vitro culture conditions. The detailed relationship between the δTCS1$^+$ T cells in the blood and synovium of the same RA patient is being investigated further.

10.1.4. Activity of γδ$^+$ T Cells in Rheumatoid Arthritis

The γδ$^+$ cells from some RA synovial tissue derived T cell lines possessed cytotoxic activity against their autologous type A synoviocytes, and other lines produced factors with suppressor activity. The antibody, δTCS1, was able, under varied conditions, to either enhance the cytotoxic activity, to mitogenically stimulate the cells, or to block the activity of the cells (Example 9, supra).

Taken together the data suggests that δTCS1$^+$ T cells play a significant role in the pathogenesis of rheumatoid arthritis patients and that it can be used as a T cell receptor-specific therapeutic.

10.1.5. αβ T Cell Analysis in Arthritis

Evidence has been generated that T cells infiltrating synovium of some RA patients primarily express Vβ3, Vβ9, and Vβ10(Example 11, infra). These 3 Vβ's together account for 5% of total T cells in normal subjects. This demonstrated that distinct subsets of T cells that represent only a small fraction of the T cells in normal subjects may be preferentially associated with some RA patients. Thus, it appears that at least two distinct groups of RA patients can be determined based upon TCAR expression; the first group expresses Vβ3, Vβ9, or Vβ10 in the synovium, while the second group expresses primarily Vδ1.

10.1.6. Toxicology of δTCS1 Monoclonal Antibody

The acute and chronic toxicity of δTCS1 antibody may be determined by standard animal model procedures. However, data has been collected with other similar antibodies; e.g. OKT3. The documented information supports the general safety of mouse IgG$_{2a}$ antibody administered to human subjects in amounts up to several grams per person per day (ORTHOCLONE OKT3 (MUROMONAB-CD3) Product Insert, Ortho Pharmaceutical Corp., Raritan, N.J.).

The question of possible cross reactivity of δTCS1 antibody with other human tissues has been examined. It does not appear to react with any of the other blood cell types, such as neutrophils, monocytes and red blood cells, nor with tissues in the gastrointestinal tracts. It does, however, weakly react with some Langerhans cells in the skin and some intracellular antigen in the glandular cells of endometrium.

Sensitization to a murine monoclonal antibody, such as OKT3, has been observed in most patients under treatment, but has not produced significant symptoms of hypersensitivity, anaphylaxis or serum sickness (ORHTOCLONE OKT3 (MUROMONAB-CD3) Product insert, Ortho Pharmaceutical Corp., Raritan, N.J.). Similar results may be expected for δTCS1.

Almost all of the patients treated with OKT3 developed an acute symptom complex with chills and fever after the first injection. This typically commenced 45–60 minutes after the antibody injection and lasted for several hours. This acute symptom was presumed to be due to a physiological response to the rapid lysis of large numbers of T cells during the therapy (ORTHOCLONE (MUROMONAB-CD3 Product insert, supra). Since δTCS1 antibody will lyse a significantly smaller number of T cells (about 1%), the severity of the side effects associated with OKT3 should be minimized.

10.1.7. Pharmacokinetics of δTCS1 Monoclonal Antibody

Data on the pharmacokinetics or pharmacology of δTCS1 antibody may be determined by standard animal model techniques. However, data on this important information has been collected with other mouse monoclonal antibodies, such as OKT3, which may be applicable to δTCS1 antibody.

With a single bolus I.V. injection of 5 mg of OKT3 in a normal subject, the average half life of the antibody averages about 4 hours. During treatment with 5 mg per day for 14 days, mean serum levels of the drug rose increased the first three days and then averaged 0.9 $\mu$g/ml on days 3 to 14 (ORTHOCLONE (MUROMONAB-CD3) Product Insert, supra).

10.1.8. Physical Biochemical Properties of δTCS1 Monoclonal Antibody

The δTCS1 monclonal antibody was generated by fusion of myeloma cells with splenocytes derived from a BALB/c mouse immunized with a human leukemic cell line, Molt 13. Detailed screening, cloning selection, and characterization procedures have been published (Wu, Y-J., et al., 1988, J. Immunol., 141, 1476–1479) and are incorporated by reference herein.

The antibody was initially produced as an IgG1 isotype. To improve the antibody dependent cytotoxicity (ADCC), which is the key in vivo mechanism for cell elimination, an IgG$_{2a}$ variant was selected as described in Section 5.2, supra.

The parent IgG1 isotype and isotype switched IgG$_{2a}$ antibodies were tested by Ouchterloney diffusion, ELISA isotype test, and competition assay. F(ab)$_2$ fragments were also generated and characterized by polyacrylamide gel electrophoresis.

The physiochemical properties of the variant are identical to that of the IgG1 parent in terms of mitogenic properties, cell reactivities and binding. The IgG$_{2a}$ δTCS1 antibody will be used as the therapeutic drug for an elimination protocol.

10.2. Clinical Plan for Elimination Protocol

Since one of the therapeutically important properties of δTCS1 monoclonal antibody may be to target the specific δTCS1$^+$ T cell subset for elimination, the following plan is given as a example of this type of protocol.

10.2.1. Indication

The intended indication will be for use as adjunctive therapy for treating RA patients who fail or are contraindicated for conventional second line drugs.

10.2.2. Patient Admission Criteria to the Study

RA patients who may be enrolled in the study include those who A) exhibit 5% or greater of δTCS1$^+$ T cells in the peripheral blood, and B) failed the conventional second line drugs. The screening will be based on the immunofluorescense staining of potential patients' lymphocytes with δTCS1 monoclonal antibody. It is estimated that at least 10 out of 50 severe RA patients screened may be suitable for the study.

10.2.3. Clinical Endpoint

The initial clinical endpoint relates to a substantial reduction of δTCS1$^+$ T cells and possibly other T cell subsets in circulation within 2 hours after the drug's administration. This will be carried out by the immunofluorescence procedure described above.

The long-term clinical endpoint may be evaluated by clinically monitoring patients and lab indices approved by the American Rheumatism Association (FIG. 17). The first signs of clinical improvements may come from the reduction of tender joint counts and duration of morning stiffness.

10.2.4. Calculation of Drug Dose

A similar approach used for the calculation of OKT3 dose may be employed. Assuming 1) there are 7 liters of blood in an adult, 2) there are 1×10$^8$ δTCS1$^+$ T cells (10% of total T cells in RA) per liter of blood in RA patients, 3) δTCS1$^+$ T cells sequestered in lymphoid tissues equals to that of blood, 4) it will require 15 $\mu$g of δTCS1$^+$ monoclonal antibody (Ab) for 10$^8$ T cells to induce effective cell elimination or block of cell receptor function in vivo and 5) 5% of injected δTCS1$^+$ antibody is bioavailable, then the calculated dose is 2.1 mg per dose (see below.

(7000 ml blood/patient×1×10$^8$cells/×1000 ml blood ×15 $\mu$g Ab/10$^8$ cells×1/0.005=2.1 mg AB/patient

10.2.5. Regimen

The in vivo half life of mouse IgG$_{2a}$ monoclonal antibody, known to one skilled in the art, averages around 4 hours. Therefore, a daily injection of about 2 mg per patient for 10 to 14 days is recommended in order to achieve optimal efficiency.

10.3. Summary

It is clear that lymphocytes are actively involved in the pathogenesis of Rheumatoid Arthritis (RA). Severe RA patients alone represent at least a million people in the United States. Although immunosuppression therapies, such as total lymphoid irradiation, and thoracic duct drainage, are efficacious for severe RA patients, but they are not suitable for all patients. To date, no satisfactory immunotherapy is available for severe RA patients who have failed or contraindicated for conventional second line drugs.

We have obtained evidence that about 1% of total T cells are involved in severe RA. An improved, novel, safer and efficacious immunotherapy of selectively eliminating the same 1% of total T cells in the body, using δTCS1 monoclonal antibody, has been developed. The best currently employed experimental drug abolishes 60% of T cells, leading to generalized immune suppression and raising serious issues relating to patient risk/benefit.

Studies of the infiltrated cells revealed that T cells represent the major cell type at the site of tissue injury, that is, the synovium of the RA joints. These T cells have been the main target for other immunosuppressive drugs. Several independent studies indicate that synovial T cells are primarily CD4$^+$ helper T cells. Our data suggests that these synovial T cells bear two distinct types of T cell antigen receptors (TCR), namely, the αβ and the γδ TCR. Our evidence strongly suggests that a subset of γδ cells, identifiable by the δTCS-1 antibody, is significantly elevated in the blood and/or synovium of about 20–30% of RA patients. These patients tend to develop more severe forms of arthritis, i.e., Felty's Syndrome and RA with associated peripheral vasculitis. The lack of appropriate animal models, the historical excellent safety record of mouse monoclonal antibody products, and the severity of RA disease leads us to believe that it is timely to proceed with the drug development of the δTCS1 antibody as a useful therapeutic drug for arthritis patients.

It has been noted that δTCS1$^+$ T cells represent about 1% of total T cells in healthy individuals. They are postulated to regulate the development of αβ T cells via the lymphokines they secrete and to represent the motile population of γδ T cells in the body. The only FDA approved mouse monoclonal antibody, therapeutic OKT3, eliminates 100% of T cells, and the therapy requires supportive measures in a hospital setting for administration. However, with a 10–14 day course of daily OKT3 injections, the therapeutic effects lasted for about one to two years in treated patients who suffered from transplanted kidney rejection.

We propose to treat severe RA patients with δTCS1$^+$ monoclonal antibody by administering a daily I.V. dose of approximately 2 mg of the antibody for 10–14 days. The therapy is expected to be primarily maintained by outpatient administration.

11. EXAMPLE: MONOCLONAL Antibodies REACTIVE WITH THE VARIABLE REGIONS OF α,β HUMAN T CELL ANTIGEN RECEPTOR ARE USEFUL IN THE TREATMENT OF RHEUMATOID ARTHRITIS The first step needed in the development of T cell receptor specific therapeutics is to correlate specific T cell receptor gene usage with disease. Once it is known which T cell receptors (TCRs) are primarily involved in the disease, specific therapeutics can be produced.

A panel of TCR variable region genes were used to determine which variable regions correlate with rheumatoid arthritis. The data presented infra involves the analysis of rheumatoid arthritis patient samples using $V_\alpha$ and $V_\beta$ TCR gene probes. Similar analysis could also be done using $V_{65}$ and $V_{67}$ genes as well.

11.1. Materials and Methods

11.1.1. Samples

Paired synovial membrane derived T cell lines and peripheral blood T cell lines were prepared from 12 patients with RA (see Example 9, infra). Peripheral blood lines were also obtained from 5 normal individuals for controls using similar cell culture procedures.

11.1.2. T Cell Receptor Variable Region Gene Probes

There are 17 human $V_\alpha$ and 18 human $V_\beta$ subfamilies that have been identified to date (Toyonaga, B. and Mak, T. W., 1987, Annual Rev. Immunol., 5, 585–620). These Vβ subfamilies are named Vβ1 to Vβ 20. Subfamilies designated Vβ13 and Vβ14 have been merged into other families based upon the degree of sequence homology of the members. All except $V_{\alpha 15}$ and $V_{\beta 16}$ have currently been tested. In addition, there are about 5–10 human $V_\gamma$ (Forster, A., et al., 1987, EMBO, 6, 1945–1950) and 5–10 human $V_\delta$ (Takihara, Y., et al., 1989, J. Exp. Med., 169, 393) subfamilies that have been identified to date. As additional V α, β, γ, and δ regions become available, they may similarly be tested. Once correlations between disease and specific TCR V subfamilies have been identified, the specific member of the subfamily responsible for the correlation can also be identified (see infra).

11.1.3. RNA Preparations

RNA was isolated by the guanidinium isothiocyanate cesium chloride procedure (Maniatis, T., et al., 1982, In "Molecular Cloning: A Laboratory Manual", Cold Spring Harbor Laboratories, N.Y.). Total RNA was precipitated twice in 0.3 M sodium acetate and 2.5 volumes of ethanol. On average, 5 to 10 μg of total RNA was obtained from 10 million cultured T cells.

11.1.4. T Cell antigen Receptor Usage Analysis

The usage of T cell antigen receptor α and β chains in the T cell lines was determined using 3 major steps; i) cDNA synthesis; ii) polymerase chain reaction amplification; and iii) DNA slot blot analysis.

11.1.4.1. cDNA Synthesis

Five μg of total RNA from each sample was primed for cDNA synthesis using the $C_\alpha$ olignucleotide and a $C_{62}$ oligonucleotide. To analyze TCR γ,δ gene usage, $C_{67}$ and $C_{67}$ primers could be used in an analagous fashion. Both $C_\alpha$ and $C_\beta$ primers were 18-mers synthesized by New England Biolabs, Beverly, Mass. using the published sequences of the α and β constant regions (Yanagi, Y., et al., 1984, Nature, 308, 145–149). The sequence of the $C_\beta$ primer (5'-TTAGAGTCTCTCAGCTGG-3') is located 31 nucleotides 3' from the NH$_2$ terminus of the α chain constant region. The sequence for the $C_\beta$ primer (5'-TTCTGATGGCTCAAACAC-3') is located 36 nucleotides 3' from the NH$_2$ terminus of the β chain constant region. The $C_\beta$ oligonucleotide primed cDNA synthesis from both β chain constant regions (Yanagi, Y., et al., 1984, Nature, 308, 145–149; Jones, N., et al., 1985, Science, 227, 311–314). The location of these primers was chosen such that the synthesized cDNA would comprise the variable, diversity, and joining regions of the T cell receptor mRNA and only a small portion of the constant region.

First strand DNA synthesis was performed according to published procedures (Okayama, H. and Berg, P., 1982, Mol. Cell. Biol., 2, 161–170; Gubler, U. and Hoffman, B. J., 1983, Gene, 25, 263–269) except that the reaction was terminated prior to synthesis of the second strand. The resulting templates were in the form of RNA:DNA hybrids. These duplexes were then used in an oligo-dG tailing reaction (Deng, G-R. and Wu, R., 1983, Meth, in Enzymol., 100, 96–117) which preferentially tails the 3' end of the cDNA strand over the RNA strand.

11.1.4.2. Polymerase Chain Reaction (PCR) Amplification

The PCR reaction was performed in a thermocycler (Perkin-Elmer, Norwalk, Conn.) using recombinant Taq DNA polymerase (Cetus Corp., Emeryville, Calif.). Oligonucleotides $d(C)_{10}$, and $C_\alpha$ and $C_\beta$, were used as primers for amplification. The PCR amplification procedure of Loh, E. Y., et al. (1989, Science, 243, 217–220) was used with the following modifications. PCR amplification was done for 30 cycles with each cycle comprising incubations at 92° C. for 1 minute, 50° C. for 1.5 minutes and 72° C. for 2.5 minutes. The last extension reaction was for 10 minutes at 72° C. All samples were amplified a total of 3 times with isolation of the amplified DNA fragment of about 300–400 base pairs between each round. The final amplified DNA samples were then precipitated with spermine to remove free nucleotides, before labeling with $^{32}P$ radiolabeled nucleotides. Labeling was done during 5 cycles of PCR amplification using all four $^{32}P$ labeled nucleotides at a ratio of 1:10 non-radiolabeled nucleotides. The resulting $^{32}P$ labeled DNAs were purified on elute-tip™ columns (Schleicher & Schuell, Keene, N.H.) to remove non-incorporated $^{32}P$ nucleotides.

11.1.4.3. DNA Slot Blot Analysis

DNA slot blots were prepared using a slot blot apparatus (Schleicher & Schuell, Keene, N.H.) and nylon membranes (Oncor, Gaithersburg, Md.) according to manufacturer's protocols. A panel of cDNA subclones comprising the variable region of $\alpha$ and $\beta$ chain TCR genes was spotted in duplicate on each slot blot (3 µg per slot). After the blots had been prepared containing the panel of TCR V region DNAs, individual blots were then hybridized to the $^{32}P$ labeled T cell derived cDNA generated in step #2. Individual patient samples were hybridized to duplicate blots. Hybridization condition and washes (Southern, E., 1979, J. Mol. Biol., 98, 503–517) were chosen to ensure no cross-hybridization between members of different subfamilies. The wash steps were performed at 42° C. in 0.2×SSC (30 mM sodium chloride, 3 mM sodium citrate, pH 7.4) with 0.1% sodium dodecyl sulfate using 4 washes of 20 minutes each. Following washing, the blots were blotted dry, and other autoradiographed at −70° C. for 2–6 days using Eastman Kodak, X-Omat Xray film (Rochester, N.Y.). The developed autoradiographs were than scanned for intensity using a video densitometer (Model 620, Biorad Corp., Richmond, Calif.)

11.2. Results

Even in a normal disease free state, the expression of TCRs varies for the different subfamilies. Some subfamilies, e.g. V$\beta$8, V$\beta$6 and V$\alpha$10, are expressed quite frequently and the expression of others is fairly rare. For disease correlation, the increased levels of expression in disease are determined relative to these base levels.

Using the cDNA synthesis, PCR amplification and slot blot hybridization procedure detailed in the materials and methods, paired RA samples including peripheral blood and synovial tissue derived T cell lines from each of 12 patients were analyzed relative to the expression in 5 normal peripheral blood controls. One basic assumption in this analysis is that the disease related T cells are most abundant at the site of the disease, e.g. the synovial membrane of patients with rheumatoid arthritis.

An example of this analysis is shown in FIG. 18. The left panel of FIG. 18, shows the autoradiograph obtained when the T cell line ST-2 obtained from synovial tissue infiltrating lymphocytes was analyzed with the panel of V$\beta$ TCR genes. The right side of this figure shows the densitometry trace. In this cell line, it is clear that several TCR V$\beta$ genes (V$\beta$'s 2, 4, 6, 7, 8, 11 and 18) are expressed with V$\beta$4 being expressed in highest amounts. To determine which of these correlate with disease, this pattern of expression was compared to the pattern of expression observed in the peripheral blood derived T cell line (see FIGS. 19 and 20).

FIG. 19 tabulates the results observed for V$\beta$ gene expression in each of the paired synovium tissue and peripheral blood derived T cell lines from the 12 RA patients analyzed. The X axis represents the number of patient samples (12 total) where a V$\beta$ was observed by the densitometry analysis as illustrated in FIG. 18 for the ST-2 cell line. The Y axis represents each of the 16 V$\beta$ gene probes tested. Peripheral blood data is represented by a crosshatched bar and synovial tissue data is represented by an open bar for each V$\beta$. From this figure, it can be determined that in the 12 RA patient samples analyzed, V$\beta$3, V$\beta$9, V$\beta$10 and V$\beta$12 were expressed more often in the synovial tissue derived T cell lines than in the peripheral blood derived T cell lines. For example, the ratio of presence in synovium to presence in the peripheral blood sample was found to be 1.4 V$\beta$3. By this analysis, the most frequently expressed V$\beta$ genes in the synovium relative to the peripheral blood were V$\beta$3, V$\beta$9, V$\beta$10 and V$\beta$12.

When the same data was analyzed as shown in FIG. 20, the frequently used genes were V$\beta$1 (ratio=4.0), V$\beta$ 3 (ratio=infinity), V$\beta$6 (ratio=3.0), V$\beta$9 (ratio=infinity), and V$\beta$10 (ration=infinity). For the analysis in FIG. 20 only the dominant V$\beta$ in each sample as determined by the desitometry trace was used; the assumption being that although the T cell line may contain varying subpopulations of T cells, the dominant subpopulation could be the most relevant one. The frequencies of V$\beta$3, V$\beta$9, and V$\beta$10 were high when the data from the 12 patients was analyzed either for total expression or dominant expression.

When the same samples were analyzed for total V$\alpha$ gene expression (FIG. 21), the results were less clear. The reason for this turned out to be that 85% of the synovium or peripheral blood derived T cell lines analyzed preferentially used V$\alpha$10 (FIG. 22). Although other V$\alpha$'s were also represented in the cell line populations. V$\alpha$10 was by far the dominant one with the densitometry peak height for V$\alpha$10 being 100 fold greater than those of the other 15 V$\alpha$ genes. This raises the possibility that V$\alpha$10 may represent a universal V$\alpha$ that can pair well with most V$\beta$ chains. FIG. 21 shows that V$\alpha$12 (ratio=infinity) may be the next most commonly expressed V$\alpha$ gene in synovium, but its level of expression is low when compared to the level of expression of V$\alpha$10.

11.3. Summary

This analysis has shown that T cell populations at the site of disease, e.g. the joint synovial membrane, appear to predominantly express specific V$\beta$ chains. One mechanism of autoimmunity may be that disease-related autoantigens are recognized by the body's own T cells via specific T cell antigen receptor $\alpha$, $\beta$, $\gamma$ and $\delta$ chains. After antigen recognition, these T cells clonally expand to give rise to an oligoclonal population of disease-related T cells. Other mechanisms that may be involved include recruitment of specific cells to the disease site which would then represent an oligoclonal population of cells. In the total population of cells present at the disease site, the oligoclonal cells can be detected, as they will be using the TCR variable regions that are most frequently expressed. To date, our study has shown that the most frequently expressed Vβ genes in the synovial membrane of 12 RA patients were Vβ3, Vβ9, and Vβ10 and Vδ1 was preferentially used in the γδ+ T cells present in synovial fluid. To refine this correlation even more, patient HLA type, disease state and expression of TCR genes for α, β, γ and δ chains and for TCR Diversity-Joining region expression may be determined. It is expected that as patients are subgrouped by HLA type, the disease correlations will become even stronger.

11.4. Discussion: Treatment of Rheumatoid Arthritis PATIENTS WITH TCR α, β SPECIFIC REAGENTS Once a disease correlation has been made between a disease state and specific TCR gene expression, then the next step is to develop the TCR specific therapeutics. One class of such therapeutics are anti-TCR antibodies.

For the analysis presented supra on the preferential use of 3 Vβ genes in rheumatoid arthritis patients, it is envisioned that a specific therapeutic would involve a multiple antibody cocktail of anti-TCR antibodies specific for Vβ3, Vβ9 and Vβ10. This therapeutic would thus target only the T cell subsets expressing these 3 Vβ TCRs and not effect other non-expressing T cells.

12. DEPOSIT OF HYBRIDOMAS

The following hybridoma cell lines, producing the indicated monoclonal antibody, have been deposited with the American Type Culture Collection, 1234 Parklawn Drive Rockville, Md. 20852 U.S.A., and have been assigned the listed accession numbers:

| Hybridoma | Monoclonal Antibody | Accession Number |
| --- | --- | --- |
| δTCAR-3 | δTCS1 (δTCAR-3) | HB 9578 |
| 3A8 | αF1 | HB 9900 |
| 3D6 | αF2 | HB 9901 |
| W112 6G-2 | W112 | HB 9927 |
| 2D1 | 2D1 | HB 9928 |
| 5.A6.E9 | Anti-TCRδ1 | HB 9772 |
| RS2A-2-H-7 | δTCS1, isotype IgG2a | HB 10110 |

Hybridoma W112 6G-2, assigned accession number HB 9927, was deposited with the American Type Culture Collection on Dec. 15, 1988.

The present invention is not to be limited in scope by the cell lines deposited since the deposited embodiments are intended as single illustrations of one aspect of the invention and any cell lines which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

Various publications are cited herein, the disclosures of which are incorporated by reference in their entireties.

What is claimed is:

1. An isolated monoclonal antibody or fragment thereof reactive with an epitope of the Vβ5.3 variable region of the beta chain of a T cell antigen receptor, wherein said monoclonal antibody modulates a β chain 5.3 variable region expressing T cell subset in a mammal.

2. The monoclonal antibody, or fragment of claim 1 wherein the antibody is reactive with the same epitope as the monoclonal antibody W112, as produced by the hybridoma deposited with the ATCC and assigned accession number HB 9927.

3. A hybridoma cell line which produces the monoclonal antibody of claim 1.

4. A monoclonal antibody or fragment according to claim 1 which is detectably labeled.

5. Monoclonal antibody W112, as produced by the hybridoma deposited with the ATCC and assigned accession number HB 9927.

6. The Fv, Fab, Fab', or F(ab')$_2$ fragment of the monoclonal antibody of claim 1 or 5.

7. A monoclonal antibody fragment according to claim 6 which is detectably labeled.

8. An antibody comprising the Fv, Fab, Fab', or F(ab')$_2$ fragment of the monoclonal antibody of claim 5.

9. Monoclonal antibody W112 according to claim 5 which is detectably labeled.

10. A hybridoma cell line, deposited with the ATCC and assigned accession number HB 9927, which produces monoclonal antibody W112.

11. A method for diagnosing in a patient an immune disorder correlated with a Vβ5.3 T cell subset, comprising:
    (a) contacting a body fluid or body tissue of said patient with a monoclonal antibody or fragment thereof reactive with an epitope of the Vβ5.3 variable region of the beta chain of a T cell antigen receptor; and
    (b) detecting whether immunospecific binding has occurred.

12. The method of claim 10 in which the body fluid or tissue is contacted in vitro.

13. The method of claim 11 in which the tissue is contacted in a histologic specimen.

14. The method of claim 11 in which the body fluid or tissue is contacted in vivo.

15. The method of claim 1, in which the monoclonal antibody is W112, as produced by the hybridoma deposited with the ATCC and assigned accession number HB 9927, or a fragment thereof reactive with the Vβ5.3 variable region.

16. The method of claim 11 in which the body fluid is a sample of peripheral blood, plasma, cerebrospinal fluid, lymphatic fluid, peritoneal fluid or pleural fluid from said patient.

17. The method of claim 16 wherein the body fluid is a sample of peripheral blood.

18. The method according to claims 11, wherein, in said contacting step (a), said monoclonal antibody or fragment thereof is detectably labeled.

19. The method of claim 18 in which the body fluid or tissue is contacted in vitro.

20. The method of claim 18 in which the tissue is contacted in a histologic specimen.

21. The method of claim 18 in which the body fluid or tissue is contacted in vivo.

22. The method of claim 18 in which the body fluid is a sample of peripheral blood, plasma, cerebrospinal fluid, peritoneal fluid, or pleural fluid from said patient.

23. A method of detecting a Vβ5.3 T cell subset in a patient sample comprising:
    (a) contacting a patient sample with a monoclonal antibody or fragment thereof reactive with an epitope of the Vβ5.3 variable region of the beta chain of a T cell antigen receptor, wherein said monoclonal antibody or fragment thereof is detectably labeled; and
    (b) detecting whether immunospecific binding has occurred.

24. The method of claim 18 or 23, said detectably labeled antibody being.

25. The method of claim 23 in which the patient sample is body fluid or body tissue.

26. The method of claim 25 in which the sample is of peripheral blood, plasma, cerebrospinal fluid, lymphatic fluid, peritoneal fluid or pleural fluid from said patient.

27. The method of claim 26 wherein the sample is of peripheral blood.

28. An isolated humanized monoclonal antibody or fragment thereof reactive with an epitope of the Vβ5.3 variable region of the beta-chain of a T cell antigen receptor.

29. An isolated humanized monoclonal antibody or fragment thereof reactive with an epitope of the Vβ5.3 variable region of the beta-chain of a T cell antigen receptor, wherein said monoclonal antibody modulates a β chain 5.3 variable region expressing T cell subset in a mammal.

* * * * *

UNITED STATES PATENT AND TRADEMARK OFFICE
CERTIFICATE OF CORRECTION

PATENT NO. : 6,048,526
DATED : April 11, 2000
INVENTOR(S) : Skibbens et al.

It is certified that error appears in the above-identified patent and that said Letters Patent is hereby corrected as shown below:

Column 55,
Claim 24, after "antibody being" please insert -- W112 --.

Signed and Sealed this

Eleventh Day of September, 2001

Attest:

NICHOLAS P. GODICI
Attesting Officer
Acting Director of the United States Patent and Trademark Office